(12) United States Patent
Schultz et al.

(10) Patent No.: US 8,329,907 B2
(45) Date of Patent: Dec. 11, 2012

(54) AUTOTAXIN INHIBITORS

(75) Inventors: Melanie Schultz, Darmstadt (DE); Kai Schiemann, Seeheim-Jugenheim (DE); Wolfgang Staehle, Ingelheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/258,077

(22) PCT Filed: Mar. 9, 2010

(86) PCT No.: PCT/EP2010/001457
§ 371 (c)(1),
(2), (4) Date: Sep. 21, 2011

(87) PCT Pub. No.: WO2010/112124
PCT Pub. Date: Oct. 7, 2010

(65) Prior Publication Data
US 2012/0015976 A1    Jan. 19, 2012

(30) Foreign Application Priority Data
Apr. 2, 2009 (EP) .................................... 09004866

(51) Int. Cl.
C07D 401/10 (2006.01)
C07D 413/12 (2006.01)
C07D 417/12 (2006.01)
C07D 471/04 (2006.01)
C07D 495/04 (2006.01)

(52) U.S. Cl. ........ 546/114; 546/120; 546/143; 548/159; 548/221

(58) Field of Classification Search ............... 546/280.1, 546/114; 514/301
See application file for complete search history.

(56) References Cited

U.S. PATENT DOCUMENTS
2009/0197835 A1    8/2009 Carter et al.

FOREIGN PATENT DOCUMENTS
WO    2008/014286 A1    1/2008

OTHER PUBLICATIONS

West, Anthony R., Solid State Chemistry and its Applications, Wiley, New York, 1988, pp. 358 & 365.*
Banker, G.S. et al, "Modern Pharmaceutics, 3ed.", Marcel Dekker, New York, 1996, pp. 451 and 596.*
Cui, P., et al., "Synthesis and biological evaluation of phosphonate derivatives as autotaxin (ATX) inhibitors," Bioorganic & Medicinal Chemistry Letters, Feb. 20, 2007, vol. 17, No. 6, pp. 1634-1640. Pergamon, Elsevier Science, GB; Cited in ISR, dated Jun. 28, 2010, issued in corresponding PCT/EP2010/001457.
International Search Report, dated Jun. 28, 2010, issued in corresponding PCT/EP2010/001457.

* cited by examiner

*Primary Examiner* — Janet Andres
*Assistant Examiner* — Timothy R Rozof
(74) *Attorney, Agent, or Firm* — Millen, White, Zelano & Branigan, P.C.

(57) ABSTRACT

The present invention relates to compounds according to formula (I) as autotaxin inhibitors and the use of such compounds for the treatment and/or prophylaxis of physiological and/or pathophysiological conditions, which are caused, mediated and/or propagated by increased lysophosphatic acid levels and/or the activation of autotaxin, in particular of different cancers.

8 Claims, No Drawings

AUTOTAXIN INHIBITORS

TECHNICAL FIELD

The present invention relates to compounds as autotaxin inhibitors and the use of such compounds for the treatment and/or prophylaxis of physiological and/or pathophysiological conditions, which are caused, mediated and/or propagated by increased lysophosphatic acid levels and/or the activation of autotaxin, in particular of different cancers.

PRIOR ART

Autotaxin (ATX) is the enzyme apparently responsible for increased lysophosphatidic acid (LPA) levels in ascites and plasma of ovarian cancer patients (Xu et al., Clinical Cancer Research 1995, 1: 1223; Xu et al., Biochem. J. 1995, 309: 933), because it transforms lysophatidylcholine (LPC) to LPA (Tokumura et al., J. Biol. Chem. 2002, 277: 39436; Umezu-Gozo et al., J. Biol. Chem. 2002, 158: 227).

LPA is an intracellular lipid mediator, which influences a multiplicity of biologic and biochemical processes such as smooth muscle contraction, thrombocyte aggregation and apoptosis (Tigyi et al., Prog. Lipid Res. 2003, 42: 498; Mills et al., Nat. Rev. Cancer 2003, 3: 582; Lynch et al. Prost. Lipid Med. 2001, 64: 33). Furthermore, LPA is found in increased concentrations in plasma and ascites fluid of ovarian cancer patients of early and late phase.

LPA has been shown to promote tumor cell proliferation, survival, migration and invasion into neighboring tissues, which can result in the formation of metastases (Xu et al., Clinical Cancer Research 1995, 1: 1223; Xu et al., Biochem. J. 1995, 309: 933). These biological and pathobiological processes are switched on through the activation of G-protein coupled receptors by LPA (Contos et al., Mol. Pharm. 2000, 58: 1188).

Increased levels of LPA, altered receptor expression and altered responses to LPA may contribute to the initiation, progression or outcome of ovarian cancer. Furthermore, LPA is potentially also involved in prostate, breast, melanoma, head and neck, bowel and thyroid cancers.

For all these reasons in the course of treating tumor patients it is desirable to lower the LPA level. This can be achieved through the inhibition of enzymes which are involved in LPA biosynthesis, such as ATX (Sano et al., J. Biol. Chem. 2002, 277: 21197; Aoki et al., J. Biol. Chem. 2003, 277: 48737).

ATX belongs to the family of nucleotide pyrophosphatases and phosphodiesterases (Goding et al., Immunol. Rev. 1998, 161: 11). It represents an important starting point for anti-tumor therapy (Mills et al. Nat. Rev. Cancer 2003, 3: 582; Goto et al. J. Cell. Biochem. 2004, 92: 1115), since it is increasingly expressed in tumors and effects tumor cell proliferation and invasion into neighboring tissues both of which can lead to the formation of metastases (Nam et al. 2000, Oncogene, Vol. 19 Seite 241). In addition, in the course of angiogenesis ATX together with other anti-angiogenetic factors brings about blood vessel formation (Nam et al. Cancer Res. 2001, 61: 6938). Angiogenesis is an important process during tumor growth as it secures supply of the tumor with nutrients. Therefore, the inhibition of angiogenesis is an important starting point of cancer and tumor therapy, by means of which the tumor is to be starved (Folkman, Nature Reviews Drug Discovery 2007, 6: 273-286).

Mutagenesis studies suggest an essential function of the PDE domain of ATX for LPA generation. Though this particular PDE domain shares little homology with other known PDEs, it is considered to be druggable by NCEs.

No severe adverse effects are expected for the inhibition of ATX as LPA involved in wound healing in this context is produced by another pathway.

Since ATX is a relatively novel target, the amount of pre-clinical data on protein production, in vitro and in vivo assays is rather limited. No target-dependent cell model has been described but LPA itself is an excellent biomarker to follow ATX inhibition in vitro and in vivo. Neither structural information nor reference compounds are available.

Compounds that are capable of inhibiting ATX are described in Peng et al. (Bioorganic & Medicinal Chemistry Letters 2007, 17: 1634-1640). The there described compounds represent lipid analogues, which structurally share no similarities with the compounds of the present invention.

Further prior art documents are as follows:

DE 19834751 relates to heterobicyclic substituted (hetero) aromatic amidines or nitriles as thrombin inhibitors, anti-thrombotic agents or intermediates. The patent application does not mention the inhibition of autotaxin.

WO 99/24035 discloses benzothiazolecarboxamides as protein tyrosine kinase inhibitors. The patent application does not mention the inhibition of autotaxin.

WO 2002/102380 describes monocyclic or bicyclic carbocycles and heterocycles as factor Xa inhibitors. The patent application does not mention the inhibition of autotaxin.

WO 2003/097615 is directed to treatment of fibroproliferative diseases, such as diabetic neuropathy, involving identifying a non-peptide small molecule, selectively binding to a transforming growth factor beta kinase receptor and administering the molecule to subjects. The patent application does not mention the inhibition of autotaxin.

US 2003/0139431 relates to the use of quinazoline- and quinolino-guanidine derivatives for treating urge incontinence, pain, memory disorders, endocrine disorders, psychotic behaviour, diabetes, hypertension and gastrointestinal disorders. The patent application does not mention the inhibition of autotaxin.

WO 2004/099192 describes heterocycle substituted carboxylic acids which can be used in the treatment of metabolic disorders. The patent application does not mention the inhibition of autotaxin.

WO 2005/003100 deals with the use of quinazoline derivatives for the treatment of tubulin inhibitor mediated diseases, such as cancer, autoimmune diseases, autoimmune lymphoproliferative syndrome, inflammation and viral infections. The patent application does not mention the inhibition of autotaxin.

WO 2005/023761 is directed to cytokine inhibitors that are useful for treating rheumatoid arthritis and ulcerative colitis. The patent application does not mention the inhibition of autotaxin.

WO 2006/062972 discloses heterocyclic compounds that function as selective inhibitors of serine protease enzymes of the coagulation cascade and can be used for the treatment of arterial cardiovascular thromboembolic disorders, thromboembolic disorders, unstable angina and acute coronary syndrome. The patent application does not mention the inhibition of autotaxin.

WO 2006/066879 relates to benzo-heterocyclic compounds as voltage-gated potassium channel modulators. The patent application does not mention the inhibition of autotaxin.

WO 2006/072828 is directed to heteroaromatic quinoline compounds that serve as PDE inhibitors, in particular PDE10 inhibitors. These compounds can be used for the treatment of central nervous system disorders, such as psychotic disorders, anxiety disorders, movement disorders, mood disorders and neurodegenerative disorders. The patent application does not mention the inhibition of autotaxin.

WO 2006/074147 describes 4-arylamino-quinazoline as caspase-3 cascade activators that can be used for the treatment of cancer, autoimmune diseases, autoimmune lymphoproliferative syndrome, synovial cell hyperplasia, inflammation and viral infections. The patent application does not mention the inhibition of autotaxin.

WO 2006/099379 discloses benzoimidazole, benzoxazole and benzothiazole derivatives as betasecretase inhibitors. The patent application does not mention the inhibition of autotaxin.

WO 2006/108107 deals with diarylamine derivatives that are steroid hormone nuclear receptor modulators and can be used for the treatment of hypokalemia, hypertension, congestive heart failure, renal failure, artherosclerosis and obesity. The patent application does not mention the inhibition of autotaxin.

WO 2007/030582 relates to alkyl amine acompounds as potassium channel 1 function inhibitors that are useful for the treatment of arrhythmia, atrial fibrillation, atrial flutter, supraventricular arrhythmias, gastrointestinal disorders, esophagitis and asthma. The patent application does not mention the inhibition of autotaxin.

WO 2007/076034 describes fused bicyclic arene compounds that function as hepatitis C virus replication inhibitors and can be used for the treatment hepatitis C or other viral infections. The patent application does not mention the inhibition of autotaxin.

WO 2007/110868 discloses novel heterocyclic compounds that exhibit a dopamine receptor, preferably D4 receptor, antagonistic activity and/or a PDE5 inhibitory activity. These compounds can be used for the treatment of descreased libido, orgasm disorder and erectile dysfunction. The patent application does not mention the inhibition of autotaxin.

WO 2008/038051 is directed to heterocyclic compounds for the treatment of inflammatory or immunological diseases, such as cystic fibrosis. The patent application does not mention the inhibition of autotaxin.

WO 2008/038053 deals with heterocyclic compounds as voltage-dependent potassium channel inhibitors. The patent application does not mention the inhibition of autotaxin.

WO 2008/060621 is directed to aminopyrrolidines as chemokine receptor antagonists. The patent application does not mention the inhibition of autotaxin.

WO 2008/091580 relates to fungicidal amides and methods for controlling plant diseases caused by a fungal pathogen. The patent application does not mention the inhibition of autotaxin.

The citation of any reference in this application is not an admission that the reference is relevant prior art to this application.

DESCRIPTION OF THE INVENTION

The present invention has the object to provide novel autotaxin inhibitors.

The object of the present invention has surprisingly been solved in one aspect by providing a compound according to formula (I)

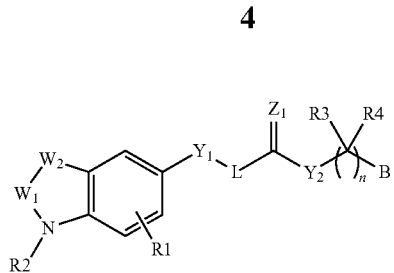

wherein:

$W_1$, $W_2$ together independently form "—N=N—, —C(O)—O—, —C(O)—S—, —C(O)—N(R5)-, —C(O)—C(R6)(R7)-, —N=C[N(R8)(R9)]-";

$Y_1$ is independently selected from the group consisting of "—C(O)—, —C(S)—, —N(R10)-C(O)—, —C(O)—N(R11)-, —C(R12)(R13)-, single bond";

$Y_2$ is independently selected from the group consisting of "—C(R14)(R15)-, —O—, —N(R16)-, —C(O)—NH—, single bond";

$Z_1$ is independently selected from the group consisting of "O, S, N(R17)";

L is independently selected from the group consisting of the group consisting of:

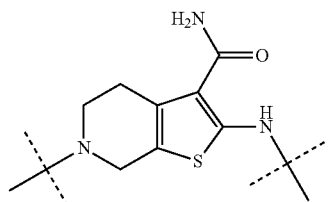

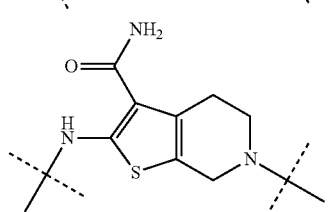

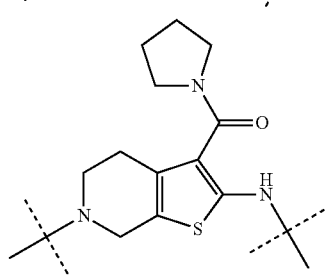

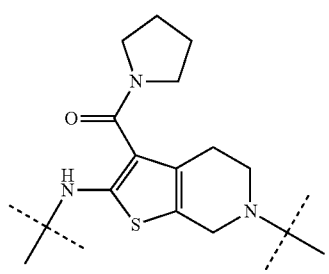

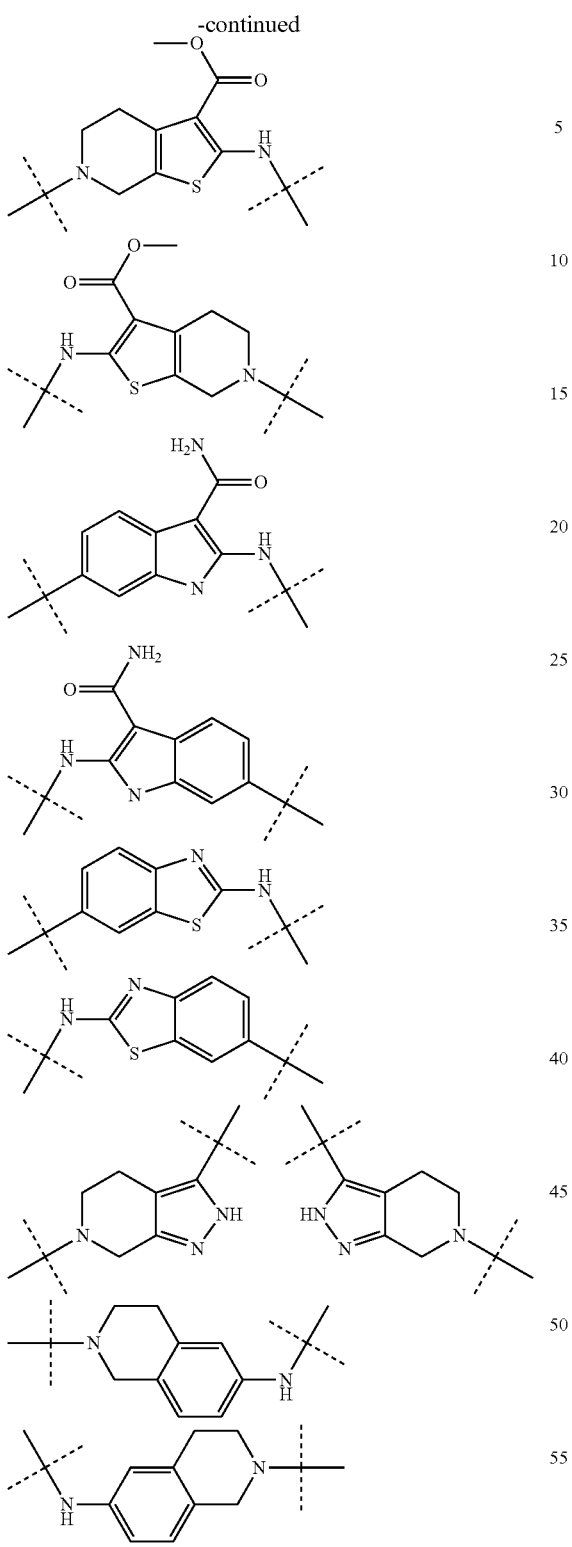

B is independently selected from the group consisting of "cycloalkyl, heterocyclyl, aryl, heteroaryl", wherein "cycloalkyl, heterocyclyl, aryl, heteroaryl" can be independently substituted with one or more identical or different substituents selected from the group consisting of:
"(i) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, halogen, —F, —Cl, —Br, —I, —CN, —CF$_3$, —N$_3$, —NH$_2$, —NHX1, —NX2X3, —NO$_2$, —OH, —OCF$_3$, —SCF$_3$, —SH, —O—SO$_3$H, —OP(O)(OH)$_2$, —CHO, —COOH, —C(O)NH$_2$, —SO$_3$H, —P(O)(OH)$_2$, —C(O)—X4, —C(O)O—X5, —C(O)NH—X6, —C(O)NX7X8, —O—X9, —O(—X10-O)$_a$—H (a=1,2,3,4,5), —O(—X11-O)$_b$—X12 (b=1,2,3,4,5), —OC(O)—X13, —OC(O)—O—X14, —OC(O)—NHX15, —O—C(O)—NX16X17, —OP(O)(OX18)(OX19), —OSi(X20)(X21)(X22), —OS(O$_2$)—X23, —NHC(O)—NH$_2$, —NHC(O)—X24, —NX25C(O)—X26, —NH—C(O)—O—X27, —NH—C(O)—NH—X28, —NH—C(O)—NX29X30, —NX31-C(O)—O—X32, —NX33-C(O)—NH—X34, —NX35-C(O)—NX36X37, —NHS(O$_2$)—X38, —NX39S(O$_2$)—X40, —S—X41, —S(O)—X42, —S(O$_2$)—X43, —S(O$_2$)NH—X44, —S(O$_2$)NX45X46, —S(O$_2$)O—X47, —P(O)(OX48)(OX49), —Si(X50)(X51)(X52), —C(NH)—NH$_2$, —C(NX53)-NH$_2$, —C(NH)—NHX54, —C(NH)—NX55X56, —C(NX57)-NHX58, —C(NX59)-NX60X61, —NH—C(O)—NH—O—X62, —NH—C(O)—NX63-O—X64, —NX65-C(O)—NX66-O—X67, —N(—C(O)—NH—O—X68)$_2$, —N(—C(O)—NX69-O—X70)$_2$, —N(—C(O)—NH—O—X71)(—C(O)—NX72-O—X73), —C(S)—X74, —C(S)—O—X75, —C(S)—NH—X76, —C(S)—NX77X78, —C(O)—NH—O—X79, —C(O)—NX80-O—X81, —C(S)—NH—O—X82, —C(S)—NX83-O—X84, —C(O)—NH—NH—X85, —C(O)—NH—NX86X87, —C(O)—NX88-NX89X90, —C(S)—NH—NH—X91, —C(S)—NH—NX92X93, —C(S)—NX94-NX95X96, —C(O)—C(O)—O—X97, —C(O)—C(O)—NH$_2$, —C(O)—C(O)—NHX98, —C(O)—C(O)—NX99X100, —C(S)—C(O)—O—X101, —C(O)—C(S)—O—X102, —C(S)—C(S)—O—X103, —C(S)—C(O)—NH$_2$, —C(S)—C(O)—NHX104, —C(S)—C(O)—NX105X106, —C(S)—C(S)—NH$_2$, —C(S)—C(S)—NHX107, —C(S)—C(S)—NX108X109, —C(O)—C(S)—NH$_2$, —C(O)—C(S)—NHX110, —C(O)—C(S)—NX111X112";

wherein X1, X2, X3, X4, X5, X6, X7, X8, X9, X10, X11, X12, X13, X14, X15, X16, X17, X18, X19, X20, X21, X22, X23, X24, X25, X26, X27, X28, X29, X30, X31, X32, X33, X34, X35, X36, X37, X38, X39, X40, X41, X42, X43, X44, X45, X46, X47, X48, X49, X50, X51, X52, X53, X54, X55, X56, X57, X58, X59, X60, X61, X62, X63, X64, X65, X66, X67, X68, X69, X70, X71, X72, X73, X74, X75, X76, X77, X78, X79, X80, X81, X82, X83, X84, X85, X86, X87, X88, X89, X90, X91, X92, X93, X94, X95, X96, X97, X98, X99, X100, X101, X102, X103, X104, X105, X106, X107, X108, X109, X110, X111, X112 are independently from each other selected from the group consisting of:

"alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively X7, X8 and/or X16, X17 and/or X29, X30 and/or X36, X37 and/or X45, X46 and/or X55, X56 and/or X60, X61 and/or X77, X78 and/or X86, X87 and/or X89, X90 and/or X92, X93 and/or X95, X96 and/or X99, X100 and/or X105, X106 and/or X108, X109 and/or X111, X112 respectively together can also form "heterocyclyl";

wherein optionally above substituents of substituents group (i) can in turn independently from each other be substituted with one or more identical or different substituents V;

R1, R2, R3, R4, R5, R6, R7, R8, R9, R10, R11, R12, R13, R14, R15, R16, R17 are independently from each other selected from the group consisting of: "V";

V is independently selected from the group consisting of: "(i) "hydrogen, alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl, halogen, —F, —Cl, —Br, —I, —CN, —CF$_3$, —N$_3$, —NH$_2$, —NHA1, —NA2A3, —NO$_2$, —OH, —OCF$_3$, —SCF$_3$, —SH, —O—SO$_3$H, —OP(O)(OH)$_2$, —CHO, —COOH, —C(O)NH$_2$, —SO$_3$H, —P(O)(OH)$_2$, —C(O)-A4, —C(O)O-A5, —C(O)NH-A6, —C(O)NA7A8, —O-A9, —O(-A10-O)$_a$—H (a=1, 2, 3, 4, 5), —O(-A11-O)$_b$-A12 (b=1, 2, 3, 4, 5), —OC(O)-A13, —OC(O)—O-A14, —OC(O)—NHA15, —O—C(O)—NA16A17, —OP(O)(OA18)(OA19), —OSi(A20)(A21)(A22), —OS(O$_2$)-A23, —NHC(O)—NH$_2$, —NHC(O)-A24, —NA25C(O)-A26, —NH—C(O)—O-A27, —NH—C(O)—NH-A28, —NH—C(O)—NA29A30, —NA31-C(O)—O-A32, —NA33-C(O)—NH-A34, —NA35-C(O)—NA36A37, —NHS(O$_2$)-A38, —NA39S(O$_2$)-A40, —S-A41, —S(O)-A42, —S(O$_2$)-A43, —S(O$_2$)NH-A44, —S(O$_2$)NA45A46, —S(O$_2$)O-A47, —P(O)(OA48)(OA49), —Si(A50)(A51)(A52), —C(NH)—NH$_2$, —C(NA53)-NH$_2$, —C(NH)—NHA54, —C(NH)—NA55A56, —C(NA57)-NHA58, —C(NA59)-NA60A61, —NH—C(O)—NH—O-A62, —NH—C(O)—NA63-O-A64, —NA65-C(O)—NA66-O-A67, —N(—C(O)—NH—O-A68)$_2$, —N(—C(O)—NA69-O-A70)$_2$, —N(—C(O)—NH—O-A71)(—C(O)—NA72-O-A73), —C(S)-A74, —C(S)—O-A75, —C(S)—NH-A76, —C(S)—NA77A78, —C(O)—NH—O-A79, —C(O)—NA80-O-A81, —C(S)—NH—O-A82, —C(S)—NA83-O-A84, —C(O)—NH—NH-A85, —C(O)—NH-NA86A87, —C(O)—NA88-NA89A90, —C(S)—NH—NH-A91, —C(S)—NH-NA92A93, —C(S)—NA94-NA95A96, —C(O)—C(O)—O-A97, —C(O)—C(O)—NH$_2$, —C(O)—C(O)—NHA98, —C(O)—C(O)—NA99A100, —C(S)—C(O)—O-A101, —C(O)—C(S)—O-A102, —C(S)—C(S)—O-A103, —C(S)—C(O)—NH$_2$, —C(S)—C(O)—NHA104, —C(S)—C(O)—NA105A106, —C(S)—C(S)—NH$_2$, —C(S)—C(S)—NHA107, —C(S)—C(S)—NA108A109, —C(O)—C(S)—NH$_2$, —C(O)—C(S)—NHA110, —C(O)—C(S)—NA111A112";

wherein A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, A36, A37, A38, A39, A40, A41, A42, A43, A44, A45, A46, A47, A48, A49, A50, A51, A52, A53, A54, A55, A56, A57, A58, A59, A60, A61, A62, A63, A64, A65, A66, A67, A68, A69, A70, A71, A72, A73, A74, A75, A76, A77, A78, A79, A80, A81, A82, A83, A84, A85, A86, A87, A88, A89, A90, A91, A92, A93, A94, A95, A96, A97, A98, A99, A100, A101, A102, A103, A104, A105, A106, A107, A108, A109, A110, A111, A112 are independently from each other selected from the group consisting of: "alkyl, ($C_9$-$C_{30}$)alkyl, cycloalkyl, cycloalkylalkyl, heterocyclyl, heterocyclylalkyl, aryl, arylalkyl, heteroaryl, heteroarylalkyl" and wherein alternatively A7, A8 and/or A16, A17 and/or A29, A30 and/or A36, A37 and/or A45, A46 and/or A55, A56 and/or A60, A61 and/or A77, A78 and/or A86, A87 and/or A89, A90 and/or A92, A93 and/or A95, A96 and/or A99, A100 and/or A105, A106 and/or A108, A109 and/or A111, A112 respectively together can also form "heterocyclyl";

wherein optionally above substituents of substituents group (i) can in turn independently from each other be substituted with one or more identical or different substituents V;

n is independently 0, 1, 2, 3 or 4;

and the physiologically acceptable salts, derivatives, prodrugs, solvates and stereoisomers thereof, including mixtures thereof in all ratios.

In a preferred embodiment, a compound according to formula (I) and above embodiments is provided, wherein:

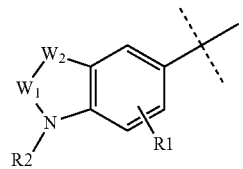

is independently substituted by a chemical group selected from the group consisting of:

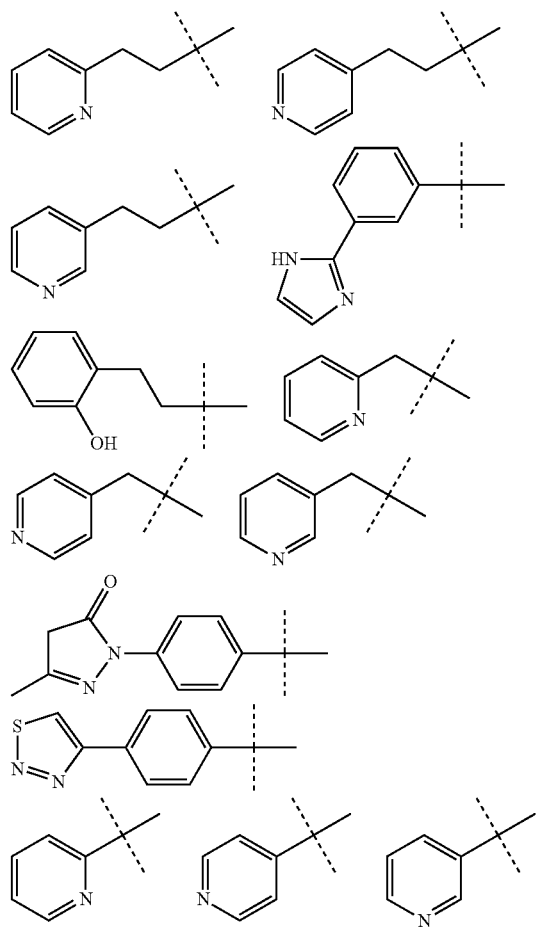

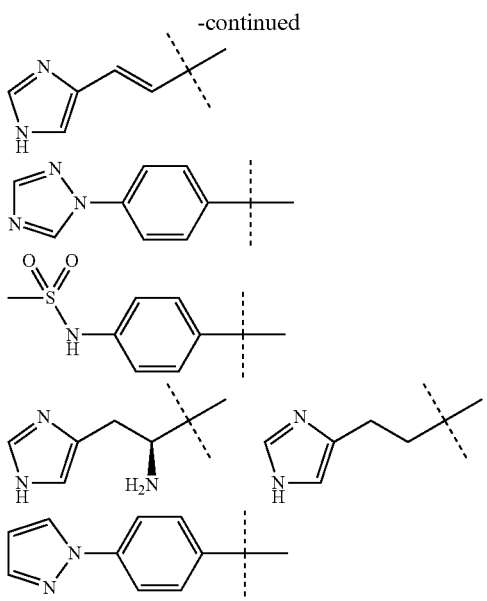

and the physiologically acceptable salts, derivatives, prodrugs, solvates and stereoisomers thereof, including mixtures thereof in all ratios.

In a preferred embodiment, a compound according to formula (I) and above embodiments is provided, wherein:
W₁, W₂ together independently form "—N═N—, —C(O)—O—"; and the physiologically acceptable salts, derivatives, prodrugs, solvates and stereoisomers thereof, including mixtures thereof in all ratios.

In a preferred embodiment, a compound according to formula (I) and above embodiments is provided, wherein:
Y₁ is independently selected from the group consisting of "—C(O)—, —N(R10)-C(O)—, —C(O)—N(R11)-, —OC(O)—, single bond";

and the physiologically acceptable salts, derivatives, prodrugs, solvates and stereoisomers thereof, including mixtures thereof in all ratios.

In a preferred embodiment, a compound according to formula (I) and above embodiments is provided, wherein:
Z₁ is independently "O";

and the physiologically acceptable salts, derivatives, prodrugs, solvates and stereoisomers thereof, including mixtures thereof in all ratios.

In a preferred embodiment, a compound according to formula (I) and above embodiments is provided, wherein:
B is independently selected from the group consisting of "4-chloro-phenyl, 3-trifluoromethyl-phenyl, 4-trifluoromethyl-phenyl, 4-trifluoromethylsulfanyl-phenyl, 4-trifluoromethoxy-phenyl, 3-chloro-4-trifluoromethoxy-phenyl, 3,5-bis-trifluoromethyl-phenyl, 4-isopropylphenyl, 4-tert.butyl-phenyl, 3,5-dichloro-phenyl, 4-chloro-2-fluoro-phenyl, 3-chloro-phenyl, 2-fluoro-5-trifluoromethyl-phenyl, 3-chloro-4-trifluoromethyl-phenyl, 3,4-dichloro-phenyl, 2,5-dichloro-phenyl, 2-methoxy-phenyl, 4-methoxy-phenyl, 4-nitro-phenyl, 4-bromo-phenyl, 5-chloro-2-methoxy-phenyl, 4-fluoro-phenyl, 3-bromo-4-fluoro-phenyl, 6-methoxy-1,2,3,4-tetrahydro-naphthalen-2-yl";

and the physiologically acceptable salts, derivatives, prodrugs, solvates and stereoisomers thereof, including mixtures thereof in all ratios.

In a preferred embodiment, a compound according to formula (I) and above embodiments is provided, wherein:
R1, R2, R3, R4, R5, R6, R7, R8, R9, R10, R11, R12, R13, R14, R15 are independently from each other selected from the group consisting of: "hydrogen, alkyl, methyl, isopropyl, tert.butyl, halogen, —F, —Br, —Cl, —CN, —CF₃, —SF₃, —OF₃, —O-alkyl, —O-methyl, —NO₂, —S(O)₂-methyl";

and the physiologically acceptable salts, derivatives, prodrugs, solvates and stereoisomers thereof, including mixtures thereof in all ratios.

In a preferred embodiment, a compound according to formula (I) and above embodiments is provided, wherein:
V is independently selected from the group consisting of "hydrogen, alkyl, methyl, isopropyl, tert.butyl, halogen, —F, —Br, —Cl, —CN, —CF₃, —SF₃, —OH, —O-alkyl, —O-methyl, —NO₂, —S(O)₂-methyl";

and the physiologically acceptable salts, derivatives, prodrugs, solvates and stereoisomers thereof, including mixtures thereof in all ratios.

In a preferred embodiment, a compound according to formula (I) and above embodiments is provided, wherein:
n is independently 0, 1 or 2;

and the physiologically acceptable salts, derivatives, prodrugs, solvates and stereoisomers thereof, including mixtures thereof in all ratios.

In a further preferred embodiment, a compound according to formulae (I) and above embodiments is provided, wherein:
W₁, W₂ together independently form "—N═N—, —C(O)—O—";
Y₁ is independently selected from the group consisting of "—C(O)—, —N(R10)-C(O)—, —C(O)—N(R11)-, —OC(O)—, single bond";
Z₁ is independently "O";
B is independently selected from the group consisting of "4-chloro-phenyl, 3-trifluoromethyl-phenyl, 4-trifluoromethyl-phenyl, 4-trifluoromethylsulfanyl-phenyl, 4-trifluoromethoxy-phenyl, 3-chloro-4-trifluoromethoxy-phenyl, 3,5-bis-trifluoromethyl-phenyl, 4-isopropylphenyl, 4-tert.butyl-phenyl, 3,5-dichloro-phenyl, 4-chloro-2-fluoro-phenyl, 3-chloro-phenyl, 2-fluoro-5-trifluoromethyl-phenyl, 3-chloro-4-trifluoromethyl-phenyl, 3,4-dichloro-phenyl, 2,5-dichloro-phenyl, 2-methoxy-phenyl, 4-methoxy-phenyl, 4-nitro-phenyl, 4-bromo-phenyl, 5-chloro-2-methoxy-phenyl, 4-fluoro-phenyl, 3-bromo-4-fluoro-phenyl, 6-methoxy-1,2,3,4-tetrahydro-naphthalen-2-yl";
R1, R2, R3, R4, R5, R6, R7, R8, R9, R10, R11, R12, R13, R14, R15 are independently from each other selected from the group consisting of: "hydrogen, alkyl, methyl, isopropyl, tert.butyl, halogen, —F, —Br, —Cl, —CN, —CF₃, —SF₃, —OF₃, —O-alkyl, —O-methyl, —NO₂, —S(O)₂-methyl"
V is independently selected from the group consisting of "hydrogen, alkyl, methyl, isopropyl, tert.butyl, halogen, —F, —Br, —Cl, —CN, —CF₃, —SF₃, —OH, —O-alkyl, —O-methyl, —NO₂, —S(O)₂-methyl";
n is independently 0, 1 or 2;
and the physiologically acceptable salts, derivatives, prodrugs, solvates and stereoisomers thereof, including mixtures thereof in all ratios.

In another aspect, the object of the present invention has surprisingly been solved by providing a compound selected from the group consisting of:

| Compound | | Name |
|---|---|---|
| Compound 1 | | 6-(1H-Benzotriazole-5-carbonyl)-2-[3-(4-chloro-phenyl)-ureido]-4,5,6,7-tetrahydro-thieno[2,3-c]pyridine-3-carboxylic acid amide |
| Compound 2 | | 2-[3-(4-Chloro-phenyl)-ureido]-6-(2-oxo-2,3-dihydro-benzooxazole-6-carbonyl)-4,5,6,7-tetrahydro-thieno[2,3-c]pyridine-3-carboxylic acid amide |
| Compound 3 | | 6-(1H-Benzotriazole-5-carbonyl)-2-[3-(4-trifluoromethyl-phenyl)-ureido]-4,5,6,7-tetrahydro-thieno[2,3-c]pyridine-3-carboxylic acid amide |
| Compound 4 | | 6-(1H-Benzotriazole-5-carbonyl)-2-[3-(4-isopropyl-phenyl)-ureido]-4,5,6,7-tetrahydro-thieno[2,3-c]pyridine-3-carboxylic acid amide |
| Compound 5 | | 6-(1H-Benzotriazole-5-carbonyl)-2-[3-(4-chloro-phenyl)-propionylamino]-4,5,6,7-tetrahydro-thieno[2,3-c]pyridine-3-carboxylic acid amide |
| Compound 6 | | 2-[3-(4-Chloro-phenyl)-propionylamino]-6-(2-oxo-2,3-dihydro-benzooxazole-6-carbonyl)-4,5,6,7-tetrahydro-thieno[2,3-c]pyridine-3-carboxylic acid amide |

-continued

| | | |
|---|---|---|
| Compound 7 | | 2-[3-(4-Isopropyl-phenyl)-ureido]-6-(2-oxo-2,3-dihydro-benzooxazole-6-carbonyl)-4,5,6,7-tetrahydro-thieno[2,3-c]pyridine-3-carboxylic acid amide |
| Compound 8 | | 2-[3-(3,5-Dichloro-phenyl)-ureido]-6-(2-oxo-2,3-dihydro-benzooxazole-6-carbonyl)-4,5,6,7-tetrahydro-thieno[2,3-c]pyridine-3-carboxylic acid amide |
| Compound 9 | | 6-(1H-Benzotriazole-5-carbonyl)-2-[2-(4-chloro-2-fluoro-phenyl)-acetylamino]-4,5,6,7-tetrahydro-thieno[2,3-c]pyridine-3-carboxylic acid amide |
| Compound 10 | | 2-[2-(4-Chloro-2-fluoro-phenyl)-acetylamino]-6-(2-oxo-2,3-dihydro-benzooxazole-6-carbonyl)-4,5,6,7-tetrahydro-thieno[2,3-c]pyridine-3-carboxylic acid amide |
| Compound 11 | | 6-(1H-Benzotriazole-5-carbonyl)-2-[2-(3-chloro-phenyl)-acetylamino]-4,5,6,7-tetrahydro-thieno[2,3-c]pyridine-3-carboxylic acid amide |
| Compound 12 | | 6-(1H-Benzotriazole-5-carbonyl)-2-[3-(3,5-dichloro-phenyl)-ureido]-4,5,6,7-tetrahydro-thieno[2,3-c]pyridine-3-carboxylic acid amide |
| Compound 13 | | 2-[2-(3-Chloro-phenyl)-acetylamino]-6-(2-oxo-2,3-dihydro-benzooxazole-6-carbonyl)-4,5,6,7-tetrahydro-thieno[2,3-c]pyridine-3-carboxylic acid amide |

-continued

| | | |
|---|---|---|
| Compound 14 | 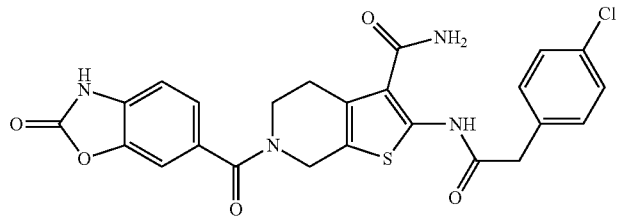 | 2-[2-(4-Chloro-phenyl)-acetylamino]-6-(2-oxo-2,3-dihydro-benzooxazole-6-carbonyl)-4,5,6,7-tetrahydro-thieno[2,3-c]pyridine-3-carboxylic acid amide |
| Compound 15 | 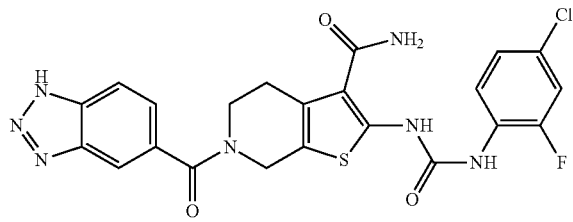 | 6-(1H-Benzotriazole-5-carbonyl)-2-[3-(4-chloro-2-fluoro-phenyl)-ureido]-4,5,6,7-tetrahydro-thieno[2,3-c]pyridine-3-carboxylic acid amide |
| Compound 16 | 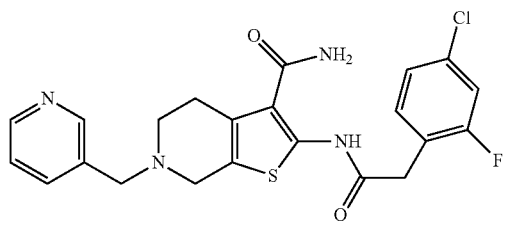 | 2-[2-(4-Chloro-2-fluoro-phenyl)-acetylamino]-6-pyridin-3-ylmethyl-4,5,6,7-tetrahydro-thieno[2,3-c]pyridine-3-carboxylic acid amide |
| Compound 17 | 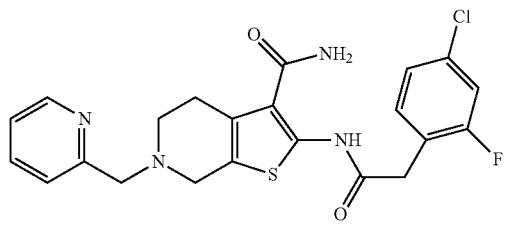 | 2-[2-(4-Chloro-2-fluoro-phenyl)-acetylamino]-6-pyridin-2-ylmethyl-4,5,6,7-tetrahydro-thieno[2,3-c]pyridine-3-carboxylic acid amide |
| Compound 18 | 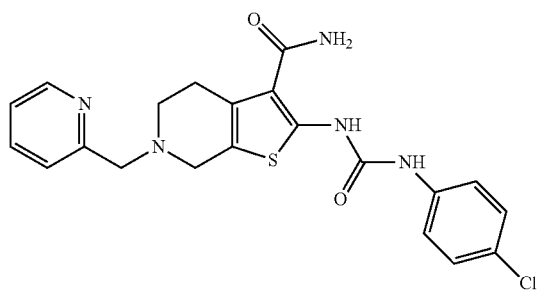 | 2-[3-(4-Chloro-phenyl)-ureido]-6-pyridin-2-ylmethyl-4,5,6,7-tetrahydro-thieno[2,3-c]pyridine-3-carboxylic acid amide |
| Compound 19 | 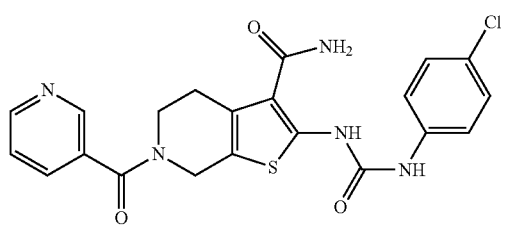 | 2-[3-(4-Chloro-phenyl)-ureido]-6-(pyridine-3-carbonyl)-4,5,6,7-tetrahydro-thieno[2,3-c]pyridine-3-carboxylic acid amide |

-continued

Compound 20 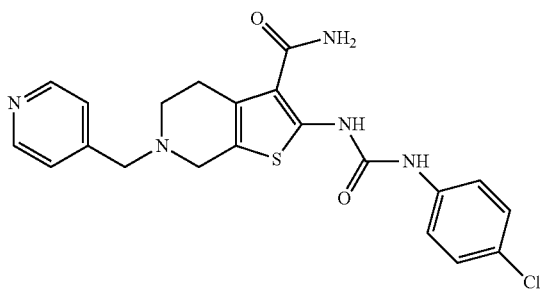 2-[3-(4-Chloro-phenyl)-ureido]-6-pyridin-4-ylmethyl-4,5,6,7-tetrahydro-thieno[2,3-c]pyridine-3-carboxylic acid amide Compound 21 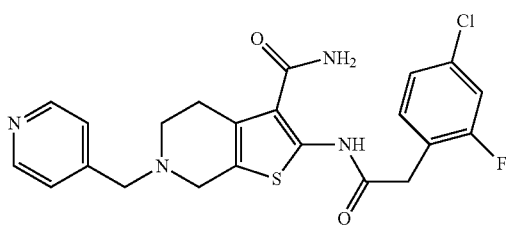 2-[2-(4-Chloro-2-fluoro-phenyl)-acetylamino]-6-pyridin-4-ylmethyl-4,5,6,7-tetrahydro-thieno[2,3-c]pyridine-3-carboxylic acid amide Compound 22 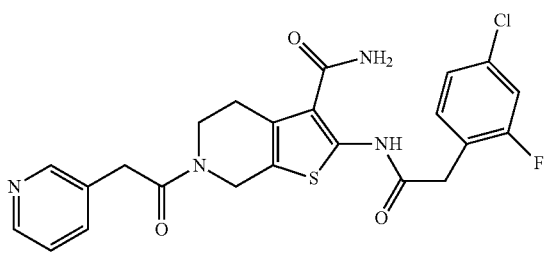 2-[2-(4-Chloro-2-fluoro-phenyl)-acetylamino]-6-(2-pyridin-3-yl-acetyl)-4,5,6,7-tetrahydro-thieno[2,3-c]pyridine-3-carboxylic acid amide Compound 23 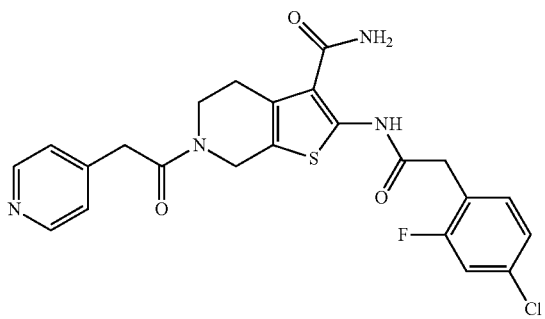 2-[2-(4-Chloro-2-fluoro-phenyl)-acetylamino]-6-(2-pyridin-4-yl-acetyl)-4,5,6,7-tetrahydro-thieno[2,3-c]pyridine-3-carboxylic acid amide Compound 24 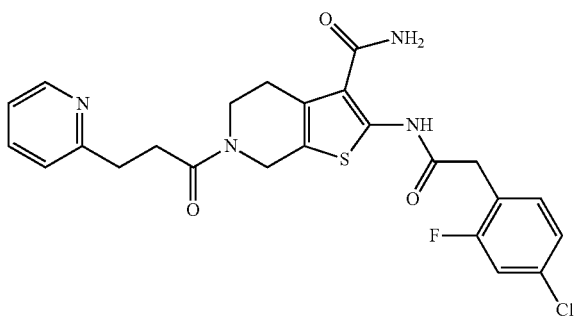 2-[2-(4-Chloro-2-fluoro-phenyl)-acetylamino]-6-(3-pyridin-2-yl-propionyl)-4,5,6,7-tetrahydro-thieno[2,3-c]pyridine-3-carboxylic acid amide -continued Compound 25

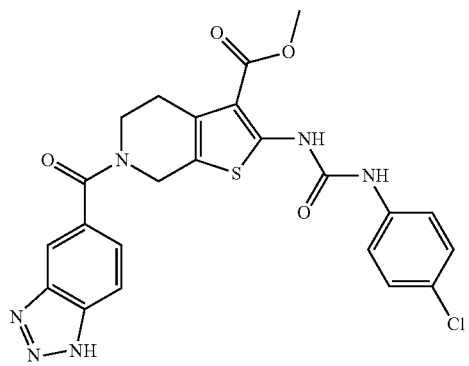

6-(1H-Benzotriazole-5-carbonyl)-2-[3-(4-chloro-phenyl)-ureido]-4,5,6,7-tetrahydro-thieno[2,3-c]pyridine-3-carboxylic acid methyl ester Compound 26

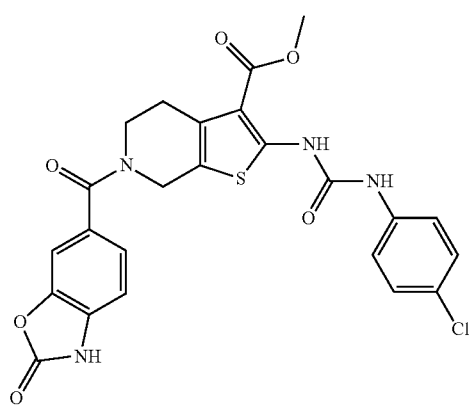

2-[3-(4-Chloro-phenyl)-ureido]-6-(2-oxo-2,3-dihydro-benzooxazole-6-carbonyl)-4,5,6,7-tetrahydro-thieno[2,3-c]pyridine-3-carboxylic acid methyl ester Compound 27

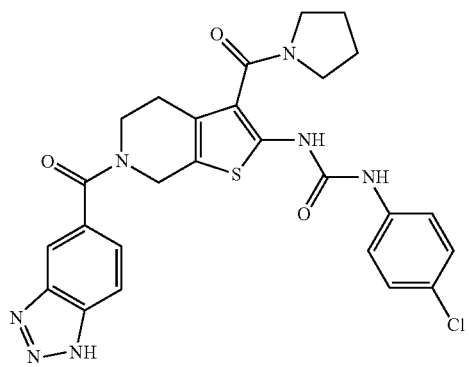

1-[6-(1H-Benzotriazole-5-carbonyl)-3-(pyrrolidine-1-carbonyl)-4,5,6,7-tetrahydro-thieno[2,3-c]pyridin-2-yl]-3-(4-chloro-phenyl)-urea Compound 28

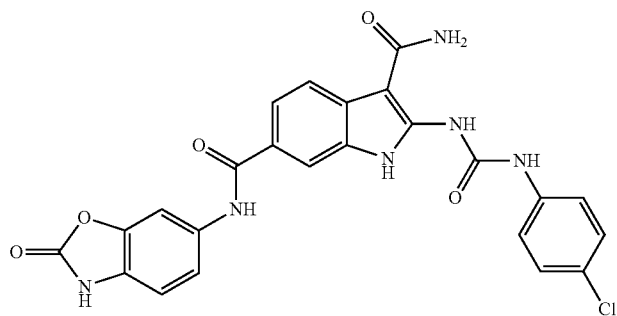

2-[3-(4-Chloro-phenyl)-ureido]-1H-indole-3,6-dicarboxylic acid 3-amide 6-[(2-oxo-2,3-dihydro-benzooxazol-6-yl)-amide]

-continued

Compound 29 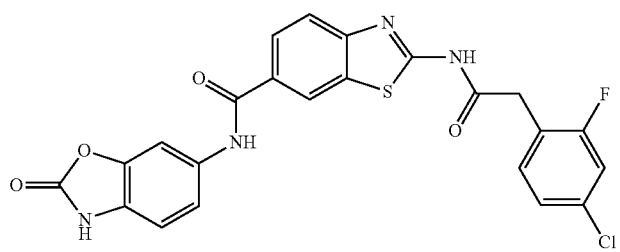 2-[2-(4-Chloro-2-fluoro-phenyl)-acetylamino]-benzothiazole-6-carboxylic acid (2-oxo-2,3-dihydro-benzooxazol-6-yl)-amide Compound 30 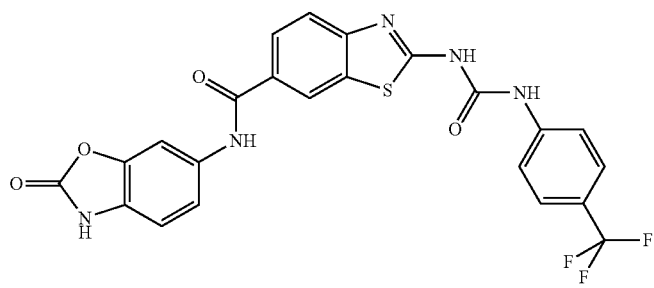 2-[3-(4-Trifluoromethyl-phenyl)-ureido]-benzothiazole-6-carboxylic acid (2-oxo-2,3-dihydro-benzooxazol-6-yl)-amide Compound 31 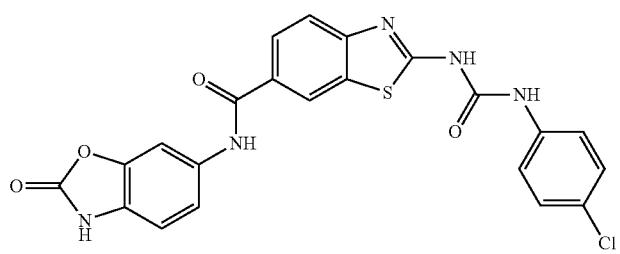 2-[3-(4-Chloro-phenyl)-ureido]-benzothiazole-6-carboxylic acid (2-oxo-2,3-dihydro-benzooxazol-6-yl)-amide Compound 32 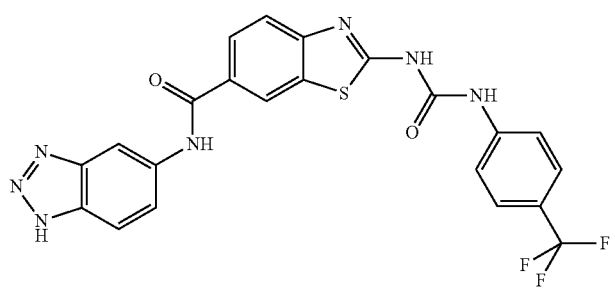 2-[3-(4-Trifluoromethyl-phenyl)-ureido]-benzothiazole-6-carboxylic acid (1H-benzotriazol-5-yl)-amide Compound 33 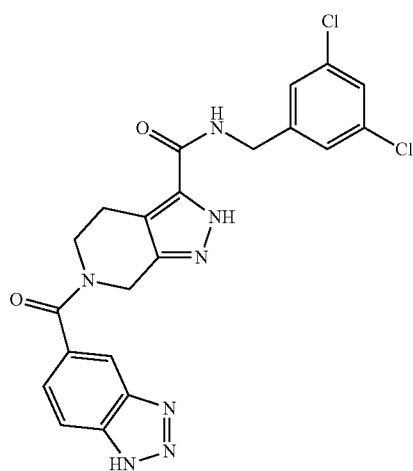 6-(1H-Benzotriazole-5-carbonyl)-4,5,6,7-tetrahydro-2H-pyrazolo[3,4-c]pyridine-3-carboxylic acid 3,5-dichloro-benzylamide -continued

| Compound 34 | 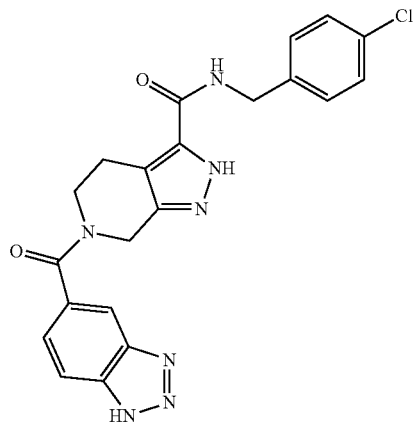 | 6-(1H-Benzotriazole-5-carbonyl)-4,5,6,7-tetrahydro-2H-pyrazolo[3,4-c]pyridine-3-carboxylic acid 4-chloro-benzylamide |

| Compound 35 | 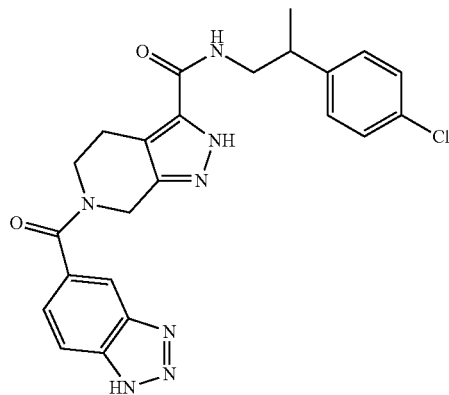 | 6-(1H-Benzotriazole-5-carbonyl)-4,5,6,7-tetrahydro-2H-pyrazolo[3,4-c]pyridine-3-carboxylic acid [2-(4-chloro-phenyl)-propyl]-amide |

| Compound 36 | 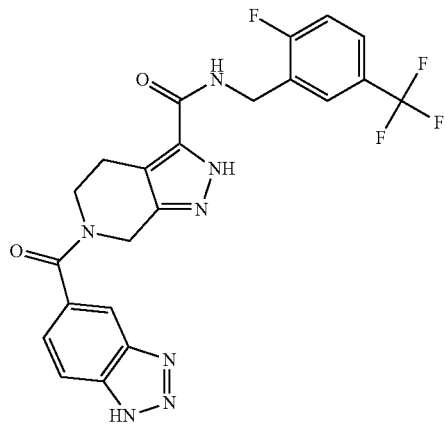 | 6-(1H-Benzotriazole-5-carbonyl)-4,5,6,7-tetrahydro-2H-pyrazolo[3,4-c]pyridine-3-carboxylic acid 2-fluoro-5-trifluoromethyl-benzylamide |

| Compound 37 | 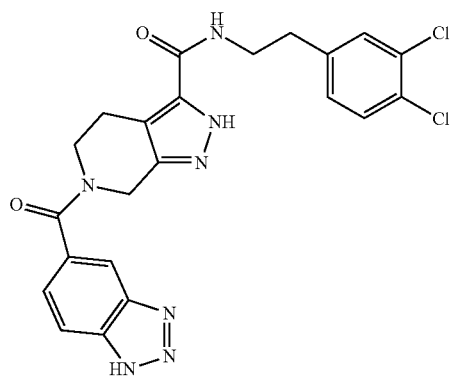 | 6-(1H-Benzotriazole-5-carbonyl)-4,5,6,7-tetrahydro-2H-pyrazolo[3,4-c]pyridine-3-carboxylic acid [2-(3,4-dichloro-phenyl)-ethyl]-amide |

| | | |
|---|---|---|
| Compound 38 | | 6-(1H-Benzotriazole-5-carbonyl)-4,5,6,7-tetrahydro-2H-pyrazolo[3,4-c]pyridine-3-carboxylic acid 2,5-dichloro-benzylamide |
| Compound 39 | | 6-(1H-Benzotriazole-5-carbonyl)-4,5,6,7-tetrahydro-2H-pyrazolo[3,4-c]pyridine-3-carboxylic acid [2-(4-chloro-phenyl)-ethyl]-amide |
| Compound 40 | | 6-(1H-Benzotriazole-5-carbonyl)-4,5,6,7-tetrahydro-2H-pyrazolo[3,4-c]pyridine-3-carboxylic acid [2-(4-chloro-phenyl)-1-hydroxymethyl-ethyl]-amide |
| Compound 41 | | 6-(1H-Benzotriazole-5-carbonyl)-4,5,6,7-tetrahydro-2H-pyrazolo[3,4-c]pyridine-3-carboxylic acid 2-methoxy-benzylamide |

-continued

| Compound 42 | [structure] | 6-(1H-Benzotriazole-5-carbonyl)-4,5,6,7-tetrahydro-2H-pyrazolo[3,4-c]pyridine-3-carboxylic acid [2-(3-chloro-phenyl)-ethyl]-amide |
| Compound 43 | [structure] | 6-(1H-Benzotriazole-5-carbonyl)-4,5,6,7-tetrahydro-2H-pyrazolo[3,4-c]pyridine-3-carboxylic acid [2-(4-nitro-phenyl)-ethyl]-amide |
| Compound 44 | [structure] | 6-(1H-Benzotriazole-5-carbonyl)-4,5,6,7-tetrahydro-2H-pyrazolo[3,4-c]pyridine-3-carboxylic acid [2-(4-bromo-phenyl)-ethyl]-amide |
| Compound 45 | [structure] | 6-(1H-Benzotriazole-5-carbonyl)-4,5,6,7-tetrahydro-2H-pyrazolo[3,4-c]pyridine-3-carboxylic acid 5-chloro-2-methoxy-benzylamide |

| | | |
|---|---|---|
| Compound 46 | 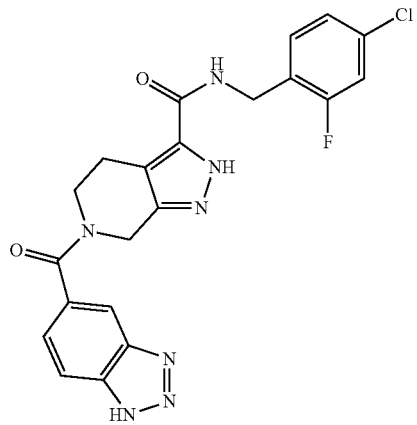 | 6-(1H-Benzotriazole-5-carbonyl)-4,5,6,7-tetrahydro-2H-pyrazolo[3,4-c]pyridine-3-carboxylic acid 4-chloro-2-fluoro-benzylamide |
| Compound 47 | 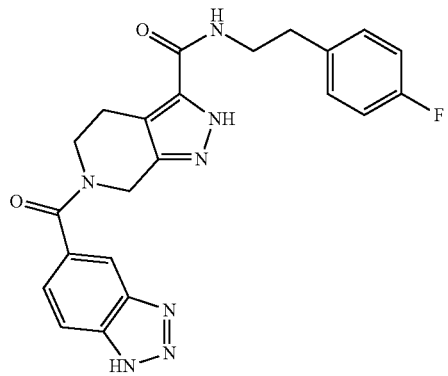 | 6-(1H-Benzotriazole-5-carbonyl)-4,5,6,7-tetrahydro-2H-pyrazolo[3,4-c]pyridine-3-carboxylic acid [2-(4-fluoro-phenyl)-ethyl]-amide |
| Compound 48 | 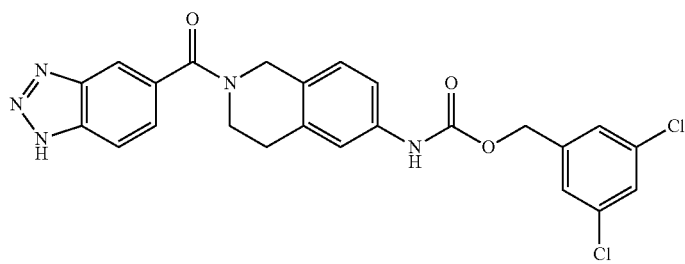 | [2-(1H-Benzotriazole-5-carbonyl)-1,2,3,4-tetrahydro-isoquinolin-6-yl]-carbamic acid 3,5-dichloro-benzyl ester |
| Compound 49 | 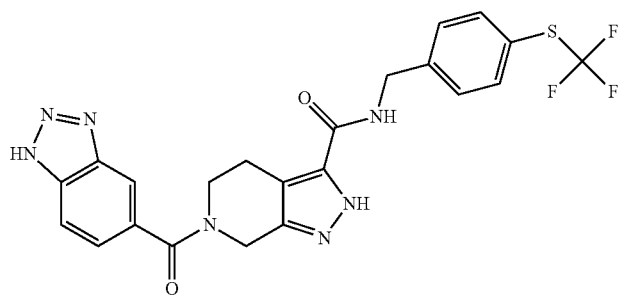 | 6-(1H-Benzotriazole-5-carbonyl)-4,5,6,7-tetrahydro-2H-pyrazolo[3,4-c]pyridine-3-carboxylic acid 4-trifluoromethylsulfanyl-benzylamide |

US 8,329,907 B2

-continued

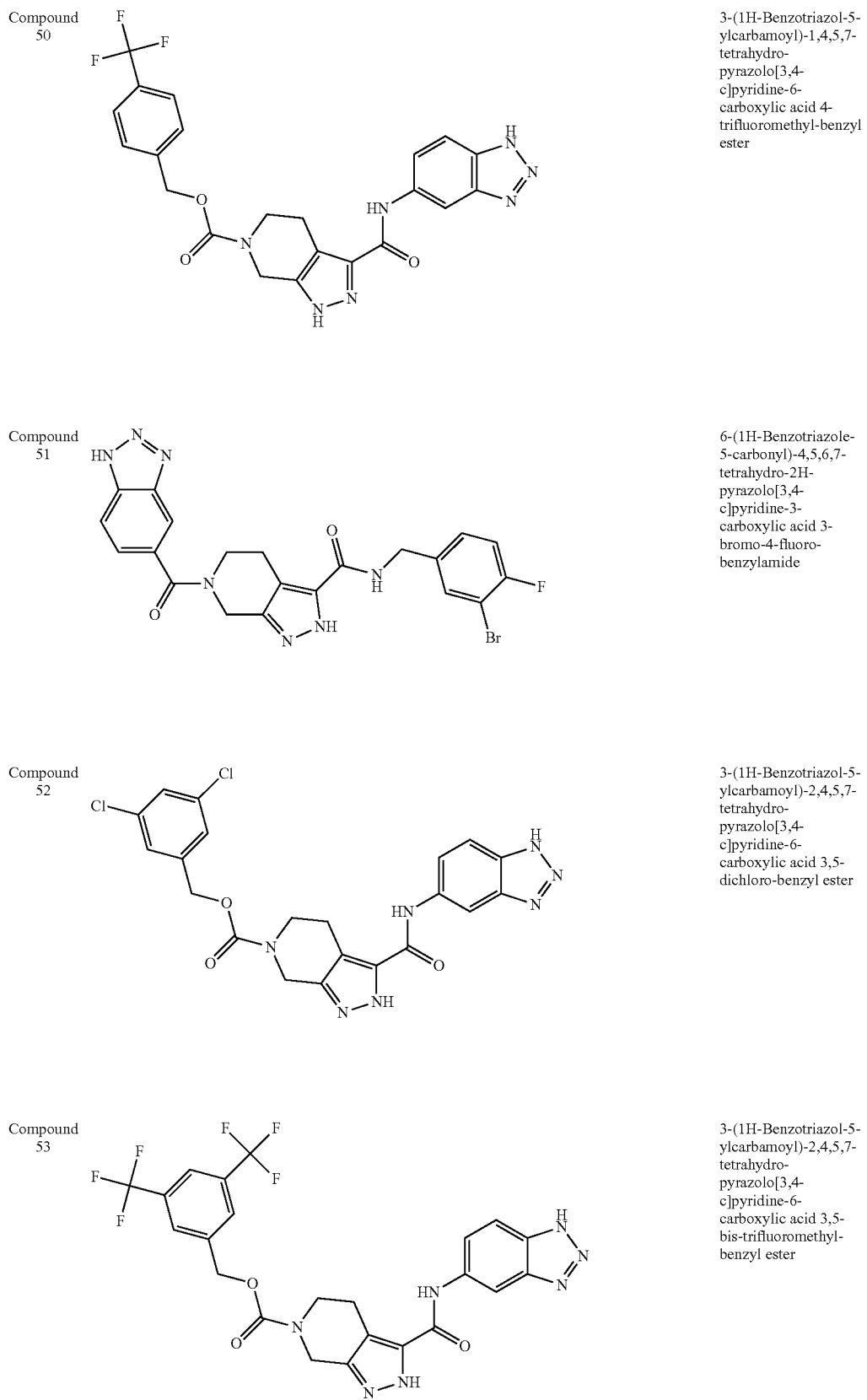

Compound 50: 3-(1H-Benzotriazol-5-ylcarbamoyl)-1,4,5,7-tetrahydro-pyrazolo[3,4-c]pyridine-6-carboxylic acid 4-trifluoromethyl-benzyl ester Compound 51: 6-(1H-Benzotriazole-5-carbonyl)-4,5,6,7-tetrahydro-2H-pyrazolo[3,4-c]pyridine-3-carboxylic acid 3-bromo-4-fluoro-benzylamide Compound 52: 3-(1H-Benzotriazol-5-ylcarbamoyl)-2,4,5,7-tetrahydro-pyrazolo[3,4-c]pyridine-6-carboxylic acid 3,5-dichloro-benzyl ester Compound 53: 3-(1H-Benzotriazol-5-ylcarbamoyl)-2,4,5,7-tetrahydro-pyrazolo[3,4-c]pyridine-6-carboxylic acid 3,5-bis-trifluoromethyl-benzyl ester

| | | |
|---|---|---|
| Compound 54 | 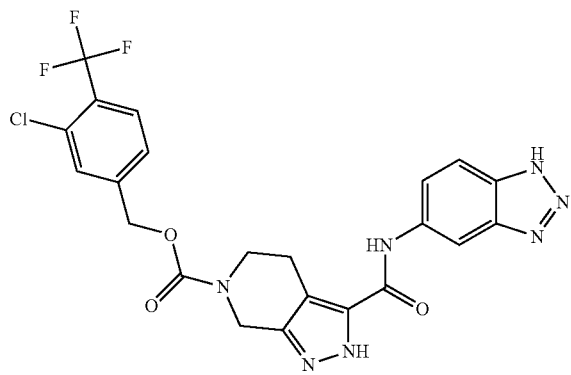 | 3-(1H-Benzotriazol-5-ylcarbamoyl)-2,4,5,7-tetrahydro-pyrazolo[3,4-c]pyridine-6-carboxylic acid 3-chloro-4-trifluoromethyl-benzyl ester |
| Compound 55 | 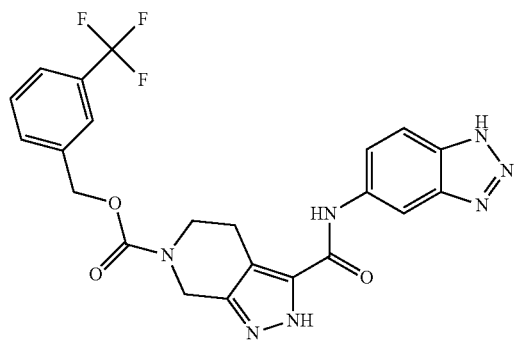 | 3-(1H-Benzotriazol-5-ylcarbamoyl)-2,4,5,7-tetrahydro-pyrazolo[3,4-c]pyridine-6-carboxylic acid 3-trifluoromethyl-benzyl ester |
| Compound 56 | 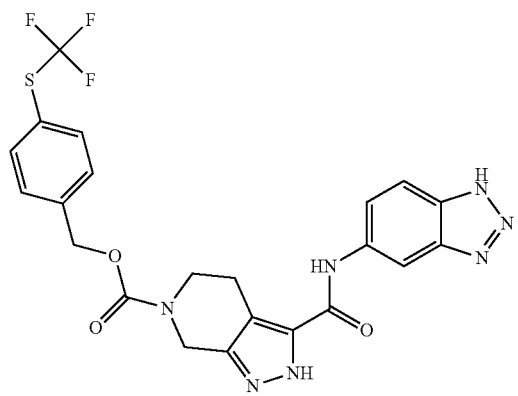 | 3-(1H-Benzotriazol-5-ylcarbamoyl)-2,4,5,7-tetrahydro-pyrazolo[3,4-c]pyridine-6-carboxylic acid 4-trifluoromethylsulfanyl-benzyl ester |
| Compound 57 | 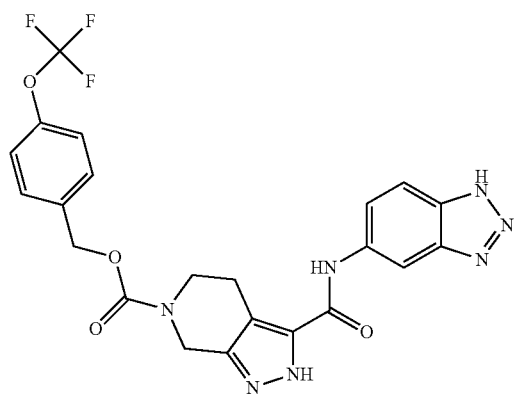 | 3-(1H-Benzotriazol-5-ylcarbamoyl)-2,4,5,7-tetrahydro-pyrazolo[3,4-c]pyridine-6-carboxylic acid 4-trifluoromethoxy-benzyl ester |

-continued

| Compound 58 | | 3-(1H-Benzotriazol-5-ylcarbamoyl)-2,4,5,7-tetrahydro-pyrazolo[3,4-c]pyridine-6-carboxylic acid 3-chloro-4-trifluoromethoxy-benzyl ester |
|---|---|---|
| Compound 59 | | (1H-Benzotriazol-5-yl)-{3-[3-(4-methoxy-phenyl)-piperidine-1-carbonyl]-2,4,5,7-tetrahydro-pyrazolo[3,4-c]pyridin-6-yl}-methanone |
| Compound 60 | | 6-(1H-Benzotriazole-5-carbonyl)-4,5,6,7-tetrahydro-2H-pyrazolo[3,4-c]pyridine-3-carboxylic acid 4-trifluoromethoxy-benzylamide |
| Compound 61 | | 6-(1H-Benzotriazole-5-carbonyl)-4,5,6,7-tetrahydro-2H-pyrazolo[3,4-c]pyridine-3-carboxylic acid 4-trifluoromethyl-benzylamide |
| Compound 62 | | 6-(1H-Benzotriazole-5-carbonyl)-4,5,6,7-tetrahydro-2H-pyrazolo[3,4-c]pyridine-3-carboxylic acid (6-methoxy-1,2,3,4-tetrahydro-naphthalen-2-yl)-amide |

| Compound 63 | 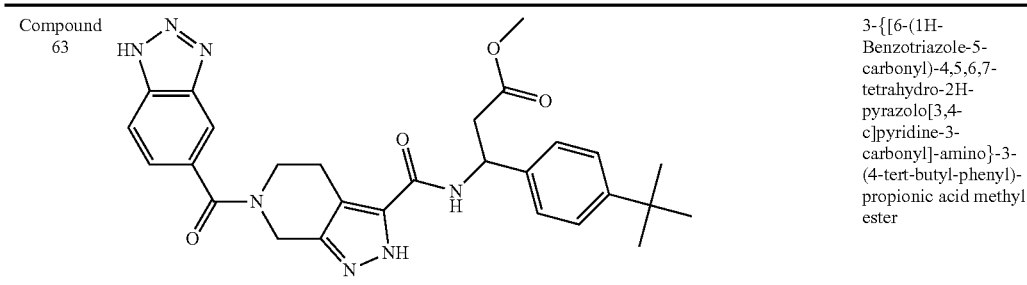 | 3-{[6-(1H-Benzotriazole-5-carbonyl)-4,5,6,7-tetrahydro-2H-pyrazolo[3,4-c]pyridine-3-carbonyl]-amino}-3-(4-tert-butyl-phenyl)-propionic acid methyl ester |

For the avoidance of doubt, if chemical name and chemical structure of the above illustrated compounds do not correspond by mistake, the chemical structure is regarded to unambiguously define the compound.

All the above generically or explicitly disclosed compounds, including preferred subsets/embodiments of the herein disclosed formula (I) and Compounds 1 to 63, are hereinafter referred to as compounds of the (present) invention.

The nomenclature as used herein for defining compounds, especially the compounds according to the invention, is in general based on the rules of the IUPAC organisation for chemical compounds and especially organic compounds.

The terms indicated for explanation of the above compounds of the invention always, unless indicated otherwise in the description or in the claims, have the following meanings:

The term "unsubstituted" means that the corresponding radical, group or moiety has no substituents.

The term "substituted" means that the corresponding radical, group or moiety has one or more substituents. Where a radical has a plurality of substituents, and a selection of various substituents is specified, the substituents are selected independently of one another and do not need to be identical.

The terms "alkyl" or "A" as well as other groups having the prefix "alk" for the purposes of this invention refer to acyclic saturated or unsaturated hydrocarbon radicals which may be branched or straight-chain and preferably have 1 to 8 carbon atoms, i.e. $C_1$-$C_8$-alkanyls, $C_2$-$C_8$-alkenyls and $C_2$-$C_8$-alkynyls. Alkenyls have at least one C—C double bond and alkynyls at least one C—C triple bond. Alkynyls may additionally also have at least one C—C double bond. Examples of suitable alkyl radicals are methyl, ethyl, n-propyl, isopropyl, n-butyl, isobutyl, sec-butyl, tert-butyl, n-pentyl, iso-pentyl, neo-pentyl, tert-pentyl, 2- or 3-methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl, ethylenyl (vinyl), propenyl (—CH$_2$CH═CH$_2$; —CH═CH—CH$_3$, —C(═CH$_2$)—CH$_3$), butenyl, pentenyl, hexenyl, heptenyl, octenyl, octadienyl, octadecenyl, octadec-9-enyl, icosenyl, icos-11-enyl, (Z)-icos-11-enyl, docosnyl, docos-13-enyl, (Z)-docos-13-enyl, ethynyl, propynyl (—CH$_2$—C≡CH, —C≡C—CH$_3$), butynyl, pentynyl, hexynyl, heptynyl, octynyl. Especially preferred is $C_{1-4}$-alkyl. A $C_{1-4}$-alkyl radical is for example a methyl, ethyl, propyl, isopropyl, butyl, isobutyl, tert-butyl.

The term "($C_9$-$C_{30}$)alkyl" for the purposes of this invention refers to acyclic saturated or unsaturated hydrocarbon radicals which may be branched or straight-chain and have 9 to 30 carbon atoms, i.e. $C_9$-$_{30}$-alkanyls, $C_9$-$_{30}$-alkenyls and $C_9$-$_{30}$-alkynyls. $C_9$-$_{30}$-Alkenyls have at least one C—C double bond and $C_9$-$_{30}$-alkynyls at least one C—C triple bond. $C_9$-$_{30}$-Alkynyls may additionally also have at least one C—C double bond. Examples of suitable ($C_9$-$C_{30}$)alkyl radicals are tetradecyl, hexadecyl, octadecyl, eicosanyl, cis-13-docosenyl (erucyl), trans-13-docosenyl (brassidyl), cis-15-tetracosenyl (nervonyl) and trans-15-tetracosenyl.

The term "cycloalkyl" for the purposes of this invention refers to saturated and partially unsaturated non-aromatic cyclic hydrocarbon groups/radicals, having 1 to 3 rings, that contain 3 to 20, preferably 3 to 12, most preferably 3 to 8 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl. Especially preferred are $C_3$-$C_9$-cycloalkyl and $C_4$-$C_8$-cycloalkyl. A $C_4$-$C_8$-cycloalkyl radical is for example a cyclobutyl, cyclopentyl, cyclohexyl, cycloheptyl, cyclooctyl.

The term "heterocyclyl" for the purposes of this invention refers to a mono- or polycyclic system of 3 to 20, preferably 5 or 6 to 14 ring atoms comprising carbon atoms and 1, 2, 3, 4, or 5 heteroatoms, in particular nitrogen, oxygen and/or sulfur which are identical or different. The cyclic system may be saturated, mono- or polyunsaturated but may not be aromatic. In the case of a cyclic system consisting of at least two rings the rings may be fused or spiro- or otherwise connected. Such "heterocyclyl" radicals can be linked via any ring member. The term "heterocyclyl" also includes systems in which the heterocycle is part of a bi- or polycyclic saturated, partially unsaturated and/or aromatic system, such as where the heterocycle is fused to an "aryl", "cycloalkyl", "heteroaryl" or "heterocyclyl" group as defined herein via any desired and possible ring member of the heterocycyl radical. The bonding to the compounds of the general formula can be effected via any possible ring member of the heterocycyl radical. Examples of suitable "heterocyclyl" radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl, indolinyl, indolinylmethyl, imidazolidinyl, 2-aza-bicyclo[2.2.2]octanyl.

The term "aryl" for the purposes of this invention refers to a mono- or polycyclic aromatic hydrocarbon systems having 3 to 14, preferably 5 to 14, more preferably 6 to 10 carbon atoms. The term "aryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the aryl radical. The bonding to the compounds of the general formula can be effected via any possible ring member of the aryl radical. Examples of suitable "aryl" radicals are phenyl, biphenyl, naphthyl, 1-naphthyl, 2-naphthyl and anthracenyl, but likewise indanyl, indenyl, or 1,2,3,4-tetrahydronaphthyl. The most preferred aryl is phenyl.

The term "heteroaryl" for the purposes of this invention refers to a 3 to 15, preferably 5 to 14, more preferably 5-, 6- or 7-membered mono- or polycyclic aromatic hydrocarbon radical which comprises at least 1, where appropriate also 2, 3, 4 or 5 heteroatoms, preferably nitrogen, oxygen and/or sulfur, where the heteroatoms are identical or different. The number of nitrogen atoms is preferably 0, 1, 2, or 3, and that of the oxygen and sulfur atoms is independently 0 or 1. The term "heteroaryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl"group as defined herein via any desired and possible ring member of the heteroaryl radical. The bonding to the compounds of the general formula can be effected via any possible ring member of the heteroaryl radical. Examples of suitable "heteroaryl"are acridinyl, benzdioxinyl, benzimidazolyl, benzisoxazolyl, benzodioxolyl, benzofuranyl, benzothiadiazolyl, benzothiazolyl, benzothienyl, benzoxazolyl, carbazolyl, cinnolinyl, dibenzofuranyl, dihydrobenzothienyl, furanyl, furazanyl, furyl, imidazolyl, indazolyl, indolinyl, indolizinyl, indolyl, isobenzylfuranyl, isoindolyl, isoquinolinyl, isoquinolyl, isothiazolyl, isoxazolyl, naphthyridinyl, oxadiazolyl, oxazolyl, phenazinyl, phenothiazinyl, phenoxazinyl, phthalazinyl, pteridinyl, purinyl, pyrazinyl, pyrazolyl, pyridazinyl, pyridinyl, pyridyl, pyrimidinyl, pyrimidyl, pyrrolyl, quinazolinyl, quinolinyl, quinolyl, quinoxalinyl, tetrazolyl, thiadiazolyl, thiazolyl, thienyl, thiophenyl, triazinyl, triazolyl.

For the purposes of the present invention, the terms "alkylcycloalkyl", "cycloalkylalkyl", "alkyl-heterocyclyl", "heterocyclylalkyl", "alkyl-aryl", "arylalkyl", "alkyl-heteroaryl" and "heteroarylalkyl" mean that alkyl, cycloalkyl, heterocycl, aryl and heteroaryl are each as defined above, and the cycloalkyl, heterocyclyl, aryl and heteroaryl radical is bonded to the compounds of the general formula via an alkyl radical, preferably $C_1$-$C_8$-alkyl radical, more preferably $C_1$-$C_4$-alkyl radical.

The term "alkyloxy" or "alkoxy" for the purposes of this invention refers to an alkyl radical according to above definition that is attached to an oxygen atom. The attachment to the compounds of the general formula is via the oxygen atom. Examples are methoxy, ethoxy and n-propyloxy, propoxy, isopropoxy. Preferred is "$C_1$-$C_4$-alkyloxy" having the indicated number of carbon atoms.

The term "cycloalkyloxy" or "cycloalkoxy" for the purposes of this invention refers to a cycloalkyl radical according to above definition that is attached to an oxygen atom. The attachment to the compounds of the general formula is via the oxygen atom. Examples are cyclopropyloxy, cyclobutyloxy, cyclopentyloxy, cyclohexyloxy, cycloheptyloxy, cyclooctyloxy. Preferred is "$C_3$-$C_9$cycloalkyloxy" having the indicated number of carbon atoms.

The term "heterocyclyloxy" for the purposes of this invention refers to a heterocyclyl radical according to above definition that is attached to an oxygen atom. The attachment to the compounds of the general formulae is via the oxygen atom. Examples are pyrrolidinyloxy, thiapyrrolidinyloxy, piperidinyloxy, piperazinyloxy.

The term "aryloxy" for the purposes of this invention refers to an aryl radical according to above definition that is attached to an oxygen atom. The attachment to the compounds of the general formula is via the oxygen atom. Examples are phenyloxy, 2-naphthyloxy, 1-naphthyloxy, biphenyloxy, indanyloxy. Preferred is phenyloxy.

The term "heteroaryloxy" for the purposes of this invention refers to a heteroaryl radical according to above definition that is attached to an oxygen atom. The attachment to the compounds of the general formula is via the oxygen atom. Examples are pyrrolyloxy, thienyloxy, furyloxy, imidazolyloxy, thiazolyloxy.

The term "carbonyl" or "carbonyl moiety" for the purposes of this invention refers to a —C(O)— group.

The term "alkylcarbonyl" for the purposes of this invention refers to a "alkyl-C(O)—" group, wherein alkyl is as defined herein.

The term "alkoxycarbonyl" or "alkyloxycarbonyl" for the purposes of this invention refers to a "alkyl-O—C(O)—" group, wherein alkyl is as defined herein.

The term "alkoxyalkyl" for the purposes of this invention refers to a "alkyl-O-alkyl-" group, wherein alkyl is as defined herein.

The term "haloalkyl" for the purposes of this invention refers to an alkyl group as defined herein comprising at least one carbon atom substituent with at least one halogen as defined herein.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro), or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom. Fluorine is most preferred, when the halogens are substituted on an alkyl (haloalkyl) or alkoxy group (e.g. $CF_3$ and $CF_3O$).

The term "hydroxyl" or "hydroxy" means an OH group.

The term "composition", as in pharmaceutical composition, for the purposes of this invention is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individualist need.

As used herein, the term "effective amount" refers to any amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers.

Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

The compounds of the invention may be present in the form of their double bond isomers as "pure" E or Z isomers, or in the form of mixtures of these double bond isomers.

Where possible, the compounds of the invention may be in the form of the tautomers, such as keto-enol tautomers.

It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in vivo to provide the bioactive agent (i.e. compounds of the invention) is a prodrug within the scope and spirit of the invention.

Various forms of prodrugs are well known in the art and are described for instance in:

(i) Wermuth C G et al., Chapter 31: 671-696, The Practice of Medicinal Chemistry, Academic Press 1996;

(ii) Bundgaard H, Design of Prodrugs, Elsevier 1985; and (iii) Bundgaard H, Chapter 5: 131-191, A Textbook of Drug Design and Development, Harwood Academic Publishers 1991.

Said references are incorporated herein by reference.

It is further known that chemical substances are converted in the body into metabolites which may where appropriate likewise elicit the desired biological effect—in some circumstances even in more pronounced form.

Any biologically active compound that was converted in vivo by metabolism from any of the compounds of the invention is a metabolite within the scope and spirit of the invention.

The compounds of the invention can, if they have a sufficiently basic group such as, for example, a secondary or tertiary amine, be converted with inorganic and organic acids into salts. The pharmaceutically acceptable salts of the compounds of the invention are preferably formed with hydrochloric acid, hydrobromic acid, iodic acid, sulfuric acid, phosphoric acid, methanesulfonic acid, p-toluenesulfonic acid, carbonic acid, formic acid, acetic acid, sulfoacetic acid, trifluoroacetic acid, oxalic acid, malonic acid, maleic acid, succinic acid, tartaric acid, racemic acid, malic acid, embonic acid, mandelic acid, fumaric acid, lactic acid, citric acid, taurocholic acid, glutaric acid, stearic acid, glutamic acid or aspartic acid. The salts which are formed are, inter alia, hydrochlorides, chlorided, hydrobromides, bromides, iodides, sulfates, phosphates, methanesulfonates, tosylates, carbonates, bicarbonates, formates, acetates, sulfoacetates, triflates, oxalates, malonates, maleates, succinates, tartrates, malates, embonates, mandelates, fumarates, lactates, citrates, glutarates, stearates, aspartates and glutamates. The stoichiometry of the salts formed from the compounds of the invention may moreover be an integral or non-integral multiple of one.

The compounds of the invention can, if they contain a sufficiently acidic group such as, for example, the carboxy, sulfonic acid, phosphoric acid or a phenolic group, be converted with inorganic and organic bases into their physiologically tolerated salts. Examples of suitable inorganic bases are ammonium, sodium hydroxide, potassium hydroxide, calcium hydroxide, and of organic bases are ethanolamine, diethanolamine, triethanolamine, ethylenediamine, t-butylamine, t-octylamine, dehydroabietylamine, cyclohexylamine, dibenzylethylene-diamine and lysine. The stoichiometry of the salts formed from the compounds of the invention can moreover be an integral or non-integral multiple of one.

It is likewise possible for the compounds of the invention to be in the form of their solvates and, in particular, hydrates which can be obtained for example by crystallization from a solvent or from aqueous solution. It is moreover possible for one, two, three or any number of solvate or water molecules to combine with the compounds of the invention to give solvates and hydrates.

By the term "solvate" is meant a hydrate, an alcoholate, or other solvate of crystallization.

It is known that chemical substances form solids which exist in different order states which are referred to as polymorphic forms or modifications. The various modifications of a polymorphic substance may differ greatly in their physical properties. The compounds of the invention can exist in various polymorphic forms and certain modifications may moreover be metastable. All these polymorphic forms of the compounds are to be regarded as belonging to the invention.

The compounds of the invention are surprisingly characterized by a strong and/or selective inhibition of autotaxin.

Due to their surprisingly strong and/or selective enzyme inhibition, the compounds of the invention can be advantageously administered at lower doses compared to other less potent or selective inhibitors of the prior art while still achieving equivalent or even superior desired biological effects. In addition, such a dose reduction may advantageously lead to less or even no medicinal adverse effects. Further, the high inhibition selectivity of the compounds of the invention may translate into a decrease of undesired side effects on its own regardless of the dose applied.

The compounds of the invention being autotaxin inhibitors generally have an inhibition constant $IC_{50}$ of less than about 30 μM, and preferably less than about 5 μM.

The object of the present invention has surprisingly been solved in another aspect by providing the use of a compound of the invention as autotaxin inhibitor.

The terms "inhibiting, inhibition and/or retardation" are intended to refer for the purposes of the present invention to as follows: "partial or complete inhibiting, inhibition and/or retardation". In this case, it is within the specialist knowledge of the average person skilled in the art to measure and determine such inhibiting, inhibition, and/or retardation by means of the usual methods of measurement and determination. Thus, a partial inhibiting, inhibition and/or retardation, for example, can be measured and determined in relation to a complete inhibiting, inhibition and/or retardation.

The object of the present invention has surprisingly been solved in another aspect by providing a process for the preparation of a compound of the invention, comprising the steps:

(a) reacting a compound of the formula (II),

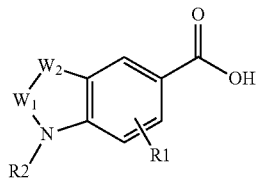

(II)

wherein $W_1$, $W_2$, R1, R2 have the meanings as indicated hereinwith, with a compound of the formula (III)

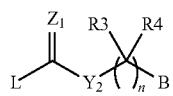

(III)

wherein L is selected from the group consisting of:

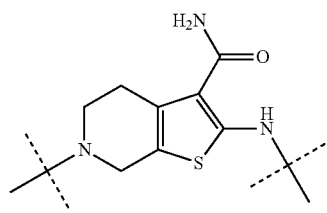

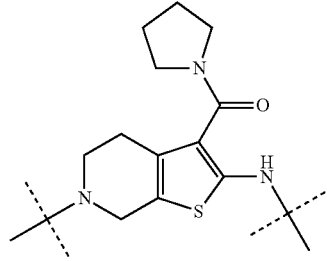

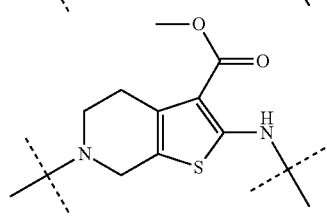

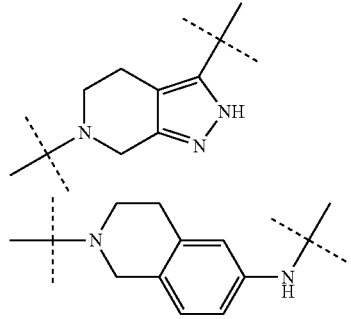

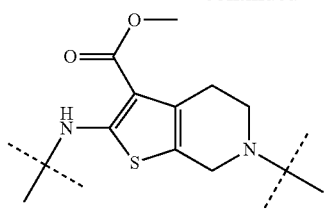

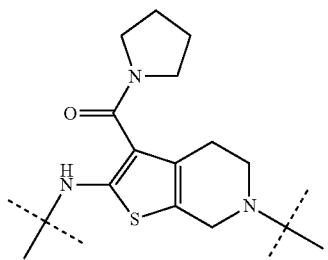

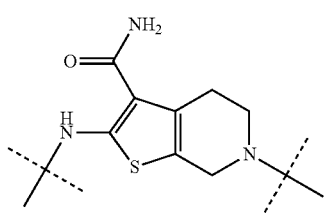

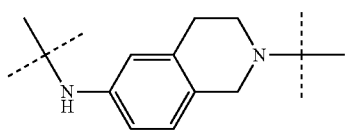

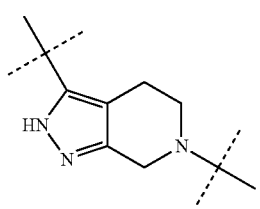

and wherein $Z_1$, $Y_2$, R3, R4, B, n have the meanings as indicated hereinwith, to yield a compound according to formula (I) as indicated hereinwith, in which $Y_1$ denotes "—C(O)—";

or (b) reacting a compound of the formula (II)

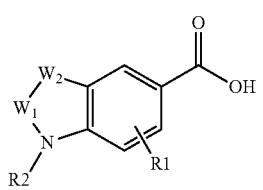

(II)

wherein $W_1$, $W_2$, R1, R2 have the meanings as indicated hereinwith, with a compound L selected from the group consisting of:

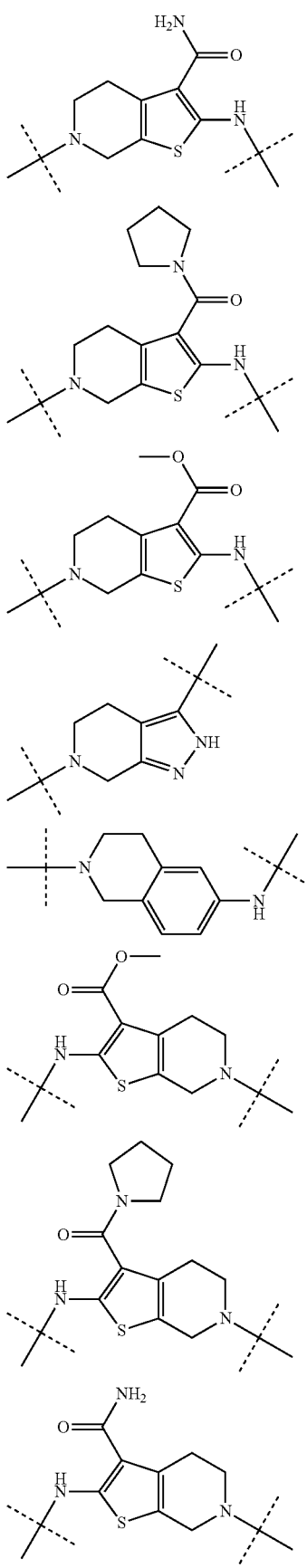

-continued

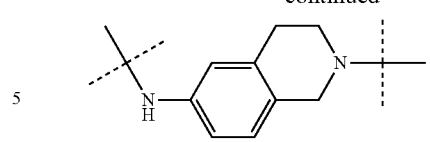

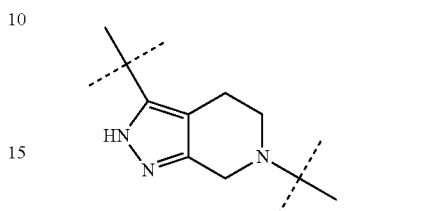

to yield a compound of the formula (IIa)

(IIa)

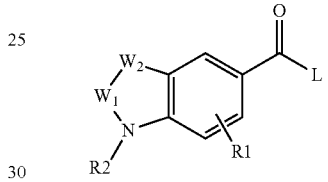

wherein $W_1$, $W_2$, R1, R2 have the meanings as indicated hereinwith; further reacting the compound of formula (IIa) with a compound of formula (IV)

(IV)

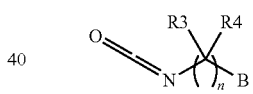

wherein R3, R4, B, n have the meanings as indicated hereinwith, to yield a compound according to formula (I) as indicated hereinwith, in which $Z_1$ denotes "O" and $Y_2$ denotes "—N(R16)-" and R16 denotes "H";

or (c) reacting a compound of the formula (Va) or (Vb)

(Va)

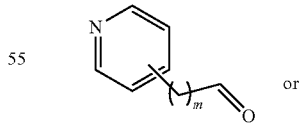

or (Vb)

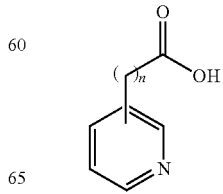

wherein m and n independently are 0, 1 or 2, with a compound of the formula (III)

(III)

wherein L is selected from the group consisting of:

and wherein $Z_1$, $Y_2$, R3, R4, B, n have the meanings as indicated in claim 1, to yield a compound according to formula (I) as indicated in claims 1 and 2, in which $Y_1$ denotes "—C(R12)(R13)- and R12, R13 both denote "H" or $Y_1$ denotes "—C(O)—", or (d) reacting a compound of the formula (VI)

HO(O)C-L         (VI)

wherein L is selected from the group consisting of:

with a compound of the formula (VII)

$$\text{(VII)}$$

wherein $W_1$, $W_2$, R1, R2 have the meanings as indicated hereinwith; to yield a compound of the formula (VIII)

$$\text{(VIII)}$$

wherein $W_1$, $W_2$, R1, R2 have the meanings as indicated hereinwith; further reacting the compound of formula (VIII) with a compound of formula (IV)

$$\text{(IV)}$$

wherein R3, R4, B, n have the meanings as indicated hereinwith, to yield a compound according to formula (I) as indicated hereinwith, in which $Y_1$ denotes "—N(R10)-C(O)—", R10 denotes "H", $Z_1$ denotes "O", $Y_2$ denotes "—N(R16)-" and R16 denotes "H";

or (e) reacting a compound of the formula (IX)

$$\text{(IX)}$$

wherein L is selected from the group consisting of:

and wherein $Z_1$, $Y_2$, R3, R4, B, n have the meanings as indicated hereinwith, with a compound of the formula (VII)

$$\text{(VII)}$$

wherein $W_1$, $W_2$, R1, R2 have the meanings as indicated hereinwith; to yield a compound according to formula (I) as indicated hereinwith, in which $Y_1$ denotes "—N(R10)-C(O)—" and R10 denotes "H".

or (f) reacting a compound of the formula (X)

$$\text{(X)}$$

wherein $W_1$, $W_2$, R1, R2, $Y_1$ have the meanings as indicated hereinwith, wherein L is selected from the group consisting of:

with a compound of formula (XI)

$$\text{(XI)}$$

wherein R3, R4, B, n have the meanings as indicated hereinwith, to yield a compound according to formula (I) as indicated hereinwith, in which $Z_1$ denotes "O", $Y_2$ denotes "—N(R16)-" and R16 denotes "H".

All crude products were subjected to standard chromatography using solvent mixtures containing methanol, ethanol, isopropanol, n-hexane, cyclohexane or petrol ether, respectively.

For a further detailed description of the manufacturing processes, please refer also to the examples and the following general description of the preferred conditions.

A physiologically acceptable salt of a compound of the invention can also be obtained by isolating and/or treating the compound of the invention obtained by the described reaction with an acid or a base.

The compounds of the invention and also the starting materials for their preparation are, are prepared by methods as described in the examples or by methods known per se, as described in the literature (for example in standard works, such as Houben-Weyl, Methoden der Organischen Chemie [Methods of Organic Chemistry], Georg Thieme Verlag, Stuttgart; Organic Reactions, John Wiley & Sons, Inc., New York), to be precise under reaction conditions which are known and suitable for the said reactions. Use can also be made here of variants which are known per se, but are not mentioned here in greater detail.

The starting materials for the claimed process may, if desired, also be formed in situ by not isolating them from the reaction mixture, but instead immediately converting them further into the compounds of the invention. On the other hand, it is possible to carry out the reaction stepwise.

Preferably, the reaction of the compounds is carried out in the presence of a suitable solvent, which is preferably inert under the respective reaction conditions. Examples of suitable solvents are hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate, or mixtures of the said solvents or mixtures with water. Polar solvents are in general preferred. Examples for suitable polar solvents are chlorinated hydrocarbons, alcohols, glycol ethers, nitriles, amides and sulfoxides or mixtures thereof. More preferred are amides, especially dimethylformamide (DMF).

As stated above, the reaction temperature is between about −100° C. and 300° C., depending on the reaction step and the conditions used.

Reaction times are generally in the range between some minutes and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 min and 48 hrs.

A base of a compound of the invention can be converted into the associated acid-addition salt using an acid, for example by reaction of equivalent amounts of the base and the acid in a preferably inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, aralphatic, aromatic or heterocyclic monobasic or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexanecarboxylic acid, glucose 1-phosphate, naphthalenemono- and -disulfonic acids or laurylsulfuric acid.

Salts with physiologically unacceptable acids, for example picrates, can be used to isolate and/or purify the compounds of the invention.

On the other hand, compounds of the invention can be converted into the corresponding metal salts, in particular alkali metal salts or alkaline earth metal salts, or into the corresponding ammonium salts, using bases (for example sodium hydroxide, potassium hydroxide, sodium carbonate or potassium carbonate). Suitable salts are furthermore substituted ammonium salts, for example the dimethyl-, diethyl- and diisopropylammonium salts, monoethanol-, diethanol- and diisopropanolammonium salts, cyclohexyl- and dicyclohexylammonium salts, dibenzylethylenediammonium salts, furthermore, for example, salts with arginine or lysine.

If desired, the free bases of the compounds of the invention can be liberated from their salts by treatment with strong bases, such as sodium hydroxide, potassium hydroxide, sodium carbonate or potassium carbonate, so long as no further acidic groups are present in the molecule. In the cases where the compounds of the invention have free acid groups, salt formation can likewise be achieved by treatment with bases. Suitable bases are alkali metal hydroxides, alkaline earth metal hydroxides or organic bases in the form of primary, secondary or tertiary amines.

Every reaction step described herein can optionally be followed by one or more working up procedures and/or isolating procedures. Suitable such procedures are known in the art, for example from standard works, such as Houben-Weyl, Methoden der organischen Chemie [Methods of Organic Chemistry], Georg-Thieme-Verlag, Stuttgart). Examples for such procedures include, but are not limited to evaporating a solvent, distilling, crystallization, fractionised crystallization, extraction procedures, washing procedures, digesting procedures, filtration procedures, chromatography, chromatography by HPLC and drying procedures, especially drying procedures in vacuo and/or elevated temperature.

The object of the present invention has surprisingly been solved in another aspect by providing a medicament comprising at least one compound of the invention.

The object of the present invention has surprisingly been solved in another aspect by providing a medicament comprising at least one compound of the invention for use in the treatment and/or prophylaxis of physiological and/or pathophysiological conditions, which are caused, mediated and/or propagated by increased lysophosphatic acid levels and/or the activation of autotaxin. A corresponding use for the preparation of a medicament for the treatment and/or prophylaxis of the aforementioned conditions is intended to be comprised.

The object of the present invention has surprisingly been solved in another aspect by providing a medicament comprising at least one compound of the invention for use in the treatment and/or prophylaxis of physiological and/or pathophysiological conditions selected from the group consisting of: "cancer, tumour, malignant tumours, benign tumours, solid tumours, sarcomas, carcinomas, hyperproliferative disorders, carcinoids, Ewing sarcomas, Kaposi sarcomas, brain tumours, tumours originating from the brain and/or the nervous system and/or the meninges, gliomas, glioblastomas, neuroblastomas, stomach cancer, kidney cancer, kidney cell carcinomas, prostate cancer, prostate carcinomas, connective tissue tumours, soft tissue sarcomas, pancreas tumours, liver tumours, head tumours, neck tumours, laryngeal cancer, oesophageal cancer, thyroid cancer, osteosarcomas, retinoblastomas, thymoma, testicular cancer, lung cancer, lung adenocarcinoma, small cell lung carcinoma, bronchial carcinomas, breast cancer, mamma carcinomas, intestinal cancer, colorectal tumours, colon carcinomas, rectum carcinomas, gynaecological tumours, ovary tumours/ovarian tumours, uterine cancer, cervical cancer, cervix carcinomas, cancer of body of uterus, corpus carcinomas, endometrial carcinomas, urinary bladder cancer, urogenital tract cancer, bladder cancer, skin cancer, epithelial tumours, squamous epithelial carcinoma, basaliomas, spinaliomas, melanomas, intraocular melanomas, leukaemias, monocyte leukaemia, chronic leukaemias, chronic myelotic leukaemia, chronic lymphatic leukemia, acute leukaemias, acute myelotic leukaemia, acute lymphatic leukemia, lymphomas, angiogenesis, arteriosclerosis, opthalmic diseases, choroidal neovascularization, diabetic retinopathy, inflammatory diseases, arthritis, neurodegeneration, restenosis, wound healing and/or transplant rejection". A corresponding use for the preparation of a medicament for the treatment and/or prophylaxis of the aforementioned conditions is intended to be comprised.

Compounds of the invention may be used in combination with one or more other active substances (ingredients, drugs) in the treatment, prevention, suppression or amelioration of diseases or conditions for which compounds of the invention or the other substances have utility. Typically the combination of the drugs is safer or more effective than either drug alone, or the combination is safer or more effective than would it be expected based on the additive properties of the individual drugs. Such other drug(s) may be administered, by a route and in an amount commonly used contemporaneously or sequentially with a compound of the invention. When a compound of the invention is used contemporaneously with one or more other drugs, a combination product containing such other drug(s) and the compound of the invention is preferred. However, combination therapy also includes therapies in which the compound of the invention and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of the invention.

Examples of other active substances (ingredients, drugs) that may be administered in combination with a compound of the invention, and either administered separately or in the same pharmaceutical composition, include, but are not limited to the compounds classes and specific compounds listed in Table 1:

TABLE 1

| | | |
|---|---|---|
| Alkylating agents | Cyclophosphamide | Lomustine |
| | Busulfane | Procarbazine |
| | Ifosfamide | Altretamine |
| | Melphalane | Estramustinphosphate |
| | Hexamethylmelamine | Mechlorethamine |
| | Thiotepa | Streptozocine |
| | Chlorambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (AeternaZentaris) |
| | Carboxyphthalatoplatinum | Satraplatin (Johnson |
| | Tetraplatin | Matthey) |
| | Ormiplatin | BBR-3464 (Hoffmann-La |
| | Iproplatin | Roche) |
| | | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycine |
| | 5-Fluoruracil | Fludarabine |
| | Floxuridine | Pentostatine |
| | 2-Chlordesoxyadenosine | Raltitrexede |
| | 6-Mercaptopurine | Hydroxyurea |
| | 6-Thioguanine | Decitabine (SuperGen) |
| | Cytarabine | Clofarabine (Bioenvision) |
| | 2-Fluordesoxycytidine | Irofulven (MGI Pharma) |
| | Methotrexate | DMDC (Hoffmann-La Roche) |
| | Idatrexate | Ethinylcytidine (Taiho) |

TABLE 1-continued

| | | |
|---|---|---|
| Topoisomerase inhibitors | Amsacrine<br>Epirubicine<br>Etoposide<br>Teniposide or Mitoxantrone<br>Irinotecane (CPT-11)<br>7-Ethyl-10-hydroxycamptothecine<br>Topotecane<br>Dexrazoxanet (TopoTarget)<br>Pixantrone (Novuspharma)<br>Rebeccamycin-Analogue (Exelixis)<br>BBR-3576 (Novuspharma) | Rubitecane (SuperGen)<br>Exatecanmesylate (Daiichi)<br>Quinamed (ChemGenex)<br>Gimatecane (Sigma- Tau)<br>Diflomotecane (Beaufour-Ipsen)<br>TAS-103 (Taiho)<br>Elsamitrucine (Spectrum)<br>J-107088 (Merck & Co)<br>BNP-1350 (BioNumerik)<br>CKD-602 (Chong Kun Dang)<br>KW-2170 (Kyowa Hakko) |
| Antitumour antibiotics | Dactinomycin (Actinomycin D)<br>Doxorubicin (Adriamycin)<br>Deoxyrubicin<br>Valrubicin<br>Daunorubicin (Daunomycin)<br>Epirubicin<br>Therarubicin<br>Idarubicin<br>Rubidazone<br>Plicamycinp<br>Porfiromycin<br>Cyanomorpholinodoxorubicin<br>Mitoxantron (Novantron) | Amonafide<br>Azonafide<br>Anthrapyrazole<br>Oxantrazole<br>Losoxantrone<br>Bleomycinsulfate (Blenoxan)<br>Bleomycinacid<br>Bleomycin A<br>Bleomycin B<br>Mitomycin C<br>MEN-10755 (Menarini)<br>GPX-100 (Gem Pharmaceuticals) |
| Antimitotic agents | Paclitaxel<br>Docetaxel<br>Colchicin<br>Vinblastine<br>Vincristine<br>Vinorelbine<br>Vindesine<br>Dolastatine 10 (NCI)<br>Rhizoxine (Fujisawa)<br>Mivobuline (Warner-Lambert)<br>Cemadotine (BASF)<br>RPR 109881A (Aventis)<br>TXD 258 (Aventis)<br>Epothilon B (Novartis)<br>T 900607 (Tularik)<br>T 138067 (Tularik)<br>Cryptophycin 52 (Eli Lilly)<br>Vinflunine (Fabre)<br>Auristatine PE (Teikoku Hormone)<br>BMS 247550 (BMS)<br>BMS 184476 (BMS)<br>BMS 188797 (BMS)<br>Taxoprexine (Protarga) | SB 408075 (GlaxoSmithKline)<br>E7010 (Abbott)<br>PG-TXL (Cell Therapeutics)<br>IDN 5109 (Bayer)<br>A 105972 (Abbott)<br>A 204197 (Abbott)<br>LU 223651 (BASF)<br>D 24851 (ASTA Medica)<br>ER-86526 (Eisai)<br>Combretastatine A4 (BMS)<br>Isohomohalichondrin-B (PharmaMar)<br>ZD 6126 (AstraZeneca)<br>PEG-Paclitaxel (Enzon)<br>AZ10992 (Asahi)<br>!DN-5109 (Indena)<br>AVLB (Prescient NeuroPharma)<br>Azaepothilon B (BMS)<br>BNP- 7787 (BioNumerik)<br>CA-4-Prodrug (OXiGENE)<br>Dolastatin-10 (NrH)<br>CA-4 (OXiGENE) |
| Aromatase inhibitors | Aminoglutethimide<br>Letrozole<br>Anastrazole<br>Formestane | Exemestane<br>Atamestane (BioMedicines)<br>YM-511 (Yamanouchi) |
| Thymidylatesynthase inhibitors | Pemetrexed (Eli Lilly)<br>ZD-9331 (BTG) | Nolatrexed (Eximias)<br>CoFactor ™ (BioKeys) |
| DNA antagonists | Trabectedine (PharmaMar)<br>Glufosfamide (Baxter International)<br>Albumin + 32P (Isotope Solutions)<br>Thymectacine (NewBiotics)<br>Edotreotide (Novartis) | Mafosfamide (Baxter International)<br>Apaziquone (Spectrum Pharmaceuticals)<br>O6-Benzylguanine (Paligent) |
| Farnesyltransferase inhibitors | Arglabine (NuOncology Labs)<br>Ionafarnibe (Schering-Plough)<br>BAY-43-9006 (Bayer) | Tipifarnibe (Johnson & Johnson)<br>Perillylalcohol (DOR BioPharma) |
| Pump inhibitors | CBT-1 (CBA Pharma)<br>Tariquidar (Xenova)<br>MS-209 (Schering AG) | Zosuquidar-Trihydrochloride (Eli Lilly)<br>Biricodar-Dicitrate (Vertex) |
| Histoneacetyltransferase inhibitors | Tacedinaline (Pfizer)<br>SAHA (Aton Pharma)<br>MS-275 (Schering AG) | Pivaloyloxymethylbutyrate (Titan)<br>Depsipeptide (Fujisawa) |
| Metalloproteinase inhibitors/<br>Ribonucleosidereduktase inhibitors | Neovastat (Aeterna Laboratories)<br>Marimastat (British Biotech)<br>Galliummaltolate (Titan)<br>Triapine (Vion) | CMT -3 (CollaGenex)<br>BMS-275291 (Celltech)<br>Tezacitabine (Aventis)<br>Didox (Molecules for Health) |

TABLE 1-continued

| | | |
|---|---|---|
| TNF-alpha agonists/ antagonists | Virulizine (Lorus Therapeutics) CDC-394 (Celgene) | Revimide (Celgene) |
| Endothelin-A receptor antagonists | Atrasentane (Abbot) ZD-4054 (AstraZeneca) | YM-598 (Yamanouchi) |
| Retinoic acid receptor agonists | Fenretinide (Johnson & Johnson) LGD-1550 (Ligand) | Alitretinoin (Ligand) |
| Immunomodulators | Interferon Oncophage (Antigenics) GMK (Progenies) Adenocarzinoma vaccine (Biomira) CTP-37 (AVI BioPharma) JRX-2 (Immuno-Rx) PEP-005 (Peplin Biotech) Synchrovax vaccine (CTL Immuno) Melanoma vaccine (CTL Immuno) p21-RAS vaccine (GemVax) | Dexosome therapy (Anosys) Pentrix (Australian Cancer Technology) JSF-154 (Tragen) Cancer vaccine (Intercell) Noreline (Biostar) BLP-25 (Biomira) MGV (Progenics) 13-Alethine (Dovetail) CLL-Thera (Vasogen) |
| Hormonal and anti-hormonal agents | Estrogens Conjugated Estrogens Ethinylestradiole Chlorotrianisen Idenestrole Hydroxyprogesteroncaproate Medroxyprogesterone Testosterone Testosteronpropionate Fluoxymesterone Methyltestosterone Diethylstilbestrole Megestrole Tamoxifen Toremofine Dexamethasone | Prednisone Methylprednisolone Prednisolone Aminoglutethimide Leuprolide Goserelin Leuporelin Cetrorelix Bicalutamide Flutamide Octreotide Nilutamide Mitotane P-04 (Novogen) 2-Methoxyoestradiol (EntreMed) Arzoxifen (Eli Lilly) |
| Photodynamic agents | Talaporfine (Light Sciences) Theralux (Theratechnologies) Motexafin Gadolinium (Pharmacyclics) | Pd-Bacteriopheophorbide (Yeda) Lutetium-Texaphyrine (Pharmacyclics) Hypericine |
| Tyrosinkinase inhibitors | Imatinib (Novartis) Leflunomid (Sugen/Pharmacia) ZD1839 (AstraZeneca) Erlotinib (Oncogene Science) Canertjnib (Pfizer) Squalamin (Genaera) SU5416 (Pharmacia) SU6668 (Pharmacia) ZD4190 (AstraZeneca) ZD6474 (AstraZeneca) Vatalanib (Novartis) PKI166 (Novartis) GW2016 (GlaxoSmithKline) EKB-509 (Wyeth) EKB-569 (Wyeth) | Kahalid F (PharmaMar) CEP-701 (Cephalon) CEP-751 (Cephalon) MLN518 (Millenium) PKC412 (Novartis) Phenoxodiol O Trastuzumab (Genentech) C225 (ImClone) rhu-Mab (Genentech) MDX-H210 (Medarex) 2C4 (Genentech) MDX-447 (Medarex) ABX-EGF (Abgenix) IMC-1C11 (ImClone) |
| Different agents | SR-27897 (CCK-A inhibitor, Sanofi-Synthelabo) Tocladesine (cyclic-AMP agonist, Ribapharm) Alvocidib (CDK inhibitor, Aventis) CV-247 (COX-2 Inhibitor, Ivy Medical) P54 (COX-2 inhibitor, Phytopharm) CapCell ™ (CYP450 stimulans, Bavarian Nordic) GCS-IOO (gal3 antagonist, GlycoGenesys) G17DT immunogen (Gastrin inhibitor, Aphton) Efaproxiral (Oxygenator, | BCX-1777 (PNP inhibitor, BioCryst) Ranpirnase (Ribonuclease stimulans, Alfacell) Galarubicin (RNA synthesis inhibitor, Dong-A) Tirapazamin (reducing agent, SRI International) N-Acetylcystein (reducing agent, Zambon) R-Flurbiprofen (NF-kappaB inhibitor, Encore) 3CPA (NF-kappaB inhibitor, Active Biotech) Seocalcitol (Vitamin-D receptor agonist, Leo) 131-I-TM-601 (DNA |

TABLE 1-continued

| | |
|---|---|
| Allos Therapeutics) | antagonist, TransMolecular) |
| PI-88 (Heparanase inhibitor, Progen) | Eflornithin (ODC inhibitor, ILEX Oncology) |
| Tesmilifen (Histamine antagonist, YM BioSciences) | Minodronic acid (Osteoclasts inhibitor, Yamanouchi) |
| Histamine (Histamine-H2 receptor agonist, Maxim) | Indisulam (p53 stimulans, Eisai) |
| Tiazofurin (IMPDH inhibitor, Ribapharm) | Aplidin (PPT inhibitor, PharmaMar) |
| Cilengitide (Integrine antagonist, Merck KGaA) | Rituximab (CD20 antibody, Genentech) |
| SR-31747 (IL-1 antagonist, Sanofi-Synthelabo) | Gemtuzumab (CD33 antibody, Wyeth Ayerst) |
| CCI-779 (mTOR kinase inhibitor, Wyeth) | PG2 (Hematopoesis enhancer, Pharmagenesis) |
| Exisulind (PDE-V inhibitor, Cell Pathways) | Immunol ™ (Triclosan oral irrigation, Endo) |
| CP-461 (PDE-V inhibitor, Cell Pathways) | Triacetyluridine (Uridine prodrug, Wellstat) |
| AG-2037 (GART inhibitor, Pfizer) | SN-4071 (sarcoma agent, Signature BioScience) |
| WX-UK1 (Plasminogen activator inhibitor, Wilex) | TransMID-107 ™ (Immunotoxine, KS Biomedix) |
| PBI-1402 (PMN stimulans, ProMetic LifeSciences) | PCK-3145 (Apoptosis enhancer, Procyon) |
| Bortezomib (Proteasome inhibitor, Millennium) | Doranidazole (Apoptosis enhancer, Pola) |
| SRL-172 (T-cell stimulans, SR Pharma) | CHS-828 (cytotoxic agent, Leo) |
| TLK-286 (Glutathione-S-transferase inhibitor, Telik) | trans-Retinoic acid (Differentiator, NIH) |
| PT-100 (Growth factor agonist, Point Therapeutics) | MX6 (Apoptosis enhancer, MAXIA) |
| Midostaurin (PKC inhibitor, Novartis) | Apomin (Apoptosis enhancer, ILEX Oncology) |
| Bryostatin-1 (PKC stimulans, GPC Biotech) | Urocidine (Apoptosis enhancer, Bioniche) |
| CDA-II (Apoptosis enhancer, Everlife) | Ro-31-7453 (Apoptosis enhancer, La Roche) |
| SDX-101 (Apoptosis enhancer, Salmedix) | Brostallicin (Apoptosis enhancer, Pharmacia) |
| Ceflatonin (Apoptosis enhancer, ChemGenex) | |

In a preferred embodiment, a compound of the invention is administered in combination with one or more known antitumor agents, such as the following: estrogen receptor modulators, androgen receptor modulators, retinoid receptor modulators, cytotoxics, antiproliferative agents, prenyl proteintransferase inhibitors, HMG-CoA-reductase inhibitors, HIV protease inhibitors, reverse transcriptase inhibitors, angiogenesis inhibitors.

The compounds of the invention are in particular well suited for administration in combination with radiotherapy. The synergistic effects of VEGF inhibition in combination with radiotherapy are known to the skilled artisan (WO 00/61186).

The term "estrogen receptor modulators" in the course of the present invention refers to compounds that interfere with or inhibit the binding of estrogen to estrogen receptor—independently from the mode of action. Non-limiting examples of estrogen receptor modulators are tamoxifen, raloxifen, idoxifen, LY353381, LY 117081, toremifen, fulvestrant, 4-[7-(2,2-Dimethyl-1-oxopropoxy-4-methyl-2-[4-[2-(1-piperidinyl)ethoxy]phenyl]-2H-1-benzopyran-3-yl]phenyl-2,2-dimethyl-propanoate, 4,4'-Dihydroxybenzophenon-2,4-dinitrophenylhydrazone and SH646.

The term "androgen receptor modulators" in the course of the present invention refers to compounds that interfere with or inhibit the binding of androgens to androgen receptor—independently from the mode of action. Non-limiting examples of androgen receptor modulators are finasteride and other 5alpha-reductase inhibitors, nilutamide, flutamide, bicalutamide, liarozole and abirateron acetate.

The term "retinoid receptor modulators" in the course of the present invention refers to compounds that interfere with or inhibit the binding of retinoids to retinoid receptor—independently from the mode of action. Non-limiting examples of retinoid receptor modulators are bexaroten, tretinoin, 13-cis-retinoic acid, 9-cis-retinoic acid, alpha-difluoromethylornithine, ILX23-7553, trans-N-(4'-Hydroxyphenyl)retinamide and N-4-carboxyphenylretinamide.

The term "cytotoxics" in the course of the present invention refers to compounds that primarily trigger cell death through direct action on cell function(s) or which interfere with or inhibit cell myosis, such as alkylating agents, tumor necrosis factors, intercalating agents, microtubule inhibitors and topoisomerase inhibitors. Non-limiting examples of cytotoxics are tirapazimin, sertenef, cachectine, ifosfamide, tasonermine, lonidamine, carboplatin, altretamine, prednimustine, dibromodulcit, ranimustine, fotemustine, nedaplatin, oxaliplatin, temozolomide, heptaplatin, estramustin, improsulfantosylate, trofosfamide, nimustine, dibrospidium-chloride, pumitepa, lobaplatin, satraplatin, profiromycin, cisplatin, irofulven, dexifosfamide, cis-amindichloro(2-methylpyridine)platin, benzylguanine, glufosfamide, GPX100, (trans, trans,trans)-bis-mu-(hexane-1,6-diamine)-mu-[diamine-platin(II)]bis-[diamine(chloro)platin(II)]-tetrachloride, diarizidinylspermine, arsenium trioxide, 1-(11-Dodecylamino-10-hydroxyundecyl)-3,7-dimethylxanthine, zorubicin, idarubicin, daunorubicin, bisantren, mitoxantron, pirarubicin, pinafide, valrubicine, amrubicine, antineoplaston, 3'-desamino-3'-morpholino-13-desoxo-10-hydroxycaminomycin, annamycin, galarubicin, elinafide, MEN10755 and 4-desmethoxy-3-desamino-3-aziridinyl-4-methylsulfonyl-daunorubicin (WO 00/50032).

Non-limiting examples of microtubule inhibitors are paclitaxel, vindesine-sulfate, 3',4'-dideshydro-4'-desoxy-8'-norv-incaleukoblastine, docetaxol, rhizoxine, dolastatine, mivobuline-isethionate, auristatine, cemadotine, RPR109881, BMS184476, vinflunine, cryptophycine, 2,3,4,5,6-pentafluoro-N-(3-fluoro-4-methoxyphenyl)-benzenesulfonamide, anhydrovinblastine, N,N-dimethyl-L-valyl-L-valyl-N-methyl-L-valyl-L-prolyl-L-proline-t-butylamide, TDX258 and BMS188797.

Non-limiting examples of topoisomerase inhibitors are topotecane, hycaptamine, irinotecane, rubitecane, 6-ethoxypropionyl-3',4'-O-exo-benzylidene-chartreusine, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo-[de]-pyrano-[3',4':b,7] indolizino[1,2b]quiinoline-10,13(9H,15H)-dione, lurtotecane, 7-[2-(N-isopropylamino)ethyl]-(20S)camptothecine, BNP1350, BNPI1100, BN80915, BN80942, etoposide-phosphate, teniposide, sobuzoxane, 2'-dimethylamino-2'-desoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',': 6,7)naphtho(2,3-d)-1,3-dioxol-6-one, 2,3-(methylendioxy)-5-methyl-7-hydroxy-8-methoxybenzo[c]phenanthridinium, 6,9-bis[(2-aminoethyl)amino]-benzo[g]isoquinoline-5,10-dione, 5-(3-aminopropylamino)-7,10-dihydroxy-2-(2-hydroxyethylaminomethyl)-6H-pyrazolo[4,5,1-de]-acridine-6-one, N-[1-[2(diethylamino)ethylamino]-7-methoxy-9-oxo-9H-thioxane-then-4-ylmethyl] formamide, N-(2-(dimethyl-amino)-ethyl)acridine-4-carboxamide, 6-[[2-(dimethylamino)-ethyl]amino]-3-hydroxy-7H-indeno[2,1-c]quinolin-7-one and dimesna.

Non-limiting examples of antiproliferative agents are antisense RNA- and antisense-DNA oligonucleotides, such as G3139, ODN698, RVASKRAS, GEM231 and INX3001, as well as antimetabolites such as enocitabine, carmofur, tegafur, pentostatine, doxifluridine, trimetrexate, fludarabine, capecitabine, galocitabine, cytarabin-ocfosfate, fosteabine sodiumhydrate, raltitrexed, paltitrexide, emitefur, tiazofurine, decitabine, nolatrexed, pemetrexed, nelzarabine, 2'-desoxy-2'-methylidencytidine, 2'-fluoromethylen-2'-desoxycytidine, N-[5-(2,3-dihydrobenzofuryl)sulfonyl]-N'-(3,4-dichlorophenyl)urea, N6-[4-desoxy-4-[N2-[2(E),4(E)-tetradecadienoyl]glycylamino]-L-glycero-B-L-manno-heptopyranosyl]adenine, aplidine, ecteinascidine, troxacitabine, 4-[2-amino-4-oxo-4,6,7,8-tetrahydro-3H-pyrimidino[5,4-b][1,4]thiazine-6-yl-(S)-ethyl]-2,5-thienoyl-L-glutaminic acid, aminopterine, 5-fluorouracil, alanosine, 11-acetyl-8-(carbamoyloxymethyl)-4-formyl-6-methoxy-14-oxa-1,11-diaza-tetracyclo-(7.4.1.0.0)-tetradeca-2,4,6-trien-9-ylacetic acid ester, swainsonine, lometrexole, dexrazoxane, methioninase, 2'-cyan-2'-desoxy-N4-palmitoyl-1-B-D-arabinofuranosylcytosine and 3-aminopyridine-2-carboxaldehyde-thiosemicarbazone.

"Antiproliferative agents" also comprises monoclonal antibodies against growth factors that have not been listed under "angiogenesis inhibitors", such as trastuzumab, as well as tumor suppressor genes, such as p53.

In another aspect of the invention, a medicament according to above aspects and embodiments is provided, wherein in such medicament comprises at least one additional pharmacologically active substance (drug, ingredient).

In a preferred embodiment the at least one pharmacologically active substance is a substance as described herein.

In another aspect of the invention, a medicament according to above aspects and embodiments is provided, wherein the medicament is applied before and/or during and/or after treatment with at least one additional pharmacologically active substance.

In a preferred embodiment the at least one pharmacologically active substance is a substance as described herein.

In another aspect of the invention, a pharmaceutical composition comprising a therapeutically effective amount of at least one compound of the invention is provided.

In a preferred embodiment, the pharmaceutical composition contains at least one additional compound selected from the group consisting of physiologically acceptable excipients, auxiliaries, adjuvants, diluents, carriers and/or additional pharmaceutically active substance other than the compounds of the invention.

In another aspect of the invention, a pharmaceutical composition is disclosed which comprises at least one compound of the invention, at least one pharmacologically active substance other than the compounds of the invention as described herein; and a pharmaceutically acceptable carrier.

A further embodiment of the present invention is a process for the manufacture of said pharmaceutical compositions, characterized in that one or more compounds according to the invention and one or more compounds selected from the group consisting of solid, liquid or semiliquid excipients, auxiliaries, adjuvants, diluents, carriers and pharmaceutically active agents other than the compounds according to the invention, are converted in a suitable dosage form.

In another aspect of the invention, a kit is provided comprising a therapeutically effective amount of at least one compound of the invention and/or at least one pharmaceutical composition as described herein and a therapeutically effective amount of at least one further pharmacologically active substance other than the compounds of the invention.

The pharmaceutical compositions of the present invention may be administered by any means that achieve their intended purpose. For example, administration may be by oral, parenteral, topical, enteral, intravenous, intramuscular, inhalant, nasal, intraarticular, intraspinal, transtracheal, transocular, subcutaneous, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below:

tablets: mixing of active ingredient/s and auxiliaries, compression of said mixture into tablets (direct compression), optionally granulation of part of mixture before compression.

capsules: mixing of active ingredient/s and auxiliaries to obtain a flowable powder, optionally granulating powder, filling powders/granulate into opened capsules, capping of capsules.

semi-solids (ointments, gels, creams): dissolving/dispersing active ingredient/s in an aqueous or fatty carrier; subsequent mixing of aqueous/fatty phase with complementary fatty/aqueous phase, homogenization (creams only).

suppositories (rectal and vaginal): dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms.

aerosols: dispersing/dissolving active agent/s in a propellant, bottling said mixture into an atomizer.

In general, non-chemical routes for the production of pharmaceutical compositions and/or pharmaceutical preparations comprise processing steps on suitable mechanical means known in the art that transfer one or more compounds of the invention into a dosage form suitable for administration to a patient in need of such a treatment. Usually, the transfer of one or more compounds of the invention into such a dosage form comprises the addition of one or more compounds, selected from the group consisting of carriers, excipients, auxiliaries and pharmaceutical active ingredients other than the compounds of the invention. Suitable processing steps include, but are not limited to combining, milling, mixing, granulating, dissolving, dispersing, homogenizing, casting and/or compressing the respective active and non-active ingredients. Mechanical means for performing said processing steps are known in the art, for example from Ullmann's Encyclopedia of Industrial Chemistry, 5th Edition. In this respect, active ingredients are preferably at least one compound of the invention and one or more additional compounds other than the compounds of the invention, which show valuable pharmaceutical properties, preferably those pharmaceutical active agents other than the compounds of the invention, which are disclosed herein.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The compounds of the invention may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

Suitable excipients are organic or inorganic substances, which are suitable for enteral (for example oral), parenteral or topical administration and do not react with the compounds of the invention, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropylmethylcellulose, sodium carboxymethylcellulose, polyvinyl pyrrolidone and/or vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices or to provide a dosage form affording the advantage of prolonged action, the tablet, dragee or pill can comprise an inner dosage and an outer dosage component me latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropylmethyl-cellulose phthalate, are used. Dye stuffs or pigments may be added to the tablets or dragee coatings, for example, for identification or in order to characterize combinations of active compound doses.

Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The compounds of the invention can also be lyophilized and the lyophilizates obtained can be used, for example, for the production of injection preparations.

The preparations indicated can be sterilized and/or can contain excipients such as lubricants, preservatives, stabilizers and/or wetting agents, emulsifiers, salts for affecting the osmotic pressure, buffer substances, colorants, flavourings and/or aromatizers. They can, if desired, also contain one or more further active compounds, e.g. one or more vitamins.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatine.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400).

Aqueous injection suspensions may contain substances, which increase the viscosity of the suspension, including, for example, sodium carboxymethyl cellulose, sorbitol, and/or dextran, optionally, the suspension may also contain stabilizers.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

Possible pharmaceutical preparations, which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatine rectal capsules, which consist of a combination of the active compounds with a base. Possible base materials include, for example, liquid triglycerides, polyethylene glycols, or paraffin hydrocarbons.

For use in medicine, the compounds of the present invention will be in the form of pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic bases, e.g. quaternary ammonium salts.

The pharmaceutical preparations can be employed as medicaments in human and veterinary medicine. As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount"means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Said therapeutic effective amount of one or more of the compounds of the invention is known to the skilled artisan or can be easily determined by standard methods known in the art.

The compounds of the invention and the additional active substances are generally administered analogously to commercial preparations. Usually, suitable doses that are therapeutically effective lie in the range between 0.0005 mg and 1000 mg, preferably between 0.005 mg and 500 mg and especially between 0.5 mg and 100 mg per dose unit. The daily dose is preferably between about 0.001 mg/kg and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For the purpose of the present invention, all mammalian species are regarded as being comprised. In a preferred embodiment, such mammals are selected from the group consisting of "primate, human, rodent, equine, bovine, canine, feline, domestic animals, cattle, livestock, pets, cow, sheep, pig, goat, horse, pony, donkey, hinny, mule, hare, rabbit, cat, dog, guinea pig, hamster, rat, mouse". More preferably, such mammals are humans. Animal models are of interest for experimental investigations, providing a model for treatment of human diseases.

The specific dose for the individual patient depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

In the case of many disorders, the susceptibility of a particular cell to treatment with the subject compounds may be determined by in vitro testing. Typically a culture of the cell is combined with a subject compound at varying concentrations for a period of time sufficient to allow the active agents to show a relevant reaction, usually between about one hour and one week. For in vitro testing, cultured cells from a biopsy sample may be used.

Even without further details, it is assumed that a person skilled in the art will be able to utilise the above description in the broadest scope. The preferred embodiments should therefore merely be regarded as descriptive disclosure, which is absolutely not limiting in any way.

Above and below, all temperatures are indicated in ° C. In the following examples, "conventional work-up" means that, if necessary, the solvent is removed, water is added if necessary, the pH is adjusted, if necessary, to between 2 and 10, depending on the constitution of the end product, the mixture is extracted with ethyl acetate or dichloromethane, the phases are separated, the organic phase is washed with saturated $NaHCO_3$ solution, if desired with water and saturated NaCl solution, is dried over sodium sulfate, filtered and evaporated, and the product is purified by chromatography on silica gel, by preparative HPLC and/or by crystallisation. The purified compounds are, if desired, freeze-dried.

Mass spectrometry (MS): ESI (electrospray ionisation) $(M+H)^+$

67
List of Abbreviations and Acronyms

AcOH acetic acid, anh anhydrous, atm atmosphere(s), BOC tert-butoxycarbonyl CDI 1,1'-carbonyl diimidazole, conc concentrated, d day(s), dec decomposition, DMAC N,N-dimethylacetamide, DMPU 1,3-dimethyl-3,4,5,6-tetrahydro-2(IH)-pyrimidinone, DMF NN-dimethylformamide, DMSO dimethylsulfoxide, DPPA diphenylphosphoryl azide, EDCI 1-(3-dimethylaminopropyl)-3-ethylcarbodiimide, EtOAc ethyl acetate, EtOH ethanol (100%), Et$_2$O diethyl ether, Et$_3$N triethylamine, h hour(s), MeOH methanol, pet. ether petroleum ether (boiling range 30-60° C.), temp. temperature, THF tetrahydrofuran, TFA trifluoroAcOH, Tf trifluoromethanesulfonyl.

The contents of all cited references are hereby incorporated by reference in their entirety. The invention is explained in more detail by means of the following examples without, however, being restricted thereto.

EXAMPLES

I. Synthesis of Selected Compounds of the Invention

The following compounds were synthesized and characterized. However, it lies in the knowledge of a person skilled in the art to prepare and characterize these compounds differently.

Example 1

Synthesis of 6-(1H-Benzotriazole-5-carbonyl)-2-[3-(4-chloro-phenyl)-ureido]-4,5,6,7-tetrahydro-thieno[2,3-c]pyridine-3-carboxylic acid amide 6

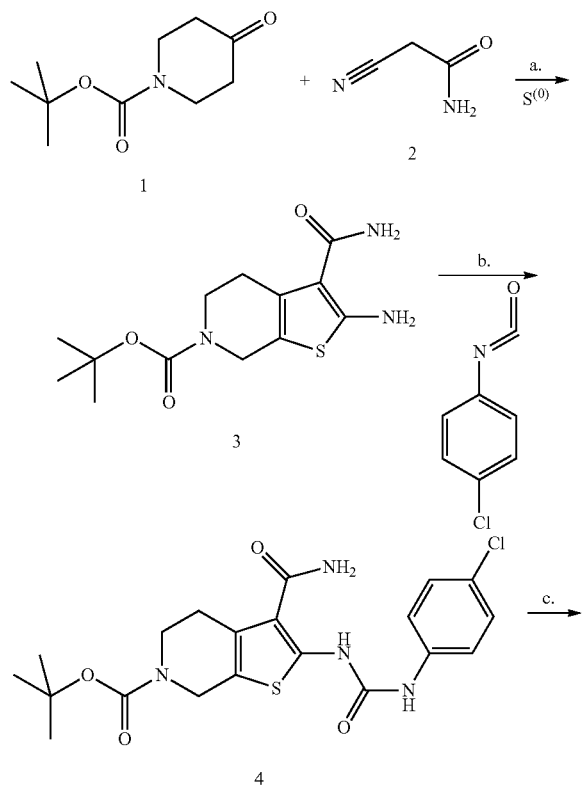

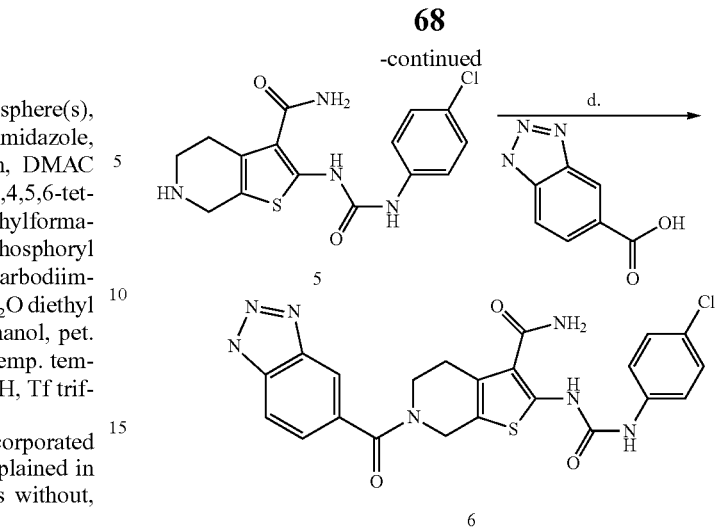

a. Synthesis of 2-Amino-3-carbamoyl-4,7-dihydro-5H-thieno[2,3-c]pyridine-6-carboxylic acid tert-butyl ester (3)

Starting material 1 (25 g, 125 mmol) was suspended in a 250 ml bowl flask in 125 ml abs. ethanol and mixed with starting material 2 (10.5 g, 125 mmol) and sulfur (4.023 g, 125 mmol). 12.9 ml (125 mmol) diethyl amine was added dropwise to the yellow suspension, which thereby became of orange color. The reaction mixture was stirred over night at ambient temperature. Next day, the reddish solution was concentrated in vacuo and the crude product was re-crystallized in methanol. The desired product 3 was isolated as a red-brown solid (40.7 g, 116 mmol, 93%).

b. Synthesis of 3-Carbamoyl-2-[3-(4-chloro-phenyl)-ureido]-4,7-dihydro-5H-thieno[2,3-c]pyridine-6-carboxylic acid tert-butyl ester (4)

Compound 3 (1.5 g, 4.3 mmol) and p-Chlorphenylisocyanat (724 mg, 4.7 mmol) were dissolved in pyridine (12 ml) and stirred over night at room temperature. Another equivalent of isocyanate (724 mg, 4.7 mmol) was added and the mixture was stirred over the weekend. The solvent was reduced under vacuum and the crude product (2.3 g, 4 mmol; light brown solid) was used in the next reaction without further purification (Content: 79% compound 4 according to UV).

c. Synthesis of 2-[3-(4-Chloro-phenyl)-ureido]-4,5,6,7-tetrahydro-thieno[2,3-c]pyridine-3-carboxylic acid amide (5)

Starting material 4 (2.3 g, 4.1 mmol) was suspended in 20 ml DCM and mixed with trifluoro acetic acid (TFA, 7.9 ml, 102 mmol). The resulting brown solution was stirred at room temperature for 50 Min. the solvent was reduced in vacuo and the crude product was purified by prep. HPLC (Method 1).

The product fraction were merged and the solvent was reduced and the product finally lyophilized yielding 5 (850 mg, 2.4 mmol, 59%) as a light brown solid.

d. Synthesis of 6-(1H-Benzotriazole-5-carbonyl)-2-[3-(4-chloro-phenyl)-ureido]-4,5,6,7-tetrahydro-thieno[2,3-c]pyridine-3-carboxylic acid amide (6)

Starting material 5 (847 mg, 2.4 mmol) was suspended in DMF (8 ml) and 1H-1,2,3-benzothiazole-5-carboxyllic acid (473 mg, 2.9 mmol), dry HOBt (427 mg, 2.9 mmol) and EDCI (606 mg, 2.9 mmol) were added. The brown suspension was stirred at ambient temperature over the weekend. As the reaction was not complete yet, the reaction was further stirred at 80° for 4 h. Thereby a brown solution was formed. The solvent was evaporated in vacuo and the crude product was further purified by prep. HPLC (Method 1). The product fractions were merged, the solvent was evaporated and the product lyophilized. Thereby 310 mg of the desired product 6 (0.635 mmol, 28%) were isolated as a light brown solid and additional 58 mg of the same product with 76% content which could have been purified further.

As an alternative, 5 can be prepared by using an alloc-protected starting material instead of the BOC-protected one:

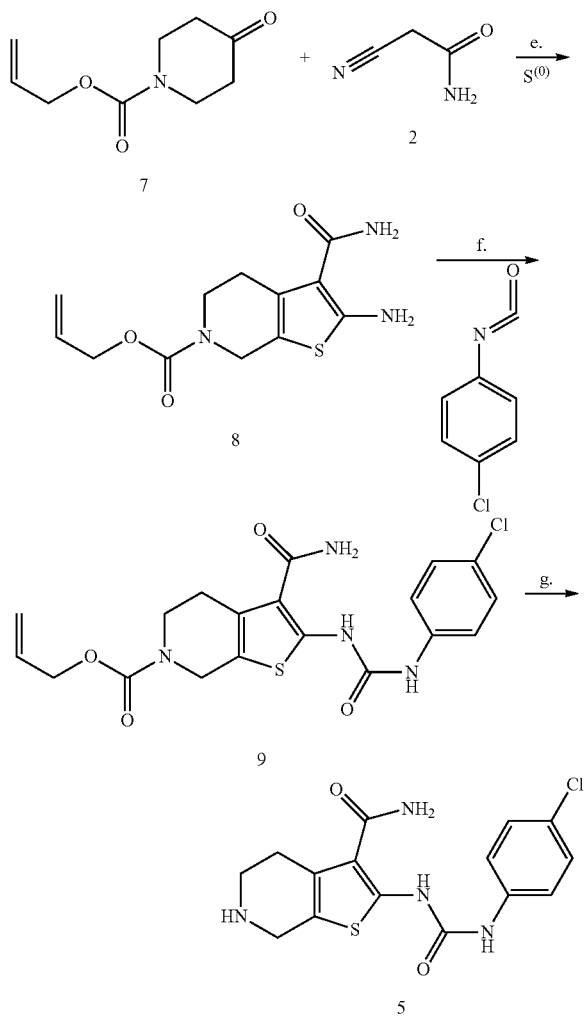

e. Synthesis of 2-amino-3-carbamoyl-4,7-dihydro-5H-thieno[2,3-c]pyridine-6-carboxylic acid allyl ester (8)

Starting materials 7 (4 g, 22 mmol), 2 (1.8 g, 22 mmol) and sulfur (700 mg, 22 mmol) were weighed into a bowl flask and 16 ml of ethanol were added. Diethyl amine (2.2 ml, 22 mmol) was added dropwise to the yellow suspension. The reaction was stirred over night. The orange colored precipitate was filtered off and identified as the product 8 (4 g, 11.8 mmol, 83% content, 54% yield) which could be used without further purification.

f. Synthesis of 3-Carbamoyl-2-[3-(4-chloro-phenyl)-ureido]-4,7-dihydro-5H-thieno[2,3-c]pyridine-6-carboxylic acid allyl ester (9)

Starting material 8 (1 g, 3.6 mmol) was dissolved in 12 ml of pyridine and p-chlorphenyl isocyanate (546 mg, 3.6 mmol) was added. The red solution was stirred over the weekend. The solvent was reduced in a vacuum centrifuge. The crude product was used without further purification (green-brown solid, 1.13 g, 65% content 9, 46% yield).

g. Synthesis of 2-[3-(4-Chloro-phenyl)-ureido]-4,5,6,7-tetrahydro-thieno[2,3-c]pyridine-3-carboxylic acid amide (5)

Starting material 9 (750 mg, 1.7 mmol) was dissolved under Nitrogen atmosphere in 10 ml DCM in a 2 necked flask and a solution of morpholine (3 ml, 34.5 mmol) in 34.5 ml DCM was added. The solution was stirred for 5 Min. then a solution of Tetrakis(triphenylphosphin)-palladium(0) (199 mg, 0.2 mmol) in 17.2 ml DCM was added. After about 8 Min a brown suspension was formed. The reaction was stirred at ambient temperature for another 40 Min. The solvent was then reduced and product 5 was thereby isolated in two fractions: very pure as white crystals (246 mg, 0.7 mmol, 41%) and with 56% content in a brown solid (250 mg, 56% Gehalt an 5, 0.4 mmol), which contained side products as well but could be purified by prep. HPLC (Method 2). The pure product fractions were merged, the solvent reduced and the product lyophilized.

As an alternative, as exemplified in example 2, the final products can be prepared without the use of any protecting group:

Example 2

Synthesis of 1-[6-(1H-Benzotriazole-5-carbonyl)-3-(pyrrolidine-1-carbonyl)-4,5,6,7-tetrahydro-thieno[2,3-c]pyridin-2-yl]-3-(4-chloro-phenyl)-urea (14)

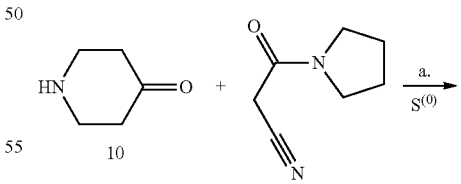

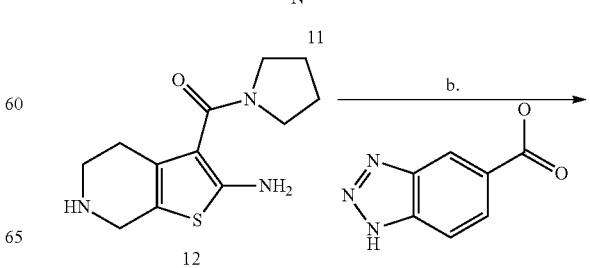

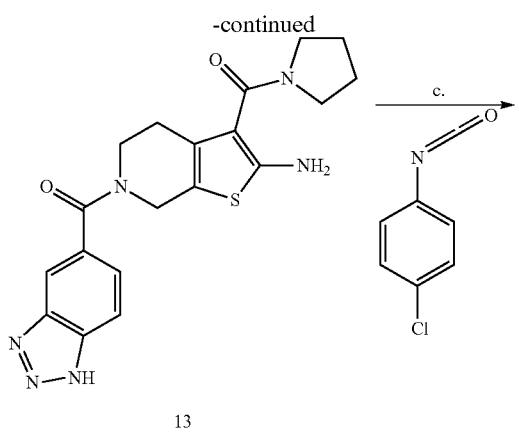

13

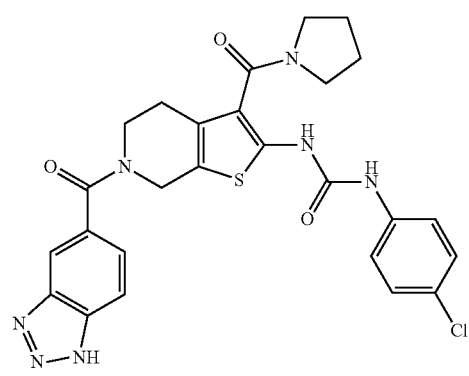

14 a. Synthesis of (2-Amino-4,5,6,7-tetrahydro-thieno[2,3-c]pyridin-3-yl)-pyrrolidin-1-yl-methanone (12)

In a 100 ml bowl flask with dropping funnel, pyridon-(4) (starting material 10, 1 g, 10.1 mmol) was dissolved in 50 ml abs. ethanol. Then starting material 11 (1.4 g, 10.1 mmol) and sulfur (0.3 g, 10.1 mmol) were added. 2 ml diethyl amine (20.2 mmol) were added dropwise to the yellow suspension (over 20 Min) resulting in a brown solution. The reaction was stirred at room temperature over night. Another ml of Diethyl amine (10.1 mmol) was added and the reaction was stirred for another 7 h. The reaction was concentrated in vacuo. Thereby the desired product 12 was isolated as a viscous brown matter (3.2 g, 75% content of 12, 95% yield), which could be used without further purification.

b. Synthesis of [2-Amino-6-(1H-benzotriazole-5-carbonyl)-4,5,6,7-tetrahydro-thieno[2,3-c]pyridin-3-yl]-pyrrolidin-1-yl-methanone (13)

Starting material 12 (1.6 g, 6.4 mmol) was dissolved in 20 ml DMF. Then EDCI (1.46 g, 7.6 mmol) and HOBt (1.3 g, 9.5 mmol) were added. Now, one half of 1.04 g (6.4 mmol) 1H-1,2,3-benzothiazole-5-carboxyllic acid was added. The reaction mixture was stirred at ambient temperature over night. Then the other half of the 1H-1,2,3-benzothiazole-5- carboxyllic acid was added and the reaction mixture was again stirred at ambient temperature over night. The reaction mixture was now concentrated in vacuo yielding 7 g crude product. Those were taken up in ethyl acetate and water and the phases were separated. The organic phase was washed with water and the combined aqueous phases were washed with ethyl acetate. The combined organic phases were washed with brine, dried over MgSO$_4$ and concentrated in vacuo. The desired product 13 was isolated as a brown oil (1.2 g, 20% content, 10% yield).

c. Synthesis of 1-[6-(1H-Benzotriazole-5-carbonyl)-3-(pyrrolidine-1-carbonyl)-4,5,6,7-tetrahydro-thieno[2,3-c]pyridin-2-yl]-3-(4-chloro-phenyl)-urea (14)

Starting material 13 (1.2 g, 20% content, 0.6 mmol) was dissolved in 5 ml pyridine and one half of 112 mg (0.7 mmol) p-chlorphenyl isocyanate was added. The reaction mixture was stirred over night at ambient temperature. Then the other half of the p-chlorphenyl isocyanate was added and the reaction was again stirred over night at ambient temperature. The reaction was now concentrated in vacuo and the thereby isolated crude product was dissolved in 7 ml DMSO and purified by prep. HPLC (Method 3). The pure fractions were combined, the solvent reduced and the product finally lyophilized. The desired product 14 could thereby be isolated as yellow solid (16.2 mg, 4%; and additional 17 mg, 84% content 14, 4% yield).

In analogy to example 2-a, pyridon(4)-hydrochloride (15) was reacted with cyano-acetic acid methyl ester (16):

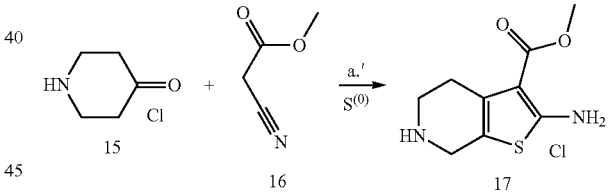

a.' Synthesis of 2-Amino-4,5,6,7-tetrahydro-thieno[2,3-c]pyridine-3-carboxylic acid methyl ester hydrochloride (17)

Piperidone-(4), hydrochloride (15, 154 g, 1.1 mol), Methyl-cyanacetat (16, 84 g, 0.8 mol) and sulfur (32 g, 1 mol) were suspended in 500 ml methanol. Then diethyl amine (150 ml, 1.4 mol) was added. The mixture was stirred at room temperature for 5 h. The resulting crystals were filtered, washed with a mixture of iso-propanol and methanol and dried. The mother liquor was reduced to 50% volume in vacuo and left over night. The resulting crystals were again filtered, washed with iso-propanol and dried. In total 133 g of the desired product 17 (0.54 mol, 47%) were isolated, characterized by NMR and further used in reactions in analogy to 12.

Instead of ureas also amides were synthesized:

Example 3

Synthesis of 6-(1H-Benzotriazole-5-carbonyl)-2-[2-(4-chloro-2-fluoro-phenyl)-acetylamino]-4,5,6,7-tetrahydro-thieno[2,3-c]pyridine-3-carboxylic acid amide

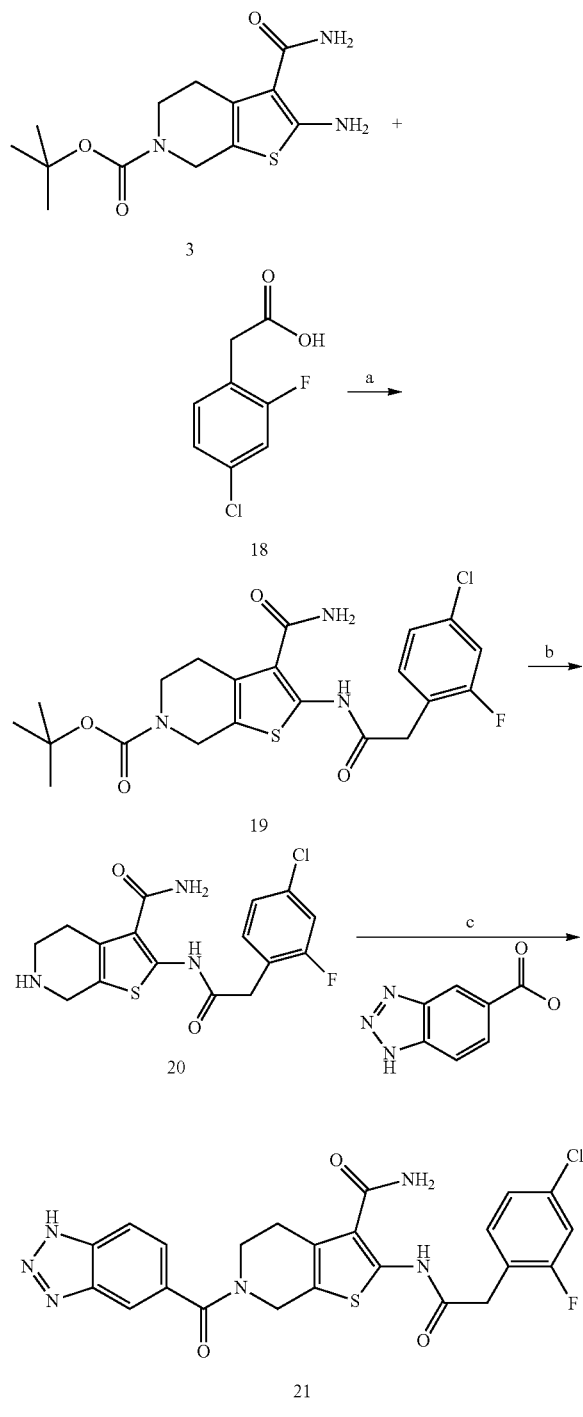

a. Synthesis of 3-Carbamoyl-2-[2-(4-chloro-2-fluoro-phenyl)-acetylamino]-4,7-dihydro-5H-thieno[2,3-c]pyridine-6-carboxylic acid tert-butyl ester (19)

Starting material 3 (1 g, 2.9 mmol) was suspended in 11 ml DMF and starting material 18 (593 mg, 3.1 mmol), dry HOBt (505 mg, 3.1 mmol) and EDCI (657 mg, 3.4 mmol) were added. The brown suspension was stirred over the weekend at ambient temperature then the reaction was heated to 80° C. over night. The solvent was reduced in the vacuum centrifuge and the crude product (a brown oil) was used without further purification (3.2 g, 22% content 19, 53% yield).

b. Synthesis of 2-[2-(4-Chloro-2-fluoro-phenyl)-acetylamino]-4,5,6,7-tetrahydro-thieno[2,3-c]pyridine-3-carboxylic acid amide (20)

Starting material 19 (3.2 g, 22% content, 1.5 mmol) was dissolved in 25 ml dried DCM and trifluoro acetic acid (TFA, 8.0 ml, 104 mmol) was added. The reaction was stirred at ambient temperature for 30 Min. The solvent was reduced in vacuo and the crude product was purified at the Flashmaster (Method 1). The isolated product was not sufficiently pure and was therefore purified again at the prep. HPLC (Method 4). The pure fractions were combined and the solvent was reduced. The desired product 20 was thereby isolated as a brown solid (236 mg, 42%).

c. Synthesis of 6-(1H-Benzotriazole-5-carbonyl)-2-[2-(4-chloro-2-fluoro-phenyl)-acetylamino]-4,5,6,7-tetrahydro-thieno[2,3-c]pyridine-3-carboxylic acid amide (21)

Starting material 20 (118 mg, 0.3 mmol) was suspended in 2 ml dry DMF and 1H-1,2,3-benzothiazole-5-carboxyllic acid (63 mg, 0.4 mmol, 1.2 equiv.), dry HOBt (52 mg, 0.4 mmol) and EDCI (74 mg, 0.4 mmol) were added. The brown suspension was stirred at 80° C. over night. Then another 0.5 equiv. 1H-1,2,3-benzothiazole-5-carboxyllic acid were added and the reaction was stirred another 6 h at 80° C. the solvent was reduced under vacuo and the remaining crude product further purified by prep. HPLC (Method 3). The pure fractions were combined and the solvent was reduced. The remaining product was lyophilized yielding the desired products 21 as a light-brown solid (20 mg, 0.04 mmol, 12%).

Analogously, instead of making amides with 1H-1,2,3-benzothiazole-5-carboxylic acid other substituents were introduced as well:

Example 4

Synthesis of 2-[2-(4-Chloro-2-fluoro-phenyl)-acetylamino]-6-pyridin-4-ylmethyl-4,5,6,7-tetrahydro-thieno[2,3-c]pyridine-3-carboxylic acid amide (23)

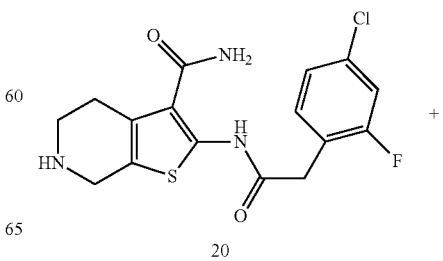

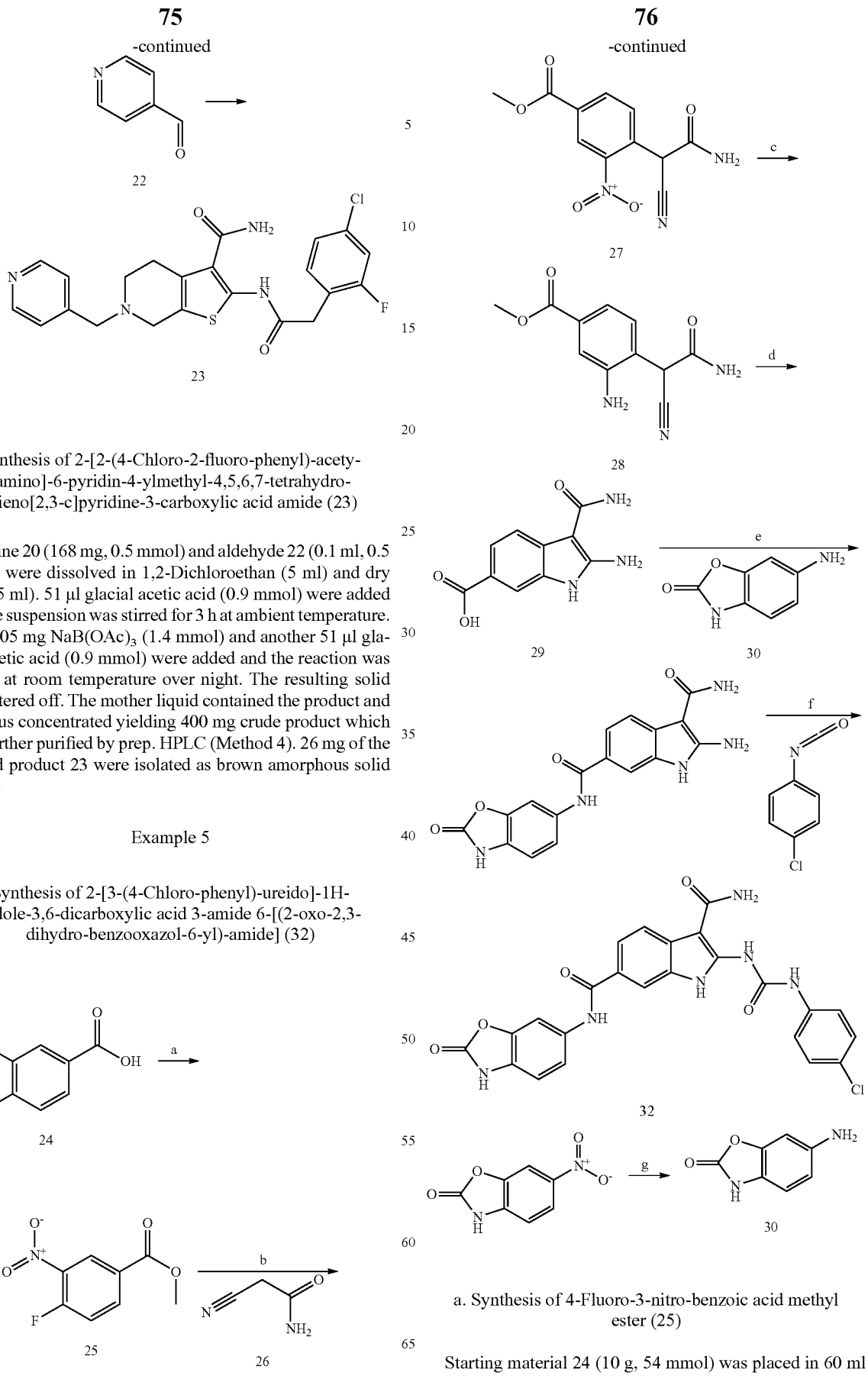

Synthesis of 2-[2-(4-Chloro-2-fluoro-phenyl)-acetylamino]-6-pyridin-4-ylmethyl-4,5,6,7-tetrahydro-thieno[2,3-c]pyridine-3-carboxylic acid amide (23)

Amine 20 (168 mg, 0.5 mmol) and aldehyde 22 (0.1 ml, 0.5 mmol) were dissolved in 1,2-Dichloroethan (5 ml) and dry THF (5 ml). 51 µl glacial acetic acid (0.9 mmol) were added and the suspension was stirred for 3 h at ambient temperature. Now 305 mg NaB(OAc)$_3$ (1.4 mmol) and another 51 µl glacial acetic acid (0.9 mmol) were added and the reaction was stirred at room temperature over night. The resulting solid was filtered off. The mother liquid contained the product and was thus concentrated yielding 400 mg crude product which was further purified by prep. HPLC (Method 4). 26 mg of the desired product 23 were isolated as brown amorphous solid (12%).

Example 5

Synthesis of 2-[3-(4-Chloro-phenyl)-ureido]-1H-indole-3,6-dicarboxylic acid 3-amide 6-[(2-oxo-2,3-dihydro-benzooxazol-6-yl)-amide] (32)

a. Synthesis of 4-Fluoro-3-nitro-benzoic acid methyl ester (25)

Starting material 24 (10 g, 54 mmol) was placed in 60 ml methanol and 0.5 ml sulfuric acid was added dropwise. Now the reaction was stirred over night at 80° C. The reaction mixture was then distributed between water and ethyl acetate. The combined organic phases were dried over MgSO$_4$, filtered and concentrated yielding the desired product 25 quantitatively as amorphous solid (10.8 g, 54 mmol).

b. Synthesis of 4-(Carbamoyl-cyano-methyl)-3-nitro-benzoic acid methyl ester (27)

Starting material 25 (10 g, 50 mmol) and cyanacetamide (26, 8.4 g, 100 mmol) were dissolved in dry THF and NaH (60% ig, 4 g, 100 mmol) was added. The reaction was stirred over night at ambient temperature. Now it was cooled to 0° C. and 4 N HCl/Dioxan was added. The reaction mixture was concentrated in vacuo, the solid residue crystallized with 400 ml isopropyl ethyl ether, resulting crystals were filtered and dried. Then the crystals were washed with water and again filtered and dried. Thereby 8.9 g of the desired product 27 (67%, 34 mmol) were isolated.

c. Synthesis of 4-Fluoro-3-amino-benzoic acid methyl ester (28)

Starting material 27 (7 g, 26.6 mmol) was dissolved in 700 ml methanol. The solution was hydrogenated in tow batches in the H-cube (Thales Nanotechnology).
Parameters:
flow rate: 3.0 ml/min
mode full H$_2$
catalyst Raney Nickel THS 01122
T/° C. R.T.
p/bars ambient pressure
The hydrogenated solutions were combined and reduced in vacuo. The product isolated thereby (28, 5.5 g, 23.5 mmol, 89%) was used further without additional purification.

d. Synthesis of 2-Amino-3-carbamoyl-1H-indole-6-carboxylic acid (29)

Starting material 28 (5.5 g, 23.5 mmol) was dissolved in 200 ml abs. THF and 2 N NaOH (45 ml, 90 mmol) was added at room temperature. Upon stirring, the solution got dark and a solid precipitate was formed. The suspension was reduced to about 100 ml and extracted three times with 400 ml ethyl acetate each. The aqueous phase was reduced in vacuo and treated twice with ethyl acetate upon which the desired product 29 was crystallized (1.1 g, 5.5 mmol, 21%).

e. Synthesis of 2-Amino-1H-indole-3,6-dicarboxylic acid 3-amide 6-[(2-oxo-2,3-dihydro-benzooxazol-6-yl)-amide] (31)

Starting material 29 (500 mg, 2.3 mmol) was dissolved in 2 ml dry DMF. Then EDCI (575 mg, 3 mmol) and HOBt (322 mg, 2.4 mmol) were added. The reaction was stirred over night at ambient temperature. Now the reaction mixture was poured into water and the resulting precipitate was filtered and dried. This intermediate was identified to be the HOBT ester of the starting material 29 (645 mg, 1.9 mmol, 84%), which could be used without further purification:

500 mg (1.5 mmol) of the intermediate and 300.3 mg (2 mmol) 6-Amino-3H-benzooxazol-2-one (preparation see below) were dissolved in dry DMF (2 ml). Then 383 mg (2 mmol) EDCI were added and the reaction was stirred at 60° C. over night. Now the solution was added to water and the resulting dark precipitate was filtered and dried yielding 400 mg (0.85 mmol) of the desired product 31 in 43% yield (calculated from the used intermediate).

f. Synthesis of 2-[3-(4-Chloro-phenyl)-ureido]-1H-indole-3,6-dicarboxylic acid 3-amide 6-[(2-oxo-2,3-dihydro-benzooxazol-6-yl)-amide] (32)

Starting material 31 (100 mg, 0.3 mmol) was dissolved in 1 ml dry pyridine. 4-Chlorphenyl isocyanate (46 mg, 0.3 mmol) was then added and the mixture stirred at ambient temperature. Then another 40 mg (0.29 mmol) 4-Chlorphenyl isocyanate were added and the reaction was stirred at 50° C. After a few hours the reaction was reduced in vacuo and purified by prep. HPLC. After concentration of the pure fractions 10 mg (0.02 mmol, 7%) of the desired product 32 were isolated.

g. Synthesis of 6-Amino-3H-benzooxazol-2-one (30)

5 g (26.9 mmol) 6-Nitrobenoxazol-2(3H)-on were dissolved in 100 ml THF and 1 g Pd—C-5% (containing 50.5% water) were added. The reaction was hydrogenated with H2 over 16 h. The reaction mixture was then filtered over celite and reduced in vacuo. Thereby the desired product 30 was isolated as a red-brown solid (2.6 g, 17.4 mmol, 65%).

Example 6

Synthesis of 2-[3-(4-Chloro-phenyl)-ureido]-benzothiazole-6-carboxylic acid (2-oxo-2,3-dihydro-benzooxazol-6-yl)-amide (36)

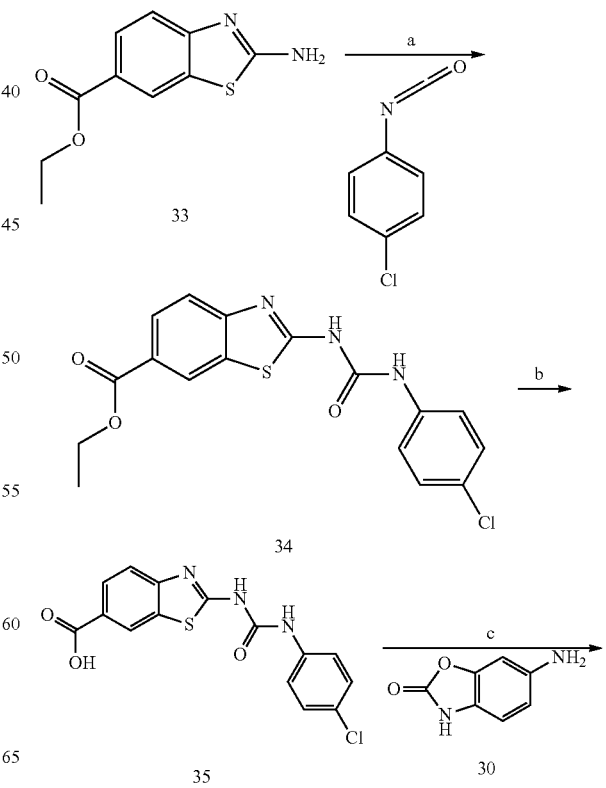

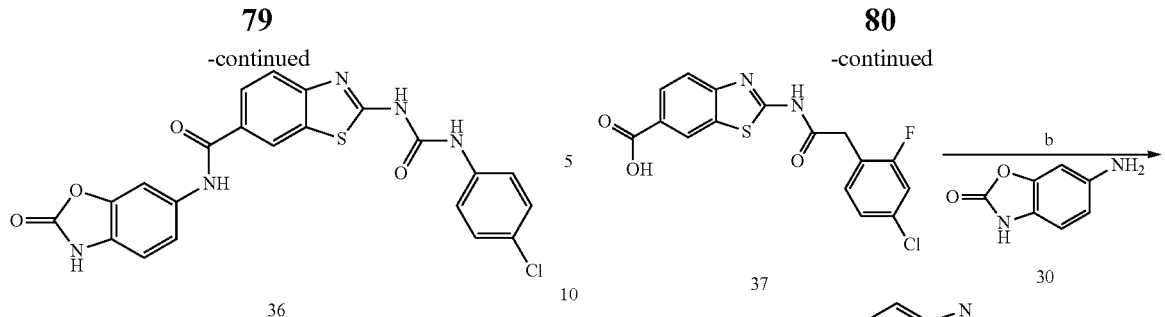

36 a. Synthesis of 2-[3-(4-Chloro-phenyl)-ureido]-benzothiazole-6-carboxylic acid ethyl ester (34)

Starting material 33 (400 mg, 1.8 mmol) was dissolved in dry pyridine (1 ml). 4-Chlorphenylisocyanat (307 mg, 2 mmol) was added and the reaction was stirred at ambient temperature over night. The reaction mixture was then added to 1 N HCl and the resulting precipitate was filtered, washed with water and dried. The desired product 36 was thus isolated (710 mg, 1.58 mmol, 88%).

b. Synthesis of 2-[3-(4-Chloro-phenyl)-ureido]-benzothiazole-6-carboxylic acid (35)

505 mg (4.5 mmol) potassium-tert-butylat was placed in a bowl flask and 90 ml water were added, yielding finely dispersed KOH. Starting material 34 (710 mg, 1.6 mmol) was added to this suspension and the mixture was stirred at ambient temperature. After 3 h the reaction was heated to 60° C. over night. Then 4.5 ml 1 N HCl were added to the suspension and the mixture was concentrated in vacuo yielding a solid. Thereby the desired product 35 was isolated as a mixture with NaCl (800 mg, 45% content, 1.035 mmol, 65% yield) which could be used without further purification.

c. Synthesis of 2-[3-(4-Chloro-phenyl)-ureido]-benzothiazole-6-carboxylic acid (2-oxo-2,3-dihydro-benzooxazol-6-yl)-amide (36)

Starting material 35 (300 mg, 45% content, 0.4 mmol) and 6-Amino-3H-benzooxazol-2-one (30, 58 mg, 0.4 mmol) were dissolved in 2 ml of dry DMF. Then EDCI (96 mg, 0.5 mmol) and HOBt (76 mg, 0.5 mmol) were added. The reaction was stirred at ambient temperature over night. It was then purred into water and the resulting precipitate was filtered. The isolated precipitate was then stirred in 100 ml warm methanol and the non-soluble crystals filtered and washed with methanol. Thereby the desired product 36 (130 mg, 0.271 mmol, 70%) could be isolated.

Example 7

Synthesis of 2-[2-(4-Chloro-2-fluoro-phenyl)-acetylamino]-benzothiazole-6-carboxylic acid (2-oxo-2,3-dihydro-benzooxazol-6-yl)-amide (38)

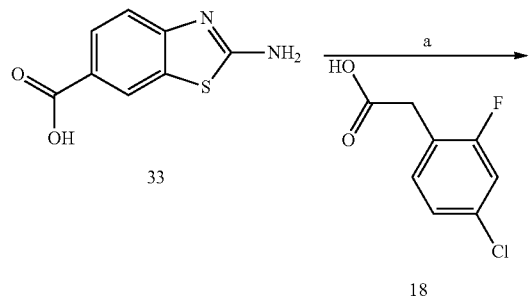

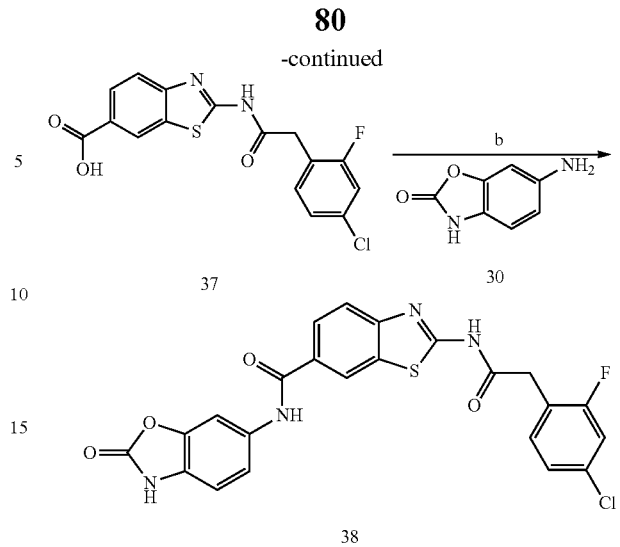

a. Synthesis of 2-[2-(4-Chloro-2-fluoro-phenyl)-acetylamino]-benzothiazole-6-carboxylic acid (37)

Starting material 18 (100 mg, 0.5 mmol) was dissolved in 2 ml DMF. Now EDCI (125 mg, 0.7 mmol) and HOBt (99 mg, 0.7 mmol) were added. After stirring 3 h at room temperature, starting material 33 (103 mg, 0.5 mmol) was added and the reaction was stirred 48 h at room temperature. The solution was poured into 1 N HCl and the resulting precipitate was filtered and dried yielding the desired product 37 (60 mg, 0.2 mmol, 70% content, 31% yield).

b. Synthesis of 2-[2-(4-Chloro-2-fluoro-phenyl)-acetylamino]-benzothiazole-6-carboxylic acid (2-oxo-2,3-dihydro-benzooxazol-6-yl)-amide (38)

Starting material 37 (60 mg, 0.2 mmol, 70% content) and 6-Amino-3H-benzooxazol-2-one (30, 25 mg, 0.2 mmol) were dissolved in 2 ml DMF. Then EDCI (38 mg, 0.2 mmol) and HOBt (31 mg, 0.2 mmol) were added. The reaction was stirred over night at ambient temperature, concentrated in vacuo and purified by prep HPLC (Method 1). By concentration of the pure fractions the desired product 38 (23 mg, 0.04 mmol, 24%) could be isolated.

Example 8

Synthesis of 6-(1H-Benzotriazole-5-carbonyl)-4,5,6,7-tetrahydro-2H-pyrazolo[3,4-c]pyridine-3-carboxylic acid [2-(4-chloro-phenyl)-ethyl]-amide (43)

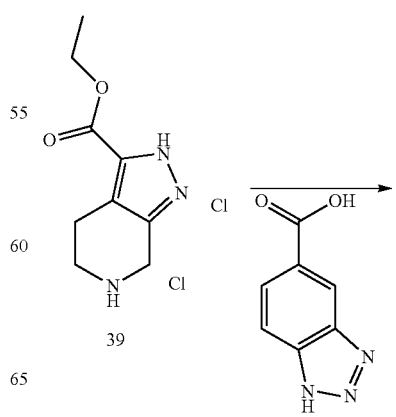

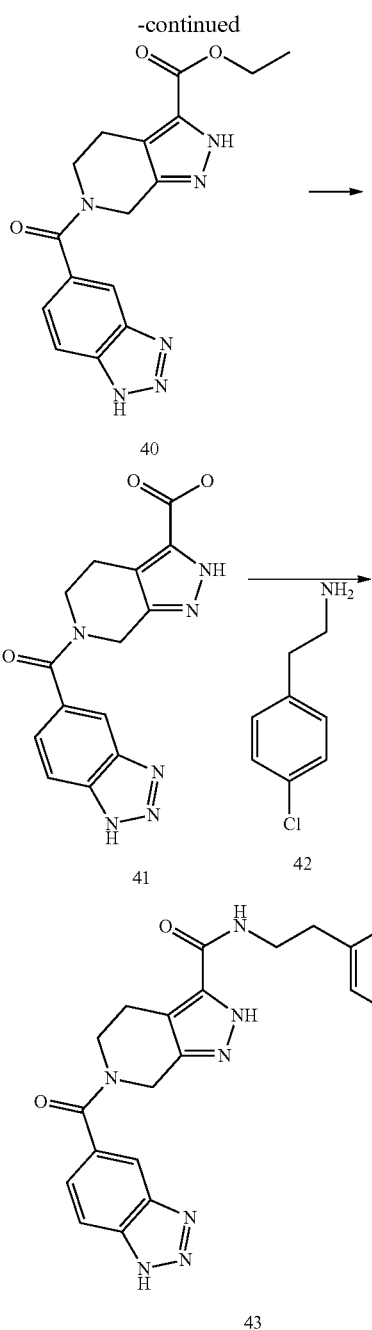

a. Synthesis of 6-(1H-Benzotriazole-5-carbonyl)-4,5,6,7-tetrahydro-2H-pyrazolo[3,4-c]pyridine-3-carboxylic acid ethyl ester (40)

Starting material 39 (1.7 g, 6.4 mmol), 4-methyl morpholine (700 μL, 6.4 mmol) and 1H-1,2,3-benzothiazole-5-carboxyllic acid (1 g, 6.4 mmol) were dissolved in 15 ml DMF. Then EDCI (1.2 g, 6.4 mmol) and HOBt (0.9 g, 6.4 mmol) were added. The reaction was stirred over night at ambient temperature. Then water was added to the reaction mixture and stirring was continued. As no precipitate was formed, ethyl acetate was added and the phases were separated. The aqueous phase was washed twice with ethyl acetate. The combined organic phases were dried over $Na_2SO_4$, filtered and concentrated in vacuo.

The desired product 40 was isolated quantitatively (2.6 g, 6.4 mmol) and further used without purification.

b. Synthesis of 6-(1H-Benzotriazole-5-carbonyl)-4,5,6,7-tetrahydro-2H-pyrazolo[3,4-c]pyridine-3-carboxylic acid (41)

Starting material 40 (2.6 g, 6.4 mmol) was mixed with 2 N NaOH (15 ml) and ethanol (15 ml) and stirred at ambient temperature. Additional 15 ml 2 N NaOH were added. After the reaction was completed, the mixture was reduced to dryness, the solid was dissolved in water, adjusted to pH 2 with 2N HCl and the resulting precipitate was filtered and dried. Thus the desired product 41 (1.4 g, 4.4 mmol, 57%) could be isolated as solid.

c. Synthesis of 6-(1H-Benzotriazole-5-carbonyl)-4,5,6,7-tetrahydro-2H-pyrazolo[3,4-c]pyridine-3-carboxylic acid [2-(4-chloro-phenyl)-ethyl]-amide (43)

Starting material 41 (171.3 mg, 0.5 mmol), 4-Methylmorpholin (60.3 μL, 0.5 mmol) and starting material 42 (85 mg, 0.5 mmol) were dissolved in 5 ml DMF. Then EDCI (105 mg, 0.5 mmol) and HOBt (74 mg, 0.5 mmol) were added. The reaction was stirred over night at ambient temperature.

The reaction mixture was poured into water and the resulting precipitate was filtered off. It was stirred in methyl tert-butyl ether and again filtered. Further purification was done by chromatography with a "Companion" (Method 1).

The pure fractions were concentrated, stirred in methyl tert-butyl ether and filtered. The desired product 43 could thereby be isolated (45.6 mg, 0.1 mmol, 18%).

Example 9

Synthesis of [2-(1H-Benzotriazole-5-carbonyl)-1,2,3,4-tetrahydro-isoquinolin-6-yl]-carbamic acid 3,5-dichloro-benzyl ester (48)

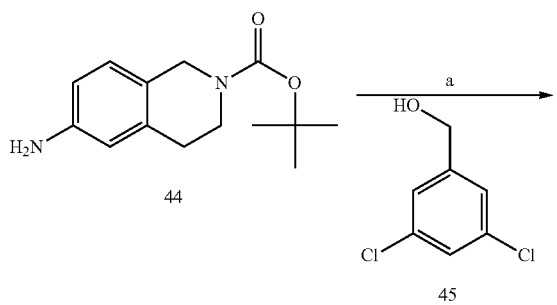

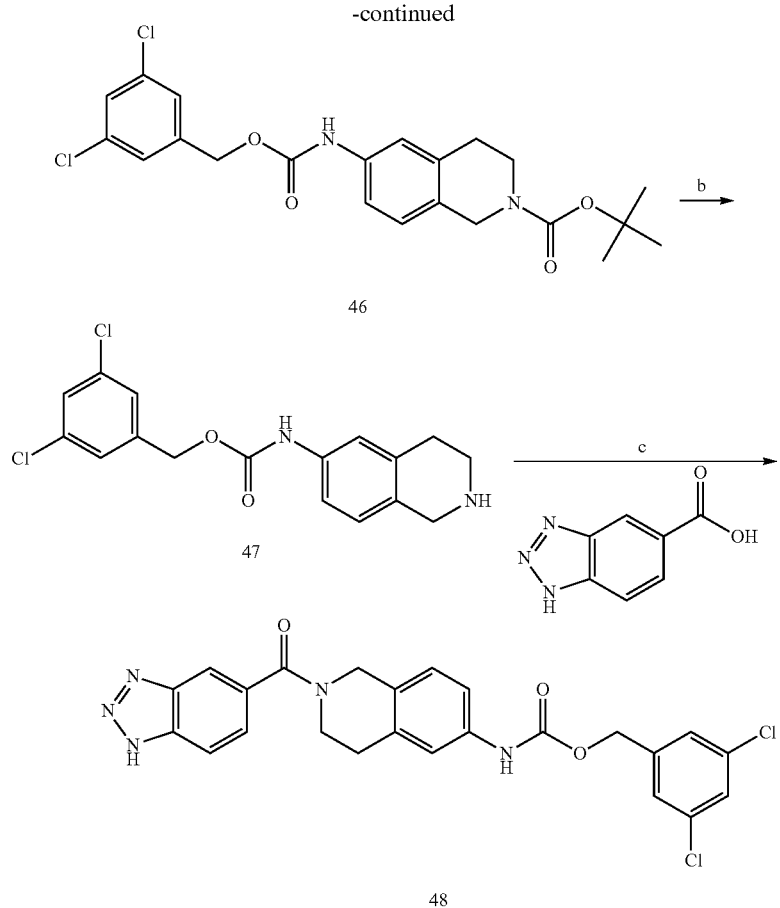

a. Synthesis of 6-(3,5-Dichloro-benzyloxycarbonylamino)-3,4-dihydro-1H-isoquinoline-2-carboxylic acid tert-butyl ester (46)

Starting material 45 (250 mg, 1.4 mmol) and 1,1'-carbonyl diimidazol (275 mg, 1.7 mmol) were dissolved in 2 ml DCM and stirred at room temperature for 3 h. Then starting material 44 (350 mg, 1.4 mmol) was added and the resulting mixture was stirred over night at room temperature. The reaction mixture was diluted with ethyl acetate, the organic phase was washed with water 3 times, dried over $Na_2SO_4$, filtered and concentrated in vacuo. The remaining solid was purified over the prep. HPLC (Method 1), pure fractions were combined and concentrated in vacuo yielding the desired product 46 as brown solid (170 mg, 0.377 mmol, 27%).

b. Synthesis of (1,2,3,4-Tetrahydro-isoquinolin-6-yl)-carbamic acid 3,5-dichloro-benzyl ester (47)

Starting material 46 (170 mg, 0.4 mmol) was dissolved in 5 ml propanol. Then 1 ml HCl in 2-propanol (5-6 N) was added and the mixture was stirred over night at ambient temperature. The reaction mixture was then diluted with diethyl ether, concentrated in vacuo and stirred with diethyl ether, repeatedly decanting. Finally the solid residue was filtered off and dried in vacuo at 45° C. Thus the desired product 47 was isolated as brownish crystals (46 mg, 0.1 mmol, 35%).

c. Synthesis of [2-(1H-Benzotriazole-5-carbonyl)-1,2,3,4-tetrahydro-isoquinolin-6-yl]-carbamic acid 3,5-dichloro-benzyl ester (48)

Starting material 47 (46 mg, 0.1 mmol), 1H-1,2,3-benzothiazole-5-carboxyllic acid (22 mg, 0.1 mmol) and 4-methyl morpholin (40 µL, 0.4 mmol) were dissolved in 2 ml DMF. Then EDCI (38 mg, 0.2 mmol) and HOBt (26 mg, 0.2 mmol) were added and the mixture was stirred over night at ambient temperature. The reaction mixture was mixed with water and the resulting precipitate was filtered and dried in vacuo at 45° C. The desired product 48 could thereby be isolated as light brown solid (34 mg, 0.07 mmol, 52%).

Example 10

Synthesis of 2-[2-(4-Chloro-2-fluoro-phenyl)-acetylamino]-6-(2-pyridin-3-yl-acetyl)-4,5,6,7-tetrahydrothieno[2,3-c]pyridine-3-carboxylic acid amide (50)

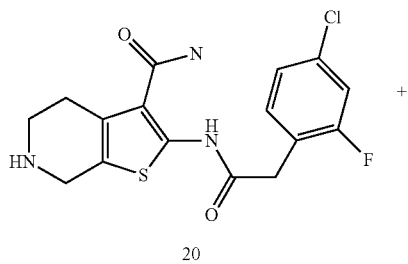

20

-continued

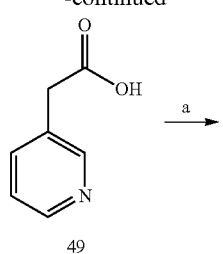

49

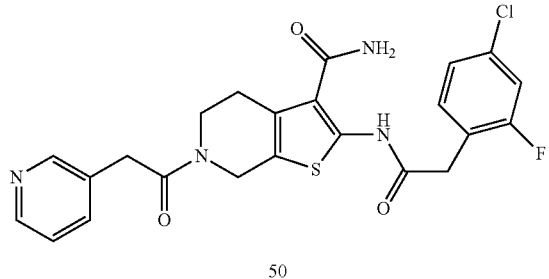

50

Starting material 49 (37 mg, 0.3 mmol) was dissolved in 2 ml dry DMF. Then EDCI (94 mg, 0.5 mmol) and HOBt (48 mg, 0.3 mmol) were added yielding a yellow solution into which 100 mg of starting material 20 (0.3 mmol) were added. Now the mixture was heated to 100° C. for 30 minutes. The reaction mixture was cooled to ambient temperature, mixed with water and the resulting precipitate was filtered and dried. This crude product was further purified by prep HPLC (Method 4) yielding the desired product 50 as light brown solid (53 mg, 0.1 mmol, 37%).

General Notes:

Analogously, p-chlorophenyl isocyanate was replaced by the following isocyanates:

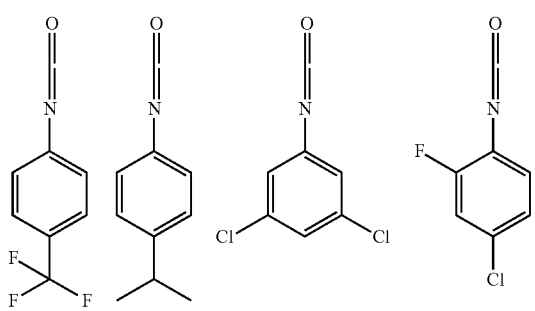

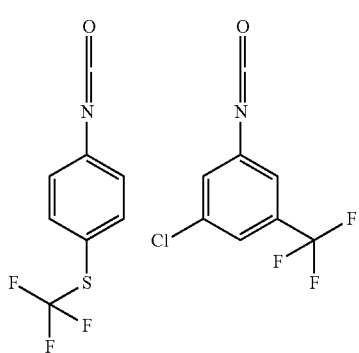

-continued

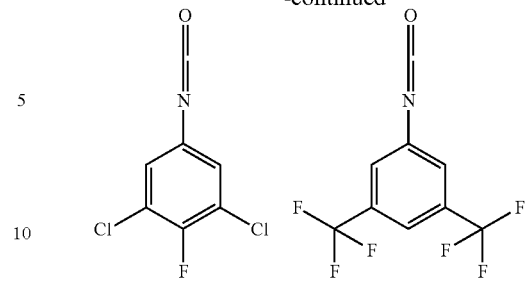

Analogously, (4-chloro-2-fluoro-phenyl)-acetic acid (18) was replaced by the following acids:

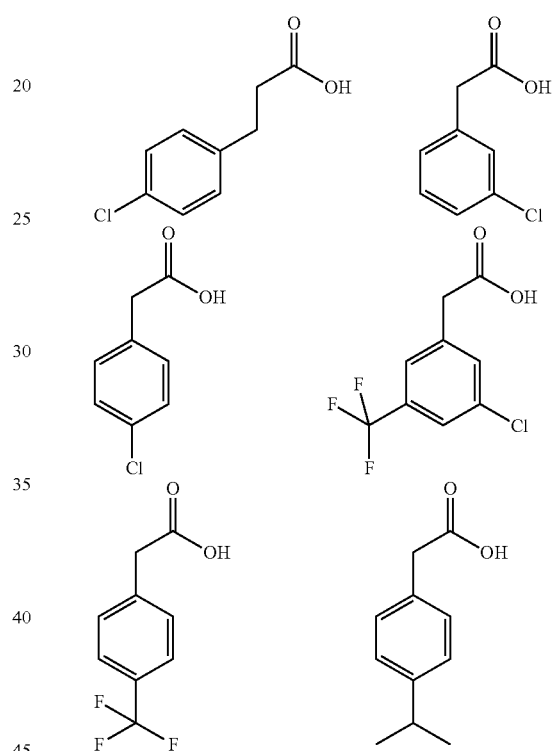

Analogously, 1H-1,2,3-benzothiazole-5-carboxylic acid was replaced by the following acids:

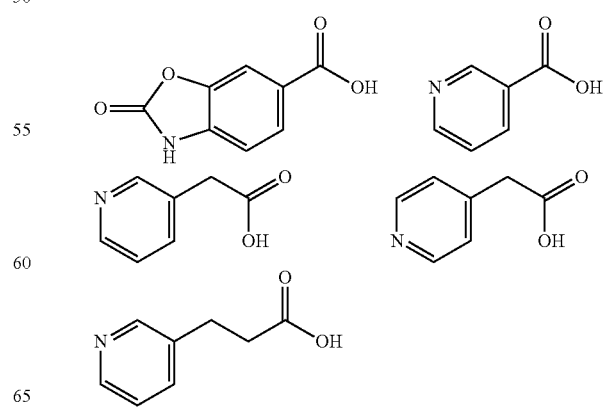

Analogously, Pyridin-3-yl-acetic acid (49) was replaced by the following acids:

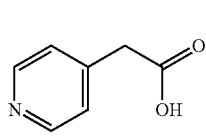 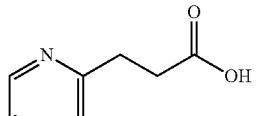

Analogously, pyridine-4-carbaldehyde (22) was replaced by the following aldehydes:

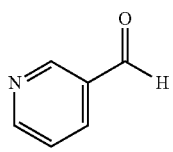 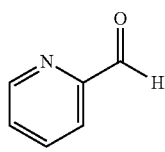

Analogously, 6-amino-3H-benzooxazol-2-one (30) was replaced by the following amines:

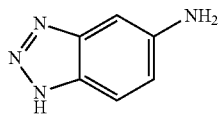 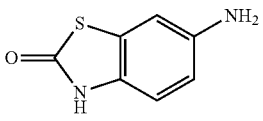

Analogously, 2-(4-Chloro-phenyl)-ethylamine (42) was replaced by the following amines:

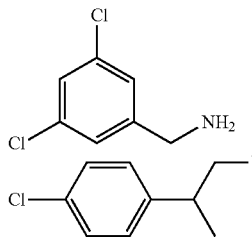

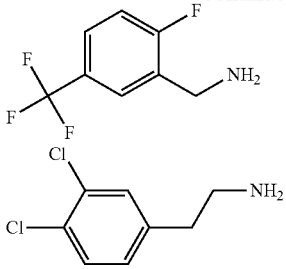
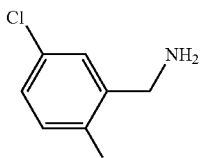
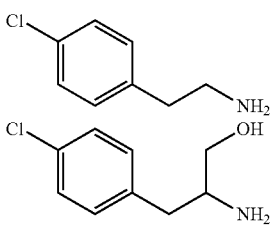
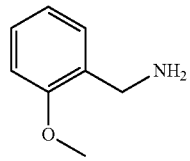
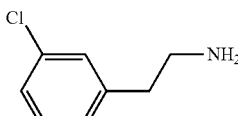
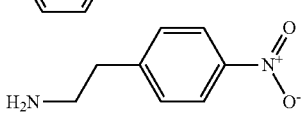
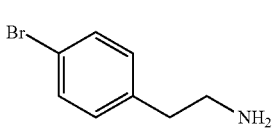
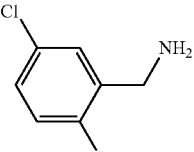
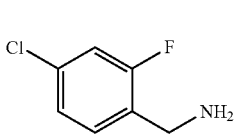

An overview about further analogously synthesized compounds of the invention including physico-chemical parameters for all compounds of the invention is given in Tables 2 and 3.

TABLE 2

| Compound | Chemical Name | ESI [M + 1]$^+$ | HPLC Rt [min] | HPLC Method | LC-MS Method |
|---|---|---|---|---|---|
| 1 | 6-(1H-Benzotriazole-5-carbonyl)-2-[3-(4-chloro-phenyl)-ureido]-4,5,6,7-tetrahydro-thieno[2,3-c]pyridine-3-carboxylic acid amide | 496 | 2.93 | A | B |
| 2 | 2-[3-(4-Chloro-phenyl)-ureido]-6-(2-oxo-2,3-dihydro-benzooxazole-6-carbonyl)-4,5,6,7-tetrahydro-thieno[2,3-c]pyridine-3-carboxylic acid amide | 512.1 | 2.95 (1.05) | A (G) | B (G) |
| 3 | 6-(1H-Benzotriazole-5-carbonyl)-2-[3-(4-trifluoromethyl-phenyl)-ureido]-4,5,6,7-tetrahydro-thieno[2,3-c]pyridine-3-carboxylic acid amide | 530.2 | 2.99 (1.08) | D (G) | B (G) |
| 4 | 6-(1H-Benzotriazole-5-carbonyl)-2-[3-(4-isopropyl-phenyl)-ureido]-4,5,6,7-tetrahydro-thieno[2,3-c]pyridine-3-carboxylic acid amide | 504 | 3.03 | A | B |

TABLE 2-continued

| Compound | Chemical Name | ESI [M + 1]+ | HPLC Rt [min] | HPLC Method | LC-MS Method |
|---|---|---|---|---|---|
| 5 | 6-(1H-Benzotriazole-5-carbonyl)-2-[3-(4-chloro-phenyl)-propionylamino]-4,5,6,7-tetrahydro-thieno[2,3-c]pyridine-3-carboxylic acid amide | 509 | 2.91 | A | B |
| 6 | 2-[3-(4-Chloro-phenyl)-propionylamino]-6-(2-oxo-2,3-dihydro-benzooxazole-6-carbonyl)-4,5,6,7-tetrahydro-thieno[2,3-c]pyridine-3-carboxylic acid amide | 525 | 3.03 | A | B |
| 7 | 2-[3-(4-Isopropyl-phenyl)-ureido]-6-(2-oxo-2,3-dihydro-benzooxazole-6-carbonyl)-4,5,6,7-tetrahydro-thieno[2,3-c]pyridine-3-carboxylic acid amide | | 3.17 | A | B |
| 8 | 2-[3-(3,5-Dichloro-phenyl)-ureido]-6-(2-oxo-2,3-dihydro-benzooxazole-6-carbonyl)-4,5,6,7-tetrahydro-thieno[2,3-c]pyridine-3-carboxylic acid amide | 547 | 3.23 | A | B |
| 9 | 6-(1H-Benzotriazole-5-carbonyl)-2-[2-(4-chloro-2-fluoro-phenyl)-acetylamino]-4,5,6,7-tetrahydro-thieno[2,3-c]pyridine-3-carboxylic acid amide | 513 | 2.89 | A | B |
| 10 | 2-[2-(4-Chloro-2-fluoro-phenyl)-acetylamino]-6-(2-oxo-2,3-dihydro-benzooxazole-6-carbonyl)-4,5,6,7-tetrahydro-thieno[2,3-c]pyridine-3-carboxylic acid amide | 529 | 2.95 | A | B |
| 11 | 6-(1H-Benzotriazole-5-carbonyl)-2-[2-(3-chloro-phenyl)-acetylamino]-4,5,6,7-tetrahydro-thieno[2,3-c]pyridine-3-carboxylic acid amide | 495 | 2.81 | A | B |
| 12 | 6-(1H-Benzotriazole-5-carbonyl)-2-[3-(3,5-dichloro-phenyl)-ureido]-4,5,6,7-tetrahydro-thieno[2,3-c]pyridine-3-carboxylic acid amide | 531 | 3.17 | A | B |
| 13 | 2-[2-(3-Chloro-phenyl)-acetylamino]-6-(2-oxo-2,3-dihydro-benzooxazole-6-carbonyl)-4,5,6,7-tetrahydro-thieno[2,3-c]pyridine-3-carboxylic acid amide | 511 | 2.91 | A | B |
| 14 | 2-[2-(4-Chloro-phenyl)-acetylamino]-6-(2-oxo-2,3-dihydro-benzooxazole-6-carbonyl)-4,5,6,7-tetrahydro-thieno[2,3-c]pyridine-3-carboxylic acid amide | 511.1 | 2.92 (1.01) | A (G) | B (G) |
| 15 | 6-(1H-Benzotriazole-5-carbonyl)-2-[3-(4-chloro-2-fluoro-phenyl)-ureido]-4,5,6,7-tetrahydro-thieno[2,3-c]pyridine-3-carboxylic acid amide | 514.1 | 2.87 (1.02) | A (G) | B (G) |
| 16 | 2-[2-(4-Chloro-2-fluoro-phenyl)-acetylamino]-6-pyridin-3-ylmethyl-4,5,6,7-tetrahydro-thieno[2,3-c]pyridine-3-carboxylic acid amide | 459 | 2.5 | A | B |
| 17 | 2-[2-(4-Chloro-2-fluoro-phenyl)-acetylamino]-6-pyridin-2-ylmethyl-4,5,6,7-tetrahydro-thieno[2,3-c]pyridine-3-carboxylic acid amide | 459 | 2.69 | A | B |
| 18 | 2-[3-(4-Chloro-phenyl)-ureido]-6-pyridin-2-ylmethyl-4,5,6,7-tetrahydro-thieno[2,3-c]pyridine-3-carboxylic acid amide | 442 | 2.73 | A | B |
| 19 | 2-[3-(4-Chloro-phenyl)-ureido]-6-(pyridine-3-carbonyl)-4,5,6,7-tetrahydro-thieno[2,3-c]pyridine-3-carboxylic acid amide | 456 | 2.83 | A | B |
| 20 | 2-[3-(4-Chloro-phenyl)-ureido]-6-pyridin-4-ylmethyl-4,5,6,7-tetrahydro-thieno[2,3-c]pyridine-3-carboxylic acid amide | 442 | 2.57 | A | B |

TABLE 2-continued

| Compound | Chemical Name | ESI [M + 1]+ | HPLC Rt [min] | HPLC Method | LC-MS Method |
|---|---|---|---|---|---|
| 21 | 2-[2-(4-Chloro-2-fluoro-phenyl)-acetylamino]-6-pyridin-4-ylmethyl-4,5,6,7-tetrahydro-thieno[2,3-c]pyridine-3-carboxylic acid amide | 459 | 2.51 | A | B |
| 22 | 2-[2-(4-Chloro-2-fluoro-phenyl)-acetylamino]-6-(2-pyridin-3-yl-acetyl)-4,5,6,7-tetrahydro-thieno[2,3-c]pyridine-3-carboxylic acid amide | 487 | 2.63 | A | B |
| 23 | 2-[2-(4-Chloro-2-fluoro-phenyl)-acetylamino]-6-(2-pyridin-4-yl-acetyl)-4,5,6,7-tetrahydro-thieno[2,3-c]pyridine-3-carboxylic acid amide | 487 | 2.6 | A | B |
| 24 | 2-[2-(4-Chloro-2-fluoro-phenyl)-acetylamino]-6-(3-pyridin-2-yl-propionyl)-4,5,6,7-tetrahydro-thieno[2,3-c]pyridine-3-carboxylic acid amide | 501 | 2.57 | A | B |
| 25 | 6-(1H-Benzotriazole-5-carbonyl)-2-[3-(4-chloro-phenyl)-ureido]-4,5,6,7-tetrahydro-thieno[2,3-c]pyridine-3-carboxylic acid methyl ester | 510.9 | 3.29 | A | B |
| 26 | 2-[3-(4-Chloro-phenyl)-ureido]-6-(2-oxo-2,3-dihydro-benzooxazole-6-carbonyl)-4,5,6,7-tetrahydro-thieno[2,3-c]pyridine-3-carboxylic acid methyl ester | 526.9 | 3.35 | A | B |
| 27 | 1-[6-(1H-Benzotriazole-5-carbonyl)-3-(pyrrolidine-1-carbonyl)-4,5,6,7-tetrahydro-thieno[2,3-c]pyridin-2-yl]-3-(4-chloro-phenyl)-urea | 550 | 2.92 | A | B |
| 28 | 2-[3-(4-Chloro-phenyl)-ureido]-1H-indole-3,6-dicarboxylic acid 3-amide 6-[(2-oxo-2,3-dihydro-benzooxazol-6-yl)-amide] | 505 | 3.28 | A | C |
| 29 | 2-[2-(4-Chloro-2-fluoro-phenyl)-acetylamino]-benzothiazole-6-carboxylic acid (2-oxo-2,3-dihydro-benzooxazol-6-yl)-amide | 497 | 3.13 | A | C |
| 30 | 2-[3-(4-Trifluoromethyl-phenyl)-ureido]-benzothiazole-6-carboxylic acid (2-oxo-2,3-dihydro-benzooxazol-6-yl)-amide | 480 | 3.23 | A | C |
| 31 | 2-[3-(4-Chloro-phenyl)-ureido]-benzothiazole-6-carboxylic acid (2-oxo-2,3-dihydro-benzooxazol-6-yl)-amide | 480 | 3.13 | A | C |
| 32 | 2-[3-(4-Trifluoromethyl-phenyl)-ureido]-benzothiazole-6-carboxylic acid (1H-benzotriazol-5-yl)-amide | 498 | 3.2 | A | C |
| 33 | 6-(1H-Benzotriazole-5-carbonyl)-4,5,6,7-tetrahydro-2H-pyrazolo[3,4-c]pyridine-3-carboxylic acid 3,5-dichloro-benzylamide | 470 | not available | F | E |
| 34 | 6-(1H-Benzotriazole-5-carbonyl)-4,5,6,7-tetrahydro-2H-pyrazolo[3,4-c]pyridine-3-carboxylic acid 4-chloro-benzylamide | 436.2 | not available | F | E |
| 35 | 6-(1H-Benzotriazole-5-carbonyl)-4,5,6,7-tetrahydro-2H-pyrazolo[3,4-c]pyridine-3-carboxylic acid [2-(4-chloro-phenyl)-propyl]-amide | 464.2 | 3.65 | F | E |
| 36 | 6-(1H-Benzotriazole-5-carbonyl)-4,5,6,7-tetrahydro-2H-pyrazolo[3,4-c]pyridine-3-carboxylic acid 2-fluoro-5-trifluoromethyl-benzylamide | 488.2 | 3.6 | F | E |
| 37 | 6-(1H-Benzotriazole-5-carbonyl)-4,5,6,7-tetrahydro-2H-pyrazolo[3,4-c]pyridine-3-carboxylic acid [2-(3,4-dichloro-phenyl)-ethyl]-amide | 484 | 4.5 | F | E |
| 38 | 6-(1H-Benzotriazole-5-carbonyl)-4,5,6,7-tetrahydro-2H-pyrazolo[3,4-c]pyridine-3-carboxylic acid 2,5-dichloro-benzylamide | 470 | 3.52 | F | E |

TABLE 2-continued

| Compound | Chemical Name | ESI [M + 1]+ | HPLC Rt [min] | HPLC Method | LC-MS Method |
|---|---|---|---|---|---|
| 39 | 6-(1H-Benzotriazole-5-carbonyl)-4,5,6,7-tetrahydro-2H-pyrazolo[3,4-c]pyridine-3-carboxylic acid [2-(4-chloro-phenyl)-ethyl]-amide | 450.2 | 4.32 | F | E |
| 40 | 6-(1H-Benzotriazole-5-carbonyl)-4,5,6,7-tetrahydro-2H-pyrazolo[3,4-c]pyridine-3-carboxylic acid [2-(4-chloro-phenyl)-1-hydroxymethyl-ethyl]-amide | 480.2 | 3.01 | F | E |
| 41 | 6-(1H-Benzotriazole-5-carbonyl)-4,5,6,7-tetrahydro-2H-pyrazolo[3,4-c]pyridine-3-carboxylic acid 2-methoxy-benzylamide | 432.2 | 2.99 | F | E |
| 42 | 6-(1H-Benzotriazole-5-carbonyl)-4,5,6,7-tetrahydro-2H-pyrazolo[3,4-c]pyridine-3-carboxylic acid [2-(3-chloro-phenyl)-ethyl]-amide | 450.2 | 3.39 | F | E |
| 43 | 6-(1H-Benzotriazole-5-carbonyl)-4,5,6,7-tetrahydro-2H-pyrazolo[3,4-c]pyridine-3-carboxylic acid [2-(4-nitro-phenyl)-ethyl]-amide | 461.1 | 3.12 | F | E |
| 44 | 6-(1H-Benzotriazole-5-carbonyl)-4,5,6,7-tetrahydro-2H-pyrazolo[3,4-c]pyridine-3-carboxylic acid [2-(4-bromo-phenyl)-ethyl]-amide | 496.1 | 3.52 | F | E |
| 45 | 6-(1H-Benzotriazole-5-carbonyl)-4,5,6,7-tetrahydro-2H-pyrazolo[3,4-c]pyridine-3-carboxylic acid 5-chloro-2-methoxy-benzylamide | 466.1 | 3.41 | F | E |
| 46 | 6-(1H-Benzotriazole-5-carbonyl)-4,5,6,7-tetrahydro-2H-pyrazolo[3,4-c]pyridine-3-carboxylic acid 4-chloro-2-fluoro-benzylamide | 454.1 | 3.39 | F | E |
| 47 | 6-(1H-Benzotriazole-5-carbonyl)-4,5,6,7-tetrahydro-2H-pyrazolo[3,4-c]pyridine-3-carboxylic acid [2-(4-fluoro-phenyl)-ethyl]-amide | 434.2 | 3.23 | F | E |
| 48 | [2-(1H-Benzotriazole-5-carbonyl)-1,2,3,4-tetrahydro-isoquinolin-6-yl]-carbamic acid 3,5-dichloro-benzyl ester | 496 | 4.61 | F | E |

TABLE 3

| Compound | Chemical Name | ESI [M + 1]+ | HPLC Rt [min] Method F | HPLC Rt [min] Method E |
|---|---|---|---|---|
| 49 | 6-(1H-Benzotriazole-5-carbonyl)-4,5,6,7-tetrahydro-2H-pyrazolo[3,4-c]pyridine-3-carboxylic acid 4-trifluoromethylsulfanyl-benzylamide | 502 | 3.82 | 2.10 |
| 50 | 3-(1H-Benzotriazol-5-ylcarbamoyl)-1,4,5,7-tetrahydro-pyrazolo[3,4-c]pyridine-6-carboxylic acid 4-trifluoromethyl-benzyl ester | 486 | 4.08 | 2.28 |
| 51 | 6-(1H-Benzotriazole-5-carbonyl)-4,5,6,7-tetrahydro-2H-pyrazolo[3,4-c]pyridine-3-carboxylic acid 3-bromo-4-fluoro-benzylamide | 498, 500 | 3.47 | 1.91 |
| 52 | 3-(1H-Benzotriazol-5-ylcarbamoyl)-2,4,5,7-tetrahydro-pyrazolo[3,4-c]pyridine-6-carboxylic acid 3,5-dichloro-benzyl ester | 487 | 4.07 | 2.22 |
| 53 | 3-(1H-Benzotriazol-5-ylcarbamoyl)-2,4,5,7-tetrahydro-pyrazolo[3,4-c]pyridine-6-carboxylic acid 3,5-bis-trifluoromethyl-benzyl ester | 554 | 4.23 | 2.36 |
| 54 | 3-(1H-Benzotriazol-5-ylcarbamoyl)-2,4,5,7-tetrahydro-pyrazolo[3,4-c]pyridine-6-carboxylic acid 3-chloro-4-trifluoromethyl-benzyl ester | 521 | 4.29 | 2.24 |

TABLE 3-continued

| Compound | Chemical Name | ESI [M + 1]⁺ | HPLC Rt [min] Method F | HPLC Rt [min] Method E |
|---|---|---|---|---|
| 55 | 3-(1H-Benzotriazol-5-ylcarbamoyl)-2,4,5,7-tetrahydro-pyrazolo[3,4-c]pyridine-6-carboxylic acid 3-trifluoromethyl-benzyl ester | 486 | 4.03 | 2.21 |
| 56 | 3-(1H-Benzotriazol-5-ylcarbamoyl)-2,4,5,7-tetrahydro-pyrazolo[3,4-c]pyridine-6-carboxylic acid 4-trifluoromethylsulfanyl-benzyl ester | 518 | 4.35 | 2.27 |
| 57 | 3-(1H-Benzotriazol-5-ylcarbamoyl)-2,4,5,7-tetrahydro-pyrazolo[3,4-c]pyridine-6-carboxylic acid 4-trifluoromethoxy-benzyl ester | 502 | 4.16 | 2.28 |
| 58 | 3-(1H-Benzotriazol-5-ylcarbamoyl)-2,4,5,7-tetrahydro-pyrazolo[3,4-c]pyridine-6-carboxylic acid 3-chloro-4-trifluoromethoxy-benzyl ester | 537 | 4.37 | 2.29 |
| 59 | (1H-Benzotriazol-5-yl)-{3-[3-(4-methoxy-phenyl)-piperidine-1-carbonyl]-2,4,5,7-tetrahydro-pyrazolo[3,4-c]pyridin-6-yl}-methanone | 487 | 3.39 | 1.83 |
| 60 | 6-(1H-Benzotriazole-5-carbonyl)-4,5,6,7-tetrahydro-2H-pyrazolo[3,4-c]pyridine-3-carboxylic acid 4-trifluoromethoxy-benzylamide | 486 | 3.60 | 2.04 |
| 61 | 6-(1H-Benzotriazole-5-carbonyl)-4,5,6,7-tetrahydro-2H-pyrazolo[3,4-c]pyridine-3-carboxylic acid 4-trifluoromethyl-benzylamide | 470 | 3.52 | 2.01 |
| 62 | 6-(1H-Benzotriazole-5-carbonyl)-4,5,6,7-tetrahydro-2H-pyrazolo[3,4-c]pyridine-3-carboxylic acid (6-methoxy-1,2,3,4-tetrahydro-naphthalen-2-yl)-amide | 473 | 3.41 | 1.84 |
| 63 | 3-{[6-(1H-Benzotriazole-5-carbonyl)-4,5,6,7-tetrahydro-2H-pyrazolo[3,4-c]pyridine-3-carbonyl]-amino}-3-(4-tert-butyl-phenyl)-propionic acid methyl ester | 531 | 4.00 | 2.19 |

In the following $^1$H-NMR data for selected compounds of the invention are displayed:

Compound 33, $C_{21}H_{17}Cl_2N_7O_2$
$^1$H NMR (500 MHz, DMSO-d6) δ [ppm]=13.15 (s, 1H), 8.75 (s, 1H), 8.03 (s, 1H), 7.99 (d, J=8.4, 1H), 7.50 (d, J=8.4, 1H), 7.47 (s, 1H), 7.34 (s, 2H), 4.79 (s, 2H), 4.40 (s, 2H), 4.12-3.65 (m, 2H), 2.95-2.60 (m, 3H).

Compound 37, $C_{22}H_{19}Cl_2N_7O_2$
$^1$H NMR (500 MHz, DMSO-d6) δ [ppm]=16.08 (s, 1H), 13.22-12.55 (m, 1H), 8.18-7.92 (m, 3H), 7.60-7.52 (m, 3H), 7.22 (d, J=8.0, 1 H), 4.90-4.45 (m, 2H), 3.85 (s, 1H), 3.60-3.40 (m, 3H), 2.84 (t, J=12.3, 2H), 2.76 (s, 2H).

Compound 48, $C_{24}H_{19}Cl_2N_5O_3$
$^1$H NMR (500 MHz, DMSO-d6) δ [ppm]=9.76 (s, 1H), 8.05-7.87 (m, 2H), 7.58 (s, 1H), 7.49 (s, 3H), 7.35-7.12 (m, 3H), 5.15 (s, 2H), 4.82-4.40 (m, 2H), 4.02-3.50 (m, 2H), 2.84 (s, 2H), 2.35-2.20 (m, 1H).

Compound 19, $C_{21}H_{18}ClN_5O_3S$
$^1$H NMR (500 MHz, DMSO) δ [ppm]=10.86 (s, 1H), 10.20 (s, 1H), 8.71 (d, J=4.5, 2H), 7.91 (s, 1H), 7.52 (m, 3H), 7.35 (d, J=8.1, 2H), 7.6-7.2 (br. s, 1H), 6.98 (br. s, 1H), 4.74 (s, 0.67×2H) and 4.56 (s, 0.33×2H), 3.90 (s, 0.33×2H) and 3.55 (s, 0.67×2H), 2.91 (s, 2H).

Compound 7, $C_{26}H_{25}N_5O_5S$
$^1$H NMR (500 MHz, DMSO) δ [ppm]=11.86 (s, 1H), 10.76 (s, 1H), 9.95 (s, 1H), 7.41 (s, 1H), 7.39 (d, J=8.3, 2H), 7.29 (d, J=7.9, 1 H), 7.17 (m, 3H), 7.6-7.1 (br. s, 1H), 7.00 (br. s, 1H), 4.65 (s, 2H), 3.54 (m, 2H), 3.06-2.69 (m, 3H), 1.19 (d, J=6.9, 6H).

Compound 29, $C_{23}H_{14}ClFN_4O_4S$
$^1$H NMR (400 MHz, DMSO) δ [ppm]=12.83 (s, 1H), 11.54 (s, 1H), 10.33 (s, 1H), 8.59 (d, J=1.7, 1H), 8.03 (dd, J=8.5, 1.7, 1H), 7.86 (t, J=8.5, 1H), 7.83 (d, J=1.7, 1H), 7.54-7.41 (m, 3H), 7.30 (dd, J=8.2, 1.9, 1H), 7.08 (d, J=8.4, 1H), 3.97 (s, 2H).

Compound 31, $C_{22}H_{14}ClN_5O_4S$
$^1$H NMR (400 MHz, DMSO) δ [ppm]=11.58 (s, 1H), 10.33 (s, 1H), 9.36 (s, 1H), 8.53 (s, 1H), 8.03-7.94 (m, 1H), 7.84 (d, J=1.9, 1H), 7.80-7.66 (m, 2H), 7.59 (m, 2H), 7.51 (dd, J=8.5, 1.9, 1H), 7.44-7.36 (m, 2H), 7.09 (d, J=8.4, 1H).

2-Amino-4,5,6,7-tetrahydro-thieno[2,3-c]pyridine-3-carboxylic acid methyl ester hydrochloride (17), $C_9H_{12}N_2O_2S$*HCl $^1$H NMR (400 MHz, DMSO) δ [ppm]=7.35 (s, 2H), 4.59 (s, 2H), 3.77 (s, 2H), 3.68 (s, 3H), 3.04 (t, J=5.9, 2H), 2.73-2.66 (m, 2H).

Compound 50
$^1$H NMR (500 MHz, DMSO) δ=15.53 (s, 1H), 13.22 (s, 1H), 10.25 (s, 1H), 8.47 (s, 1H), 7.89 (s, 1H), 7.83-7.68 (m, 3H), 7.63 (d, J=8.0, 2H), 5.25 (s, 2H), 4.72-4.58 (m, 2H), 3.72 (s, 2H), 2.85 (s, 2H).

Compound 51
$^1$H NMR (500 MHz, DMSO) δ=15.87 (s, 1H), 13.10 (s, 1H), 8.69 (s, 1H), 8.07-7.90 (m, 2H), 7.61 (s, 1H), 7.49 (d, J=8.5, 1 H), 7.40-7.24 (m, 2H), 4.77 (s, 2H), 4.38 (s, 2H), 3.81 (s, 1H), 3.53 (s, 1H), 2.79 (s, 2H).

Compound 52

$^1$H NMR (500 MHz, DMSO, d-TFA exchanged, $C_{21}H_{14}D_3Cl_2N_7O_3$) δ=8.48 (d, J=1.6, 1H), 7.82 (d, J=9.0, 1H), 7.68 (dd, J=9.0, 1.6, 1H), 7.35-7.27 (m, 3H), 5.06 (s, 2H), 4.65-4.53 (m, 2H), 3.64 (s, 2H), 2.82 (t, J=5.3, 2H).

Compound 53

$^1$H NMR (500 MHz, DMSO) δ=15.54 (s, 1H), 13.22 (s, 1H), 10.24 (s, 1H), 8.46 (s, 1H), 8.13-8.07 (m, 3H), 7.89 (d, J=7.9, 1H), 7.75 (s, 1H), 5.32 (s, 2H), 4.72-4.57 (m, 2H), 3.71 (s, 2H), 2.84 (s, 2H).

Compound 54

$^1$H NMR (500 MHz, DMSO) δ=15.50 (s, OH, 1H), 13.22 (s, 1H), 10.24 (s, 1H), 8.46 (s, 1H), 7.89 (d, J=8.2, 2H), 7.79-7.70 (m, 2H), 7.58 (d, J=8.2, 1H), 5.24 (s, 2H), 4.75-4.60 (m, 2H), 3.79-3.63 (m, 2H), 2.86 (s, 2H).

Compound 55

$^1$H NMR (500 MHz, DMSO) δ=15.50 (s, 1H), 13.20 (s, 1H), 10.22 (s, 1H), 8.45 (s, 1H), 7.88 (d, J=7.9, 1H), 7.78-7.66 (m, 4H), 7.63 (t, J=7.7, 1H), 5.23 (s, 2H), 4.62 (s, 2H), 3.69 (s, 2H), 2.83 (t, J=5.4, 2H).

Compound 58

$^1$H NMR (500 MHz, DMSO) δ=15.54 (s, 1H), 13.22 (s, 1H), 10.25 (s, 1H), 8.47 (s, 1H), 7.89 (s, 1H), 7.80-7.73 (m, 2H), 7.60 (d, J=8.7, 1H), 7.52 (dd, J=8.5, 1.9, 1H), 5.18 (s, 2H), 4.70-4-58 (m, 2H), 3.70 (s, 2H), 2.85 (s, 2H).

Compound 60

$^1$H NMR (500 MHz, DMSO) δ=15.75 (s, 1H), 13.09 (s, 1H), 8.65 (s, 1H), 8.07-7.92 (m, 2H), 7.49 (d, J=8.5, 1H), 7.42 (d, J=8.4, 2H), 7.30 (d, J=8.2, 2H), 4.88-4.55 (m, 2H), 4.42 (d, J=5.2, 2H), 3.99-3.45 (m, 2H), 2.80 (s, 2H).

The following analytical methods were use for determining above illustrated physico-chemical parameters:

ESI: Electrospray Ionization Mass Spectrometry (M+H)+

Analytical Chromatography Methods

A HPLC-Method: 1__100__2 Speed (machine: LaChrom)
Column: Chromolith Performance RP18e 100-3 mm
Flow: 2 ml/min (Pump: L-7100)
Solvent A: water+0.01% TFA
Solvent B: Acetonitrile+0.01% TFA
Wavelength (WL): 220 nm (Detector: L-7455)
0-0.2 100% A, 0.2-3.7 to 100% B, 3.7-4.4 100% B, 4.5-5.0 100% A B LC-MS-Method: polar.M (machine: Agilent 1100 Series)
Column: Chromolith Speed Rod RP18e-50-4.6
Flow: 2.4 m l/m in
Solvent A: water+0.1% TFA
Solvent B: Acetonitrile+0.1% TFA
WL: 220 nm
Gradient: 0-2.6 min: 4% B to 100% B, 2.6-3.3 min: 100% B C LC-MS-Method: polar.M (machine: Agilent 1100 Series)
Column: Chromolith Speed Rod RP18e-50-4.6
Flow: 2.4 ml/m in
Solvent A: water+0.05% HCOOH
Solvent B: Acetonitrile+0.04% HCOOH
WL: 220 nm
Gradient: 0-2.8 min: 4% B to 100% B, 2.8-3.3 min: 100% B D HPLC-Method: 1__100__2 (machine: LaChrom)
Column: Chromolith Performance RP18e 100-3 mm
Flow: 2 ml/min (Pump: L-7100)
Solvent A: water+0.01% HCOOH
Solvent B: Acetonitrile+0.01% HCOOH
WL: 220 nm (Detector: L-7455)
0-0.2 100% A, 0.2-3.7 to 100% B, 3.7-4.4 100% B, 4.5-5.0 100% A E HPLC/MS-Method (polar)
Solvent A: water+0.05% HCOOH
Solvent B: Acetonitrile+0.04% HCOOH
Flow: 2.4 ml/min, WL: 220 nm
Gradient: 0.0 min 4% B
2.8 min 100% B
3.3 min 100% B
3.4 min 4% B
Column: Chromolith® Speed ROD RP-18e 50-4.6 mm F HPLC-Method (non-polar)
Solvent A: water+0.1% TFA
Solvent B: Acetonitrile+0.08% TFA
Flow: 1.5 ml/min
Gradient: 0.0 min 20% B
5.0 min 100% B
5.5 min 100% B
6.0 min 20% B
6.5 min 20% B
Column: Chromolith Performance RP18e 100-3

G HPLC/MS-Method
Machine: Waters Acquity HPLC® with PDA and ELSD; Waters SQD (ESI+/− and APCI+/−)
Solvent A: Acetonitrile+0.1% HCOOH
Solvent B: Water+0.1% HCOOH
Flow: 1 ml/min, WL: 254 nm
Gradient: 0.0 min 1% A
1.7 min 99% A
2.0 min 99% A
Column: Acquity HPLC® BEH C18 (2.1×50 mm)
Column Temperature: 60° C.

Preparative Chromatography Methods:

Prep.-HPLC-Method 1:
Machine: Agilent 1100 Series
Column: Chromolith Prep Rod RP18e
flow: 50 ml/min
Solvent A: Acetonitrile+0.1% TFA
Solvent B: water+0.1% TFA
WL: 220 nm
Gradient: from 1-20% ACN in 2 min, from 20-40% ACN in 8 min, collect from 2 min to 11 min Prep.-HPLC-Method 2:
Machine: Agilent 1100 Series
Column: Chromolith Prep Rod RP18e
Flow: 50 ml/min
Solvent A: Acetonitrile+0.1% TFA
Solvent B: Water+0.1% TFA
WL: 220 nm
Gradient: from 1-30% ACN in 10 min, collect from 2 min to 11 min Prep.-HPLC-Method 3:
machine: Agilent 1100 Series
Column: Chromolith Prep Rod RP18e
flow: 50 ml/min
Solvent A: Acetonitrile+0.1% TFA
Solvent B: Water+0.1% TFA
WL: 220 nm
Gradient: from 1-25% ACN in 2 min, from 25-50% ACN in 8 min, collect from 2 min to 11 min Prep.-HPLC-Method 4:
Machine: Agilent 1100 Series
Column: Chromolith Prep Rod RP18e
flow: 50 ml/min
Solvent A: Acetonitrile+0.1% TFA
Solvent B: Water+0.1% TFA
WL: 220 nm Gradient: from 1-15% ACN in 2 min, from 15-35% ACN in 8 min, collect from 2 min to 11 min Flashmaster Method 1:
Machine: Flashmaster
Column material: Chromolith NH$_2$
solvent: ethyl acetate (EE)/MeOH
Gradient: 100% EE 5 min, in 15 min to 3% MeOH, in 16 min to 4% MeOH, in 15 min to 10% MeOH, 15 min MeOH flush

II. Autotaxin Assay

Assay Description

Autotaxin activity is measured indirectly by means of Amplex Red Reagent. In this course, Amplex Red is measured as fluorogenic indicator for generated H$_2$O$_2$. Autotaxin converts substrate lysophosphatidylcholine (LPC) to phosphocholine and lysophosphatidylic acid (LPA). After the conversion phosphocholine is reacted with alkaline phosphatase to obtain inorganic phosphate and choline. During the next step choline is oxidized with choline oxidase to yield betaine, whereby H$_2$O$_2$ is generated. H$_2$O$_2$ reacts with Amplex Red Reagent in the presence of peroxidase (Horseradish peroxidase) in an 1:1 stochiometry and yields highly fluorescent resorufin. The generated fluorescence is measured in a reaction-dependent kinetic mode in order to enable subtraction of fluorescence signals of possible other fluorescent compounds that are not part of the reaction from total measured fluorescence.

Performing the Assay 1.5 µl of a standard solution or of the compounds of the invention are dissolved in 20 mM Hepes pH 7.2 with maximally 7.7% DMSO in individual concentrations. The resulting solution is pre-incubated together with 10 µl (16 ng) of highly purified recombinant autotaxin in a black 384-hole microtiter plate for 30 min at 22° C.

Thereafter, the reaction is started through the addition of 5 µL-a-lysophosphatidyl-choline (LPC), whereby the final concentration of LPC is 75 µM. The mixture is incubated for 90 min. at 37° C. After the incubation Amplex Red Reagent, peroxidase (Horseradish peroxidase) and choline oxidase are added. The fluorescence is immediately measured at a wavelength of 612 nm with an excitation wavelength of 485 nm in a "Tecan Ultra multimode" fluorescence reader. The activity of autotaxin is indirectly calculated via the amount of detected generated H$_2$O$_2$.

For IC$_{50}$ analysis, ten serial 1:3 dilutions starting at 30 µM for each compound were run in duplicates.

IC$_{50}$ values were calculated on normalized data. For normalization, control wells were added to each assay plate and the signal of uninhibited control wells was set to 100%, whereas the signal inhibited by 500 µM C14 LPA, (Avanti Polar Lipids, Cat#857120P) was set to 0%. Curves were fitted and IC$_{50}$ values calculated by the following model using proprietary analysis software:

$$Y = \text{Bottom} + (100 - \text{Bottom})/(1 + 10^{((\log IC_{50} - X)*\text{Hill-Slope})})$$

Where X is the logarithm of concentration. Y is the response; Y starts at Bottom and goes to Top with a sigmoid shape.

Material

Microtiter plate: PS-Microplate, 384-hole, small volume, black Corning, Cat#3677
Protein: Recombinant autotaxin (baculoviral Hi5 expression)
Substrate: L-a-lysophosphatidyl choline (chicken egg); Avanti Polar Lipids #830071P
Standard: C14 LPA, Avanti Polar Lipids, Cat# 857120P
Detection Reagent: Amplex Red Reagent; Invitrogen #A12222; dissolved in 1.923 ml of DMSO peroxidase Type VI-A (horseradish), Sigma #P6782; dissolved in 7.45 ml of test buffer, Choline Oxidase; Sigma #C5896; dissolved in 2.47 ml test buffer Detection Reagent Mix: 1:100 dilution of Amplex Red Regent in test buffer Test buffer: 200 mM Tris-HCl, Merck, Cat #1.08219, pH 7.9; 0.1% BSA, lipid free, Roche Cat#775835

TABLE 4

| Compound | Chemical Name | IC$_{50}$ value [M] or % CTRL (1E-05) |
|---|---|---|
| 1 | 6-(1H-Benzotriazole-5-carbonyl)-2-[3-(4-chloro-phenyl)-ureido]-4,5,6,7-tetrahydro-thieno[2,3-c]pyridine-3-carboxylic acid amide | <1.00E-06 |
| 2 | 2-[3-(4-Chloro-phenyl)-ureido]-6-(2-oxo-2,3-dihydro-benzooxazole-6-carbonyl)-4,5,6,7-tetrahydro-thieno[2,3-c]pyridine-3-carboxylic acid amide | <1.00E-06 |
| 3 | 6-(1H-Benzotriazole-5-carbonyl)-2-[3-(4-trifluoromethyl-phenyl)-ureido]-4,5,6,7-tetrahydro-thieno[2,3-c]pyridine-3-carboxylic acid amide | <1.00E-06 |
| 4 | 6-(1H-Benzotriazole-5-carbonyl)-2-[3-(4-isopropyl-phenyl)-ureido]-4,5,6,7-tetrahydro-thieno[2,3-c]pyridine-3-carboxylic acid amide | <1.00E-06 |
| 5 | 6-(1H-Benzotriazole-5-carbonyl)-2-[3-(4-chloro-phenyl)-propionylamino]-4,5,6,7-tetrahydro-thieno[2,3-c]pyridine-3-carboxylic acid amide | <1.00E-06 |
| 6 | 2-[3-(4-Chloro-phenyl)-propionylamino]-6-(2-oxo-2,3-dihydro-benzooxazole-6-carbonyl)-4,5,6,7-tetrahydro-thieno[2,3-c]pyridine-3-carboxylic acid amide | <1.00E-06 |
| 7 | 2-[3-(4-Isopropyl-phenyl)-ureido]-6-(2-oxo-2,3-dihydro-benzooxazole-6-carbonyl)-4,5,6,7-tetrahydro-thieno[2,3-c]pyridine-3-carboxylic acid amide | <1.00E-06 |
| 8 | 2-[3-(3,5-Dichloro-phenyl)-ureido]-6-(2-oxo-2,3-dihydro-benzooxazole-6-carbonyl)-4,5,6,7-tetrahydro-thieno[2,3-c]pyridine-3-carboxylic acid amide | <1.00E-05 |
| 9 | 6-(1H-Benzotriazole-5-carbonyl)-2-[2-(4-chloro-2-fluoro-phenyl)-acetylamino]-4,5,6,7-tetrahydro-thieno[2,3-c]pyridine-3-carboxylic acid amide | <1.00E-06 |
| 10 | 2-[2-(4-Chloro-2-fluoro-phenyl)-acetylamino]-6-(2-oxo-2,3-dihydro-benzooxazole-6-carbonyl)-4,5,6,7-tetrahydro-thieno[2,3-c]pyridine-3-carboxylic acid amide | <1.00E-06 |
| 11 | 6-(1H-Benzotriazole-5-carbonyl)-2-[2-(3-chloro-phenyl)-acetylamino]-4,5,6,7-tetrahydro-thieno[2,3-c]pyridine-3-carboxylic acid amide | <1.00E-06 |
| 12 | 6-(1H-Benzotriazole-5-carbonyl)-2-[3-(3,5-dichloro-phenyl)-ureido]-4,5,6,7-tetrahydro-thieno[2,3-c]pyridine-3-carboxylic acid amide | <1.00E-05 |
| 13 | 2-[2-(3-Chloro-phenyl)-acetylamino]-6-(2-oxo-2,3-dihydro-benzooxazole-6-carbonyl)-4,5,6,7-tetrahydro-thieno[2,3-c]pyridine-3-carboxylic acid amide | <1.00E-06 |
| 14 | 2-[2-(4-Chloro-phenyl)-acetylamino]-6-(2-oxo-2,3-dihydro-benzooxazole-6-carbonyl)-4,5,6,7-tetrahydro-thieno[2,3-c]pyridine-3-carboxylic acid amide | <1.00E-06 |
| 15 | 6-(1H-Benzotriazole-5-carbonyl)-2-[3-(4-chloro-2-fluoro-phenyl)-ureido]-4,5,6,7-tetrahydro-thieno[2,3-c]pyridine-3-carboxylic acid amide | <1.00E-06 |

TABLE 4-continued

| Compound | Chemical Name | IC$_{50}$ value [M] or % CTRL (1E−05) |
|---|---|---|
| 16 | 2-[2-(4-Chloro-2-fluoro-phenyl)-acetylamino]-6-pyridin-3-ylmethyl-4,5,6,7-tetrahydro-thieno[2,3-c]pyridine-3-carboxylic acid amide | <3.00E−05 |
| 17 | 2-[2-(4-Chloro-2-fluoro-phenyl)-acetylamino]-6-pyridin-2-ylmethyl-4,5,6,7-tetrahydro-thieno[2,3-c]pyridine-3-carboxylic acid amide | 66% |
| 18 | 2-[3-(4-Chloro-phenyl)-ureido]-6-pyridin-2-ylmethyl-4,5,6,7-tetrahydro-thieno[2,3-c]pyridine-3-carboxylic acid amide | 88% |
| 19 | 2-[3-(4-Chloro-phenyl)-ureido]-6-(pyridine-3-carbonyl)-4,5,6,7-tetrahydro-thieno[2,3-c]pyridine-3-carboxylic acid amide | <1.00E−05 |
| 20 | 2-[3-(4-Chloro-phenyl)-ureido]-6-pyridin-4-ylmethyl-4,5,6,7-tetrahydro-thieno[2,3-c]pyridine-3-carboxylic acid amide | <1.00E−05 |
| 21 | 2-[2-(4-Chloro-2-fluoro-phenyl)-acetylamino]-6-pyridin-4-ylmethyl-4,5,6,7-tetrahydro-thieno[2,3-c]pyridine-3-carboxylic acid amide | <1.00E−05 |
| 22 | 2-[2-(4-Chloro-2-fluoro-phenyl)-acetylamino]-6-(2-pyridin-3-yl-acetyl)-4,5,6,7-tetrahydro-thieno[2,3-c]pyridine-3-carboxylic acid amide | <1.00E−05 |
| 23 | 2-[2-(4-Chloro-2-fluoro-phenyl)-acetylamino]-6-(2-pyridin-4-yl-acetyl)-4,5,6,7-tetrahydro-thieno[2,3-c]pyridine-3-carboxylic acid amide | <1.00E−05 |
| 24 | 2-[2-(4-Chloro-2-fluoro-phenyl)-acetylamino]-6-(3-pyridin-2-yl-propionyl)-4,5,6,7-tetrahydro-thieno[2,3-c]pyridine-3-carboxylic acid amide | <1.00E−05 |
| 25 | 6-(1H-Benzotriazole-5-carbonyl)-2-[3-(4-chloro-phenyl)-ureido]-4,5,6,7-tetrahydro-thieno[2,3-c]pyridine-3-carboxylic acid methyl ester | <3.00E−05 |
| 26 | 2-[3-(4-Chloro-phenyl)-ureido]-6-(2-oxo-2,3-dihydro-benzooxazole-6-carbonyl)-4,5,6,7-tetrahydro-thieno[2,3-c]pyridine-3-carboxylic acid methyl ester | <1.00E−05 |
| 27 | 1-[6-(1H-Benzotriazole-5-carbonyl)-3-(pyrrolidine-1-carbonyl)-4,5,6,7-tetrahydro-thieno[2,3-c]pyridin-2-yl]-3-(4-chloro-phenyl)-urea | 52% |
| 28 | 2-[3-(4-Chloro-phenyl)-ureido]-1H-indole-3,6-dicarboxylic acid 3-amide 6-[(2-oxo-2,3-dihydro-benzooxazol-6-yl)-amide] | <3.00E−05 |
| 29 | 2-[2-(4-Chloro-2-fluoro-phenyl)-acetylamino]-benzothiazole-6-carboxylic acid (2-oxo-2,3-dihydro-benzooxazol-6-yl)-amide | <1.00E−05 |
| 30 | 2-[3-(4-Trifluoromethyl-phenyl)-ureido]-benzothiazole-6-carboxylic acid (2-oxo-2,3-dihydro-benzooxazol-6-yl)-amide | 93% |
| 31 | 2-[3-(4-Chloro-phenyl)-ureido]-benzothiazole-6-carboxylic acid (2-oxo-2,3-dihydro-benzooxazol-6-yl)-amide | 94% |
| 32 | 2-[3-(4-Trifluoromethyl-phenyl)-ureido]-benzothiazole-6-carboxylic acid (1H-benzotriazol-5-yl)-amide | 64% |
| 33 | 6-(1H-Benzotriazole-5-carbonyl)-4,5,6,7-tetrahydro-2H-pyrazolo[3,4-c]pyridine-3-carboxylic acid 3,5-dichloro-benzylamide | <1.00E−05 |
| 34 | 6-(1H-Benzotriazole-5-carbonyl)-4,5,6,7-tetrahydro-2H-pyrazolo[3,4-c]pyridine-3-carboxylic acid 4-chloro-benzylamide | <1.00E−05 |
| 35 | 6-(1H-Benzotriazole-5-carbonyl)-4,5,6,7-tetrahydro-2H-pyrazolo[3,4-c]pyridine-3-carboxylic acid [2-(4-chloro-phenyl)-propyl]-amide | <1.00E−05 |
| 36 | 6-(1H-Benzotriazole-5-carbonyl)-4,5,6,7-tetrahydro-2H-pyrazolo[3,4-c]pyridine-3-carboxylic acid 2-fluoro-5-trifluoromethyl-benzylamide | <3.00E−05 |
| 37 | 6-(1H-Benzotriazole-5-carbonyl)-4,5,6,7-tetrahydro-2H-pyrazolo[3,4-c]pyridine-3-carboxylic acid [2-(3,4-dichloro-phenyl)-ethyl]-amide | <1.00E−05 |
| 38 | 6-(1H-Benzotriazole-5-carbonyl)-4,5,6,7-tetrahydro-2H-pyrazolo[3,4-c]pyridine-3-carboxylic acid 2,5-dichloro-benzylamide | <1.00E−05 |
| 39 | 6-(1H-Benzotriazole-5-carbonyl)-4,5,6,7-tetrahydro-2H-pyrazolo[3,4-c]pyridine-3-carboxylic acid [2-(4-chloro-phenyl)-ethyl]-amide | <1.00E−06 |
| 40 | 6-(1H-Benzotriazole-5-carbonyl)-4,5,6,7-tetrahydro-2H-pyrazolo[3,4-c]pyridine-3-carboxylic acid [2-(4-chloro-phenyl)-1-hydroxymethyl-ethyl]-amide | 73% |
| 41 | 6-(1H-Benzotriazole-5-carbonyl)-4,5,6,7-tetrahydro-2H-pyrazolo[3,4-c]pyridine-3-carboxylic acid 2-methoxy-benzylamide | 66% |
| 42 | 6-(1H-Benzotriazole-5-carbonyl)-4,5,6,7-tetrahydro-2H-pyrazolo[3,4-c]pyridine-3-carboxylic acid [2-(3-chloro-phenyl)-ethyl]-amide | <3.00E−05 |
| 43 | 6-(1H-Benzotriazole-5-carbonyl)-4,5,6,7-tetrahydro-2H-pyrazolo[3,4-c]pyridine-3-carboxylic acid [2-(4-nitro-phenyl)-ethyl]-amide | <1.00E−05 |
| 44 | 6-(1H-Benzotriazole-5-carbonyl)-4,5,6,7-tetrahydro-2H-pyrazolo[3,4-c]pyridine-3-carboxylic acid [2-(4-bromo-phenyl)-ethyl]-amide | <1.00E−05 |
| 45 | 6-(1H-Benzotriazole-5-carbonyl)-4,5,6,7-tetrahydro-2H-pyrazolo[3,4-c]pyridine-3-carboxylic acid 5-chloro-2-methoxy-benzylamide | <1.00E−05 |
| 46 | 6-(1H-Benzotriazole-5-carbonyl)-4,5,6,7-tetrahydro-2H-pyrazolo[3,4-c]pyridine-3-carboxylic acid 4-chloro-2-fluoro-benzylamide | 76% |
| 47 | 6-(1H-Benzotriazole-5-carbonyl)-4,5,6,7-tetrahydro-2H-pyrazolo[3,4-c]pyridine-3-carboxylic acid [2-(4-fluoro-phenyl)-ethyl]-amide | <1.00E−05 |
| 48 | [2-(1H-Benzotriazole-5-carbonyl)-1,2,3,4-tetrahydro-isoquinolin-6-yl]-carbamic acid 3,5-dichloro-benzyl ester | <1.00E−05 |
| 49 | 6-(1H-Benzotriazole-5-carbonyl)-4,5,6,7-tetrahydro-2H-pyrazolo[3,4-c]pyridine-3-carboxylic acid 4-trifluoromethylsulfanyl-benzylamide | <3.00E−05 |
| 50 | 3-(1H-Benzotriazol-5-ylcarbamoyl)-1,4,5,7-tetrahydro-pyrazolo[3,4-c]pyridine-6-carboxylic acid 4-trifluoromethyl-benzyl ester | <1.00E−06 |
| 51 | 6-(1H-Benzotriazole-5-carbonyl)-4,5,6,7-tetrahydro-2H-pyrazolo[3,4-c]pyridine-3-carboxylic acid 3-bromo-4-fluoro-benzylamide | <1.00E−06 |
| 52 | 3-(1H-Benzotriazol-5-ylcarbamoyl)-2,4,5,7-tetrahydro-pyrazolo[3,4-c]pyridine-6-carboxylic acid 3,5-dichloro-benzyl ester | <1.00E−06 |
| 53 | 3-(1H-Benzotriazol-5-ylcarbamoyl)-2,4,5,7-tetrahydro-pyrazolo[3,4-c]pyridine-6-carboxylic acid 3,5-bis-trifluoromethyl-benzyl ester | <1.00E−06 |
| 54 | 3-(1H-Benzotriazol-5-ylcarbamoyl)-2,4,5,7-tetrahydro-pyrazolo[3,4-c]pyridine-6-carboxylic acid 3-chloro-4-trifluoromethyl-benzyl ester | <1.00E−05 |
| 55 | 3-(1H-Benzotriazol-5-ylcarbamoyl)-2,4,5,7-tetrahydro-pyrazolo[3,4-c]pyridine-6-carboxylic acid 3-trifluoromethyl-benzyl ester | <1.00E−06 |
| 56 | 3-(1H-Benzotriazol-5-ylcarbamoyl)-2,4,5,7-tetrahydro-pyrazolo[3,4-c]pyridine-6-carboxylic acid 4-trifluoromethylsulfanyl-benzyl ester | <1.00E−06 |

TABLE 4-continued

| Compound | Chemical Name | IC$_{50}$ value [M] or % CTRL (1E−05) |
|---|---|---|
| 57 | 3-(1H-Benzotriazol-5-ylcarbamoyl)-2,4,5,7-tetrahydro-pyrazolo[3,4-c]pyridine-6-carboxylic acid 4-trifluoromethoxy-benzyl ester | <1.00E−05 |
| 58 | 3-(1H-Benzotriazol-5-ylcarbamoyl)-2,4,5,7-tetrahydro-pyrazolo[3,4-c]pyridine-6-carboxylic acid 3-chloro-4-trifluoromethoxy-benzyl ester | <1.00E−06 |
| 59 | (1H-Benzotriazol-5-yl)-{3-[3-(4-methoxy-phenyl)-piperidine-1-carbonyl]-2,4,5,7-tetrahydro-pyrazolo[3,4-c]pyridin-6-yl}-methanone | <3.00E−05 |
| 60 | 6-(1H-Benzotriazole-5-carbonyl)-4,5,6,7-tetrahydro-2H-pyrazolo[3,4-c]pyridine-3-carboxylic acid 4-trifluoromethoxy-benzylamide | <3.00E−05 |
| 61 | 6-(1H-Benzotriazole-5-carbonyl)-4,5,6,7-tetrahydro-2H-pyrazolo[3,4-c]pyridine-3-carboxylic acid 4-trifluoromethyl-benzylamide | <1.00E−05 |
| 62 | 6-(1H-Benzotriazole-5-carbonyl)-4,5,6,7-tetrahydro-2H-pyrazolo[3,4-c]pyridine-3-carboxylic acid (6-methoxy-1,2,3,4-tetrahydro-naphthalen-2-yl)-amide | <1.00E−05 |
| 63 | 3-{[6-(1H-Benzotriazole-5-carbonyl)-4,5,6,7-tetrahydro-2H-pyrazolo[3,4-c]pyridine-3-carbonyl]-amino}-3-(4-tert-butyl-phenyl)-propionic acid methyl ester | <3.00E−05 |

The invention claimed is:

1. A compound according to formula (I)

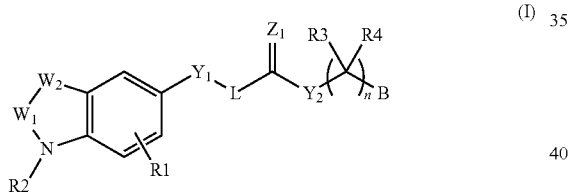

wherein:

$W_1$, $W_2$ together independently form "—N=N—, —C(O)—O—, —C(O)—S—, —C(O)—N(R5)-, —C(O)—C(R6)(R7)-, —N=C[N(R8)(R9)]-";

$Y_1$ is independently selected from the group consisting of "—C(O)—, —C(S)—, —N(R10)-C(O)—, —C(O)—N(R11)-, —C(R12)(R13)-, single bond";

$Y_2$ is independently selected from the group consisting of "—C(R14)(R15)-, —O—, —N(R16)-, —C(O)—NH—, single bond";

$Z_1$ is independently "O, S, or N(R17)";

L is independently:

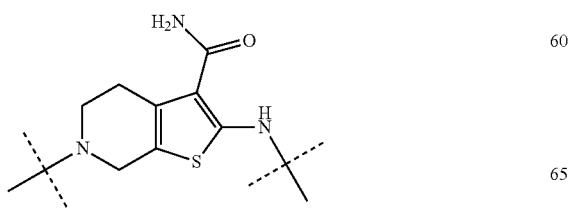

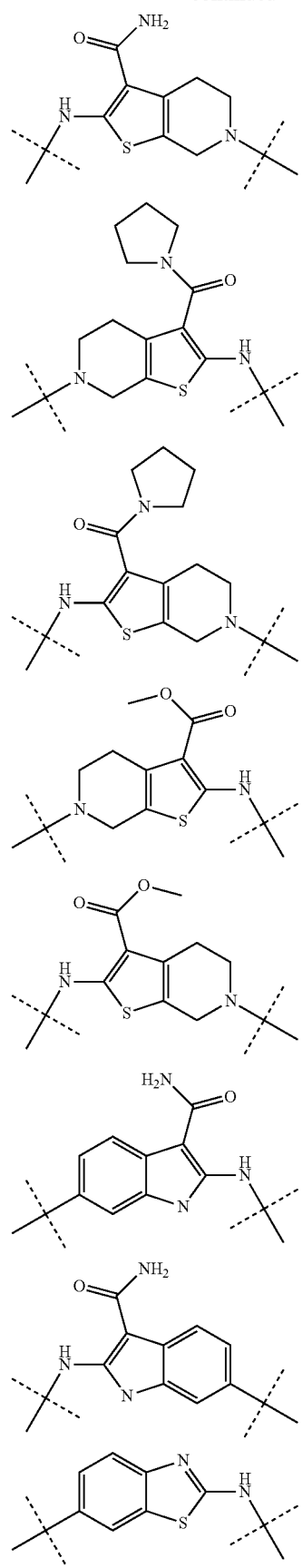

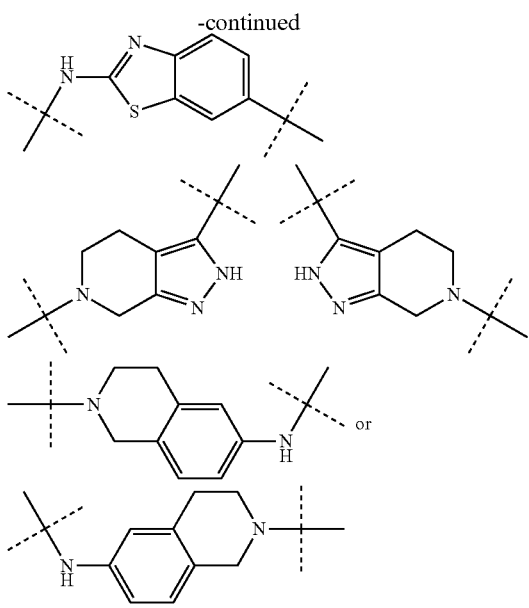

B is independently "cycloalkyl, heterocyclyl, aryl, or heteroaryl", wherein "cycloalkyl, heterocyclyl, aryl, or heteroaryl" can be independently substituted with one or more identical or different substituents that are: "(i) "hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, halogen, —F, —Cl, —Br, —I, —CN, —CF$_3$, —N$_3$, —NH$_2$, —NHX1, —NX2X3, —NO$_2$, —OH, —OCF$_3$, —SCF$_3$, —SH, —O—SO$_3$H, —OP(O)(OH)$_2$, —CHO, —COOH, —C(O)NH$_2$, —SO$_3$H, —P(O)(OH)$_2$, —C(O)—X4, —C(O)O—X5, —C(O)NH—X6, —C(O)NX7X8, —O—X9, —O(—X10-O)$_a$—H (a=1, 2, 3, 4, 5), —O(—X11-O)$_b$—X12 (b=1, 2, 3, 4, 5), —OC(O)—X13, —OC(O)—O—X14, —OC(O)—NHX15, —O—C(O)—NX16X17, —OP(O)(OX18)(OX19), —OSi(X20)(X21)(X22), —OS(O$_2$)—X23, —NHC(O)—NH$_2$, —NHC(O)—X24, —NX25C(O)—X26, —NH—C(O)—O—X27, —NH—C(O)—NH—X28, —NH—C(O)—NX29X30, —NX31-C(O)—O—X32, —NX33-C(O)—NH—X34, —NX35-C(O)—NX36X37, —NHS(O$_2$)—X38, —NX39S(O$_2$)—X40, —S—X41, —S(O)—X42, —S(O$_2$)—X43, —S(O$_2$)NH—X44, —S(O$_2$)NX45X46, —S(O$_2$)O—X47, —P(O)(OX48)(OX49), —Si(X50)(X51)(X52), —C(NH)—NH$_2$, —C(NX53)-NH$_2$, —C(NH)—NHX54, —C(NH)—NX55X56, —C(NX57)-NHX58, —C(NX59)-NX60X61, —NH—C(O)—NH—O—X62, —NH—C(O)—NX63-O—X64, —NX65-C(O)—NX66-O—X67, —N(—C(O)—NH—O—X68)$_2$, —N(—C(O)—NX69-O—X70)$_2$, —N(—C(O)—NH—O—X71)(—C(O)—NX72-O—X73), —C(S)—X74, —C(S)—O—X75, —C(S)—NH—X76, —C(S)—NX77X78, —C(O)—NH—O—X79, —C(O)—NX80-O—X81, —C(S)—NH—O—X82, —C(S)—NX83-O—X84, —C(O)—NH—NH—X85, —C(O)—NH—NX86X87, —C(O)—NX88-NX89X90, —C(S)—NH—NH—X91, —C(S)—NH—NX92X93, —C(S)—NX94-NX95X96, —C(O)—C(O)—O—X97, —C(O)—C(O)—NH$_2$, —C(O)—NHX98, —C(O)—C(O)—NX99X100, —C(S)—C(O)—O—X101, —C(O)—C(S)—O—X102, —C(S)—C(S)—O—X103, —C(S)—C(O)—NH$_2$, —C(S)—C(O)—NHX104, —C(S)—C(O)—NX105X106, —C(S)—C(S)—NH$_2$, —C(S)—C(S)—NHX107, —C(S)—C(S)—NX108X109, —C(O)—C(S)—NH$_2$, —C(O)—C(S)—NHX110, or —C(O)—C(S)—NX111X112";

wherein X1, X2, X3, X4, X5, X6, X7, X8, X9, X10, X11, X12, X13, X14, X15, X16, X17, X18, X19, X20, X21, X22, X23, X24, X25, X26, X27, X28, X29, X30, X31, X32, X33, X34, X35, X36, X37, X38, X39, X40, X41, X42, X43, X44, X45, X46, X47, X48, X49, X50, X51, X52, X53, X54, X55, X56, X57, X58, X59, X60, X61, X62, X63, X64, X65, X66, X67, X68, X69, X70, X71, X72, X73, X74, X75, X76, X77, X78, X79, X80, X81, X82, X83, X84, X85, X86, X87, X88, X89, X90, X91, X92, X93, X94, X95, X96, X97, X98, X99, X100, X101, X102, X103, X104, X105, X106, X107, X108, X109, X110, X111, X112 are independently:

"alkyl, (C$_9$-C$_{30}$)alkyl, cycloalkyl, cycloalkylalkyl, heterocyclyl, heterocyclylalkyl, aryl, arylalkyl, heteroaryl, or heteroarylalkyl" and wherein alternatively X7, X8 and/or X16, X17 and/or X29, X30 and/or X36, X37 and/or X45, X46 and/or X55, X56 and/or X60, X61 and/or X77, X78 and/or X86, X87 and/or X89, X90 and/or X92, X93 and/or X95, X96 and/or X99, X100 and/or X105, X106 and/or X108, X109 and/or X111, X112 respectively together can also form "heterocyclyl";

wherein optionally above substituents of substituents group (i) can in turn independently from each other be substituted with one or more identical or different substituents V;

R1, R2, R3, R4, R5, R6, R7, R8, R9, R10, R11, R12, R13, R14, R15, R16, R17 are independently: "V";

V is independently: "(i) hydrogen, alkyl, (C$_9$-C$_{30}$)alkyl, cycloalkyl, cycloalkylalkyl, heterocyclyl, heterocyclylalkyl, aryl, arylalkyl, heteroaryl, heteroarylalkyl, halogen, —F, —Cl, —Br, —I, —CN, —CF$_3$, —N$_3$, —NH$_2$, —NHA1, —NA2A3, —NO$_2$, —OH, —OCF$_3$, —SCF$_3$, —SH, —O—SO$_3$H, —OP(O)(OH)$_2$, —CHO, —COOH, —C(O)NH$_2$, —SO$_3$H, —P(O)(OH)$_2$, —C(O)-A4, —C(O)O-A5, —C(O)NH-A6, —C(O)NA7A8, —O-A9, —O(-A10-O)$_a$—H (a=1, 2, 3, 4, 5), —O(-A11-O)$_b$-A12 (b=1, 2, 3, 4, 5), —OC(O)-A13, —OC(O)-O-A14, —OC(O)—NHA15, —O—C(O)—NA16A17, —OP(O)(OA18)(OA19), —OSi(A20)(A21)(A22), —OS(O$_2$)-A23, —NHC(O)—NH$_2$, —NHC(O)-A24, —NA25C(O)-A26, —NH—C(O)—O-A27, —NH—C(O)—NH-A28, —NH—C(O)—NA29A30, —NA31-C(O)—O-A32, —NA33-C(O)—NH-A34, —NA35-C(O)—NA36A37, —NHS(O$_2$)-A38, —NA39S(O$_2$)-A40, —S-A41, —S(O)-A42, —S(O$_2$)-A43, —S(O$_2$)NH-A44, —S(O$_2$)NA45A46, —S(O$_2$)O-A47, —P(O)(OA48)(OA49), —Si(A50)(A51)(A52), —C(NH)—NH$_2$, —C(NA53)-NH$_2$, —C(NH)—NHA54, —C(NH)—NA55A56, —C(NA57)-NHA58, —C(NA59)-NA60A61, —NH—C(O)—NH—O-A62, —NH—C(O)—NA63-O-A64, —NA65-C(O)—NA66-O-A67, —N(—C(O)—NH—O-A68)$_2$, —N(—C(O)—NA69-O-A70)$_2$, —N(—C(O)—NH—O-A71)(—C(O)—NA72-O-A73), —C(S)-A74, —C(S)—O-A75, —C(S)—NH-A76, —C(S)—NA77A78, —C(O)—NH—O-A79, —C(O)—NA80-O-A81, —C(S)—NH—O-A82, —C(S)—NA83-O-A84, —C(O)—NH—NH-A85, —C(O)—NH—NA86A87, —C(O)—NA88-NA89A90, —C(S)—NH—NH-A91, —C(S)—NH—NA92A93, —C(S)—

NA94-NA95A96, —C(O)—C(O)—O-A97, —C(O)—C(O)—NH$_2$, —C(O)—C(O)—NHA98, —C(O)—C(O)—NA99A100, —C(S)—C(O)—O-A101, —C(O)—C(S)—O-A102, —C(S)—C(S)—O-A103, —C(S)—C(O)—NH$_2$, —C(S)—C(O)—NHA104, —C(S)—C(O)—NA105A106, —C(S)—C(S)—NH$_2$, —C(S)—C(S)—NHA107, —C(S)—C(S)—NA108A109, —C(O)—C(S)—NH$_2$, —C(O)—C(S)—NHA110, or —C(O)—C(S)—NA111A112";

wherein A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, A36, A37, A38, A39, A40, A41, A42, A43, A44, A45, A46, A47, A48, A49, A50, A51, A52, A53, A54, A55, A56, A57, A58, A59, A60, A61, A62, A63, A64, A65, A66, A67, A68, A69, A70, A71, A72, A73, A74, A75, A76, A77, A78, A79, A80, A81, A82, A83, A84, A85, A86, A87, A88, A89, A90, A91, A92, A93, A94, A95, A96, A97, A98, A99, A100, A101, A102, A103, A104, A105, A106, A107, A108, A109, A110, A111, A112 are independently: "alkyl, (C$_9$-C$_{30}$)alkyl, cycloalkyl, cycloalkylalkyl, heterocyclyl, heterocyclylalkyl, aryl, arylalkyl, heteroaryl, or heteroarylalkyl" and wherein alternatively A7, A8 and/or A16, A17 and/or A29, A30 and/or A36, A37 and/or A45, A46 and/or A55, A56 and/or A60, A61 and/or A77, A78 and/or A86, A87 and/or A89, A90 and/or A92, A93 and/or A95, A96 and/or A99, A100 and/or A105, A106 and/or A108, A109 and/or A111, A112 respectively together can also form "heterocyclyl";

wherein optionally above substituents of substituents group (i) can in turn independently from each other be substituted with one or more identical or different substituents V;

n is independently 0, 1, 2, 3 or 4;

or a physiologically acceptable salt, or stereoisomer thereof, including mixtures thereof in all ratios.

2. The compound according to formula (I) as claimed in claim 1, wherein:

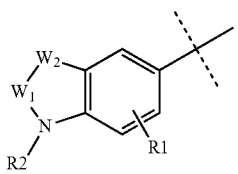

is independently substituted by a chemical group that is:

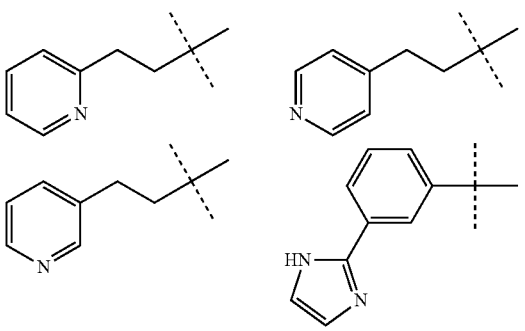

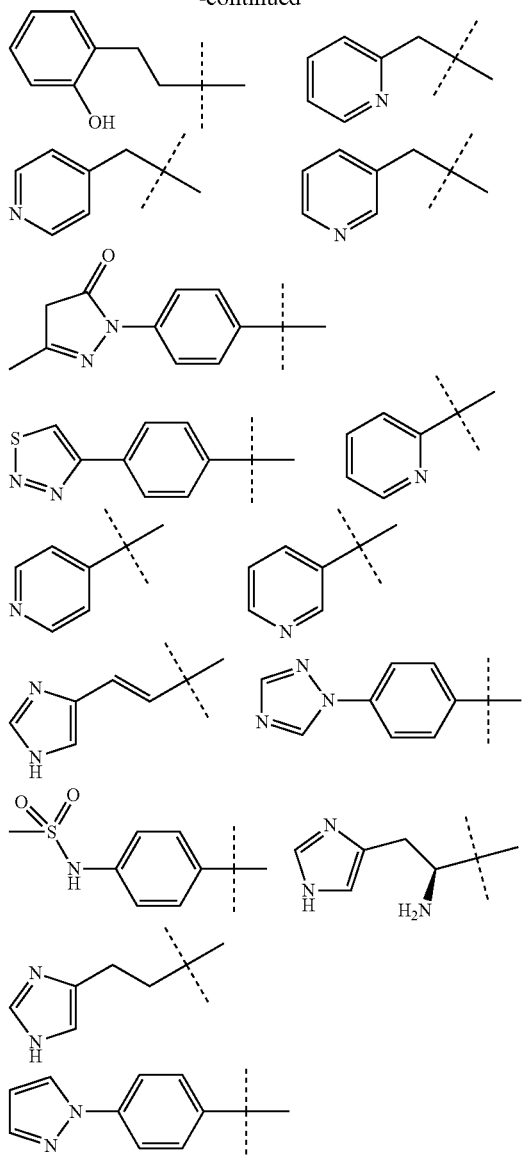

or a physiologically acceptable salt, or stereoisomer thereof, including mixtures thereof in all ratios.

3. The compound according to formulae (I) as claimed in claim 1, wherein:

W$_1$, W$_2$ together independently form "—N=N—, —C(O)—O—";

Y$_1$ is independently "—C(O)—, —N(R10)-C(O)—, —C(O)—N(R11)-, —OC(O)—, or a single bond";

Z$_1$ is independently "O";

B is independently "4-chloro-phenyl, 3-trifluoromethyl-phenyl, 4-trifluoromethyl-phenyl, 4-trifluoromethylsulfanyl-phenyl, 4-trifluoromethoxy-phenyl, 3-chloro-4-trifluoromethoxy-phenyl, 3,5-bis-trifluoromethyl-phenyl, 4-isopropylphenyl, 4-tert.butyl-phenyl, 3,5-dichloro-phenyl, 4-chloro-2-fluoro-phenyl, 3-chloro-phenyl, 2-fluoro-5-trifluoromethyl-phenyl, 3-chloro-4-trifluoromethyl-phenyl, 3,4-dichloro-phenyl, 2,5-dichloro-phenyl, 2-methoxy-phenyl, 4-methoxy-phenyl, 4-nitro-phenyl, 4-bromo-phenyl, 5-chloro-2-methoxy-phenyl, 4-fluoro-phenyl, 3-bromo-4-fluoro-phenyl, or 6-methoxy-1,2,3,4-tetrahydro-naphthalen-2-yl";

R1, R2, R3, R4, R5, R6, R7, R8, R9, R10, R11, R12, R13, R14, R15 are independently: "hydrogen, alkyl, methyl, isopropyl, tert.butyl, halogen, —F, —Br, —Cl, —CN, —CF$_3$, —SF$_5$, —OF$_3$, —O-alkyl, —O-methyl, —NO$_2$, or —S(O)$_2$-methyl"

V is independently "hydrogen, alkyl, methyl, isopropyl, tert.butyl, halogen, —F, —Br, —Cl, —CN, —CF$_3$, —SF$_5$, —OH, —O-alkyl, —O-methyl, —NO$_2$, or —S(O)$_2$-methyl";

n is independently 0, 1 or 2;

or a physiologically acceptable salt or stereoisomer thereof, including mixtures thereof in all ratios.

4. A compound of the formula:

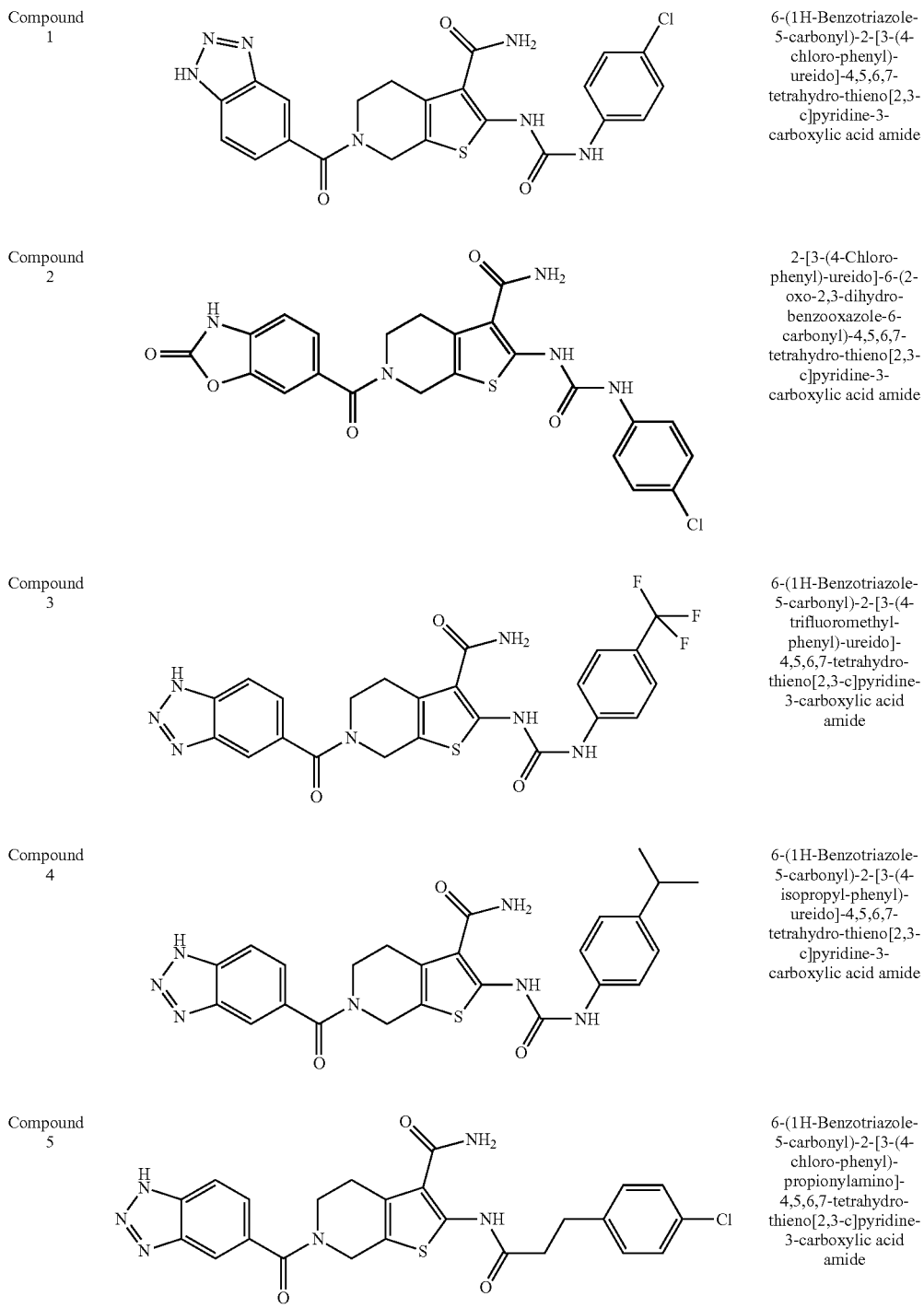

Compound 1 — 6-(1H-Benzotriazole-5-carbonyl)-2-[3-(4-chloro-phenyl)-ureido]-4,5,6,7-tetrahydro-thieno[2,3-c]pyridine-3-carboxylic acid amide Compound 2 — 2-[3-(4-Chloro-phenyl)-ureido]-6-(2-oxo-2,3-dihydro-benzooxazole-6-carbonyl)-4,5,6,7-tetrahydro-thieno[2,3-c]pyridine-3-carboxylic acid amide Compound 3 — 6-(1H-Benzotriazole-5-carbonyl)-2-[3-(4-trifluoromethyl-phenyl)-ureido]-4,5,6,7-tetrahydro-thieno[2,3-c]pyridine-3-carboxylic acid amide Compound 4 — 6-(1H-Benzotriazole-5-carbonyl)-2-[3-(4-isopropyl-phenyl)-ureido]-4,5,6,7-tetrahydro-thieno[2,3-c]pyridine-3-carboxylic acid amide Compound 5 — 6-(1H-Benzotriazole-5-carbonyl)-2-[3-(4-chloro-phenyl)-propionylamino]-4,5,6,7-tetrahydro-thieno[2,3-c]pyridine-3-carboxylic acid amide -continued

| | | |
|---|---|---|
| Compound 6 | | 2-[3-(4-Chloro-phenyl)-propionylamino]-6-(2-oxo-2,3-dihydro-benzooxazole-6-carbonyl)-4,5,6,7-tetrahydro-thieno[2,3-c]pyridine-3-carboxylic acid amide |
| Compound 7 | | 2-[3-(4-Isopropyl-phenyl)-ureido]-6-(2-oxo-2,3-dihydro-benzooxazole-6-carbonyl)-4,5,6,7-tetrahydro-thieno[2,3-c]pyridine-3-carboxylic acid amide |
| Compound 8 | | 2-[3-(3,5-Dichloro-phenyl)-ureido]-6-(2-oxo-2,3-dihydro-benzooxazole-6-carbonyl)-4,5,6,7-tetrahydro-thieno[2,3-c]pyridine-3-carboxylic acid amide |
| Compound 9 | | 6-(1H-Benzotriazole-5-carbonyl)-2-[2-(4-chloro-2-fluoro-phenyl)-acetylamino]-4,5,6,7-tetrahydro-thieno[2,3-c]pyridine-3-carboxylic acid amide |
| Compound 10 | | 2-[2-(4-Chloro-2-fluoro-phenyl)-acetylamino]-6-(2-oxo-2,3-dihydro-benzooxazole-6-carbonyl)-4,5,6,7-tetrahydro-thieno[2,3-c]pyridine-3-carboxylic acid amide |
| Compound 11 | | 6-(1H-Benzotriazole-5-carbonyl)-2-[2-(3-chloro-phenyl)-acetylamino]-4,5,6,7-tetrahydro-thieno[2,3-c]pyridine-3-carboxylic acid amide |
| Compound 12 | | 6-(1H-Benzotriazole-5-carbonyl)-2-[3-(3,5-dichloro-phenyl)-ureido]-4,5,6,7-tetrahydro-thieno[2,3-c]pyridine-3-carboxylic acid amide |

-continued

| | | |
|---|---|---|
| Compound 13 | 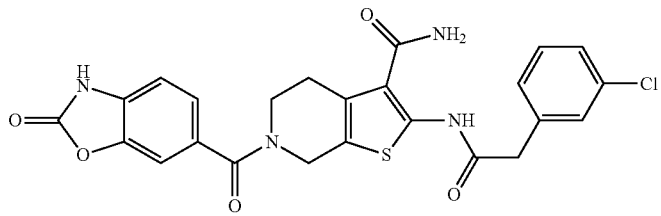 | 2-[2-(3-Chloro-phenyl)-acetylamino]-6-(2-oxo-2,3-dihydro-benzooxazole-6-carbonyl)-4,5,6,7-tetrahydro-thieno[2,3-c]pyridine-3-carboxylic acid amide |
| Compound 14 | 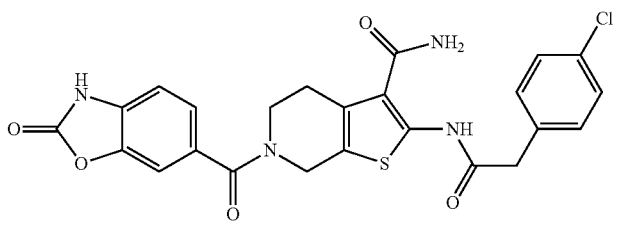 | 2-[2-(4-Chloro-phenyl)-acetylamino]-6-(2-oxo-2,3-dihydro-benzooxazole-6-carbonyl)-4,5,6,7-tetrahydro-thieno[2,3-c]pyridine-3-carboxylic acid amide |
| Compound 15 | 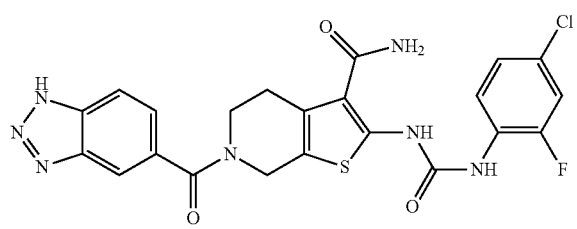 | 6-(1H-Benzotriazole-5-carbonyl)-2-[3-(4-chloro-2-fluoro-phenyl)-ureido]-4,5,6,7-tetrahydro-thieno[2,3-c]pyridine-3-carboxylic acid amide |
| Compound 16 | 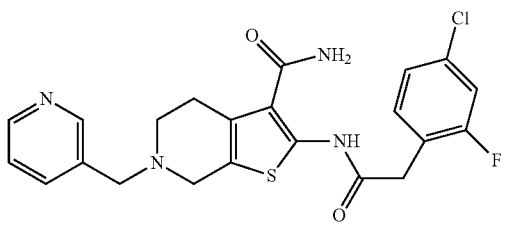 | 2-[2-(4-Chloro-2-fluoro-phenyl)-acetylamino]-6-pyridin-3-ylmethyl-4,5,6,7-tetrahydro-thieno[2,3-c]pyridine-3-carboxylic acid amide |
| Compound 17 | 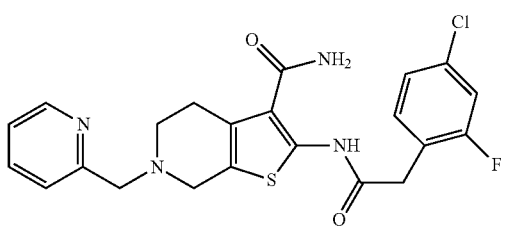 | 2-[2-(4-Chloro-2-fluoro-phenyl)-acetylamino]-6-pyridin-2-ylmethyl-4,5,6,7-tetrahydro-thieno[2,3-c]pyridine-3-carboxylic acid amide |
| Compound 18 | 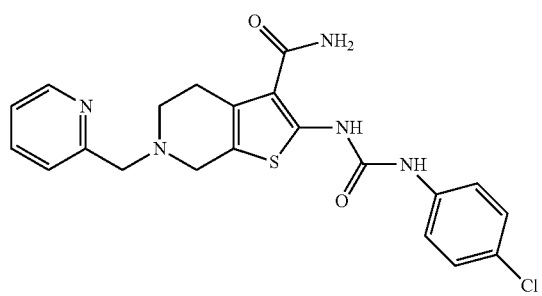 | 2-[3-(4-Chloro-phenyl)-ureido]-6-pyridin-2-ylmethyl-4,5,6,7-tetrahydro-thieno[2,3-c]pyridine-3-carboxylic acid amide |

-continued

| | | |
|---|---|---|
| Compound 19 | 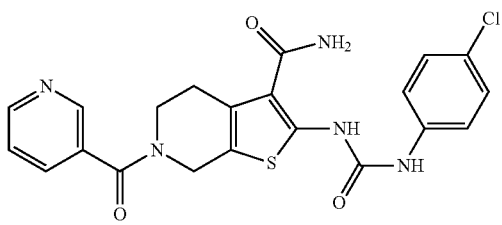 | 2-[3-(4-Chloro-phenyl)-ureido]-6-(pyridine-3-carbonyl)-4,5,6,7-tetrahydro-thieno[2,3-c]pyridine-3-carboxylic acid amide |
| Compound 20 | 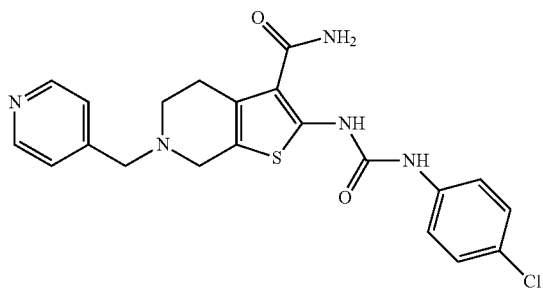 | 2-[3-(4-Chloro-phenyl)-ureido]-6-pyridin-4-ylmethyl-4,5,6,7-tetrahydro-thieno[2,3-c]pyiidine-3-carboxylic acid amide |
| Compound 21 | 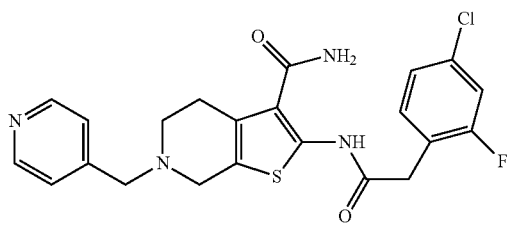 | 2-[2-(4-Chloro-2-fluoro-phenyl)-acetylamino]-6-pyridin-4-ylmethyl-4,5,6,7-tetrahydro-thieno[2,3-c]pyridine-3-carboxylic acid amide |
| Compound 22 | 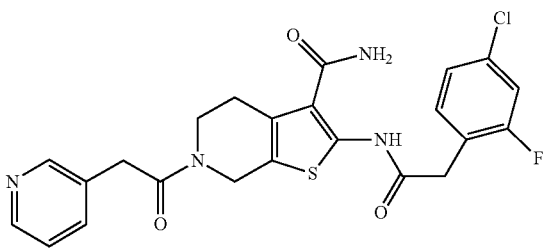 | 2-[2-(4-Chloro-2-fluoro-phenyl)-acetylamino]-6-(2-pyridin-3-yl-acetyl)-4,5,6,7-tetrahydro-thieno[2,3-c]pyridine-3-carboxylic acid amide |
| Compound 23 | 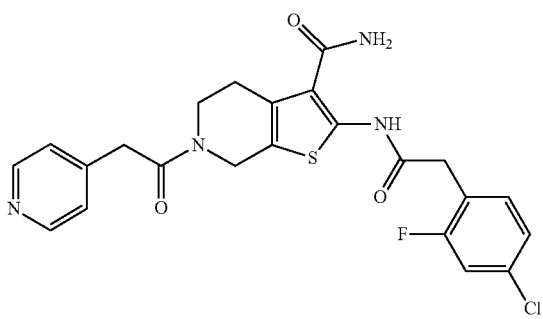 | 2-[2-(4-Chloro-2-fluoro-phenyl)-acetylamino]-6-(2-pyridin-4-yl-acetyl)-4,5,6,7-tetrahydro-thieno[2,3-c]pyridine-3-carboxylic acid amide |
| Compound 24 | 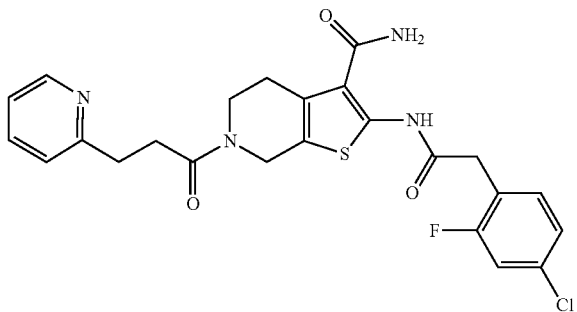 | 2-[2-(4-Chloro-2-fluoro-phenyl)-acetylamino]-6-(3-pyridin-2-yl-propionyl)-4,5,6,7-tetrahydro-thieno[2,3-c]pyridine-3-carboxylic acid amide |

| | | |
|---|---|---|
| Compound 25 | 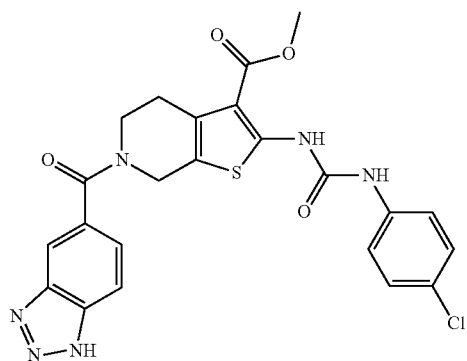 | 6-(1H-Benzotriazole-5-carbonyl)-2-[3-(4-chloro-phenyl)-ureido]-4,5,6,7-tetrahydro-thieno[2,3-c]pyridine-3-carboxylic acid methyl ester |
| Compound 26 | 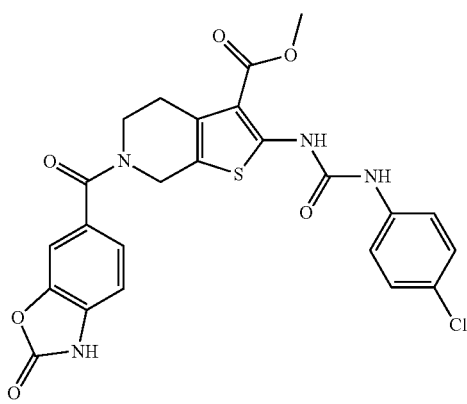 | 2-[3-(4-Chloro-phenyl)-ureido]-6-(2-oxo-2,3-dihydro-benzooxazole-6-carbonyl)-4,5,6,7-tetrahydro-thieno[2,3-c]pyridine-3-carboxylic acid methyl ester |
| Compound 27 | 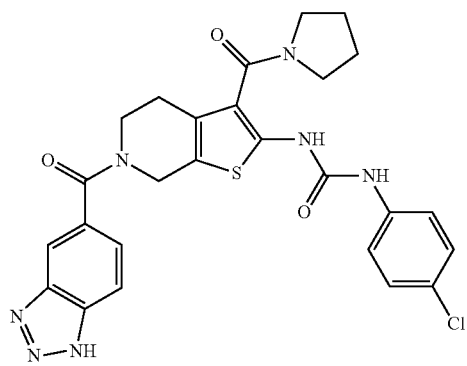 | 1-[6-(1H-Benzotriazole-5-carbonyl)-3-(pyrrolidine-1-carbonyl)-4,5,6,7-tetrahydro-thieno[2,3-c]pyridin-2-yl]-3-(4-chloro-phenyl)-urea |
| Compound 28 | 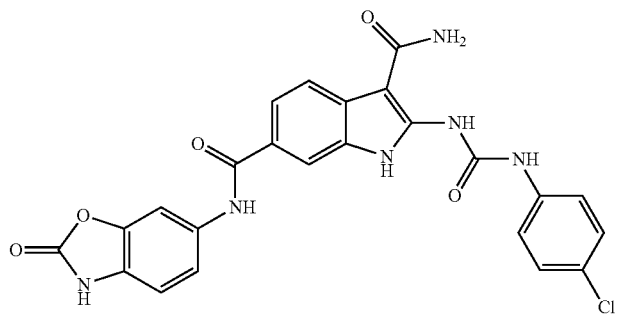 | 2-[3-(4-(Chloro-phenyl)-ureido]-1H-indole-3,6-dicarboxylic acid 3-amide 6-[(2-oxo-2,3-dihydro-benzooxazol-6-yl)-amide] |

| | | |
|---|---|---|
| Compound 29 | 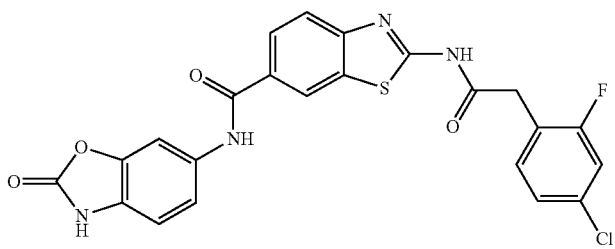 | 2-[2-(4-Chloro-2-fluoro-phenyl)-acetylamino]-benzothiazole-6-carboxylic acid (2-oxo-2,3-dihydro-benzooxazol-6-yl)-amide |
| Compound 30 | 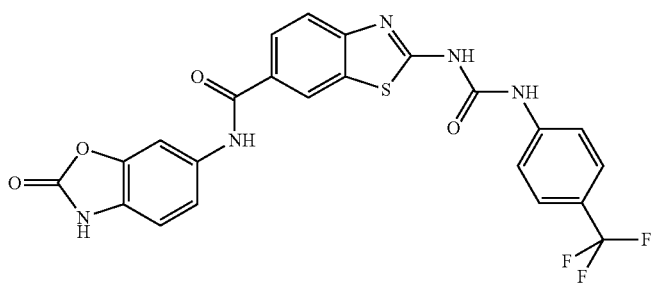 | 2-[3-(4-Trifluoromethyl-phenyl)-ureido]-benzothiazole-6-carboxylic acid (2-oxo-2,3-dihydro-benzooxazol-6-yl)-amide |
| Compound 31 | 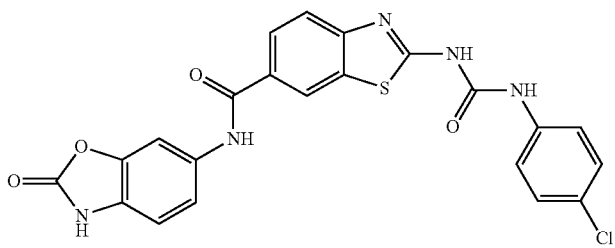 | 2-[3-(4-Chloro-phenyl)-ureido]-benzothiazole-6-carboxylic acid (2-oxo-2,3-dihydro-benzooxazol-6-yl)-amide |
| Compound 32 | 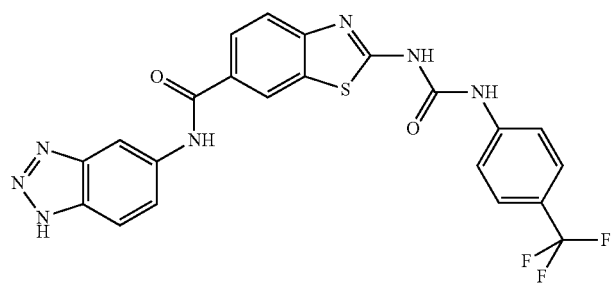 | 2-[3-(4-Trifluoromethyl-phenyl)-ureido]-benzothiazole-6-carboxylic acid (1H-benzotriazol-5-yl)-amide |
| Compound 33 | 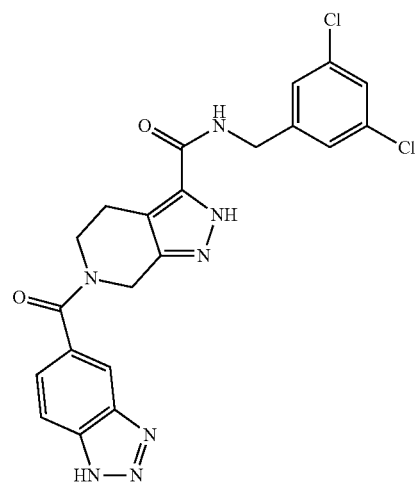 | 6-(1H-Benzotriazole-5-carbonyl)-4,5,6,7-tetrahydro-2H-pyrazolo[3,4-c]pyridine-3-carboxylic acid 3,5-dichloro-benzylamide |

-continued
| | | |
|---|---|---|
| Compound 34 | 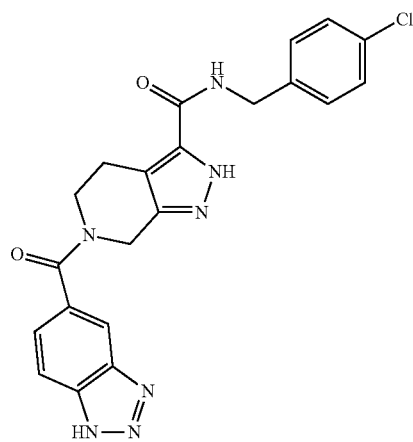 | 6-(1H-Benzotriazole-5-carbonyl)-4,5,6,7-tetrahydro-2H-pyrazolo[3,4-c]pyridine-3-carboxylic acid 4-chloro-benzylamide |
| Compound 35 | 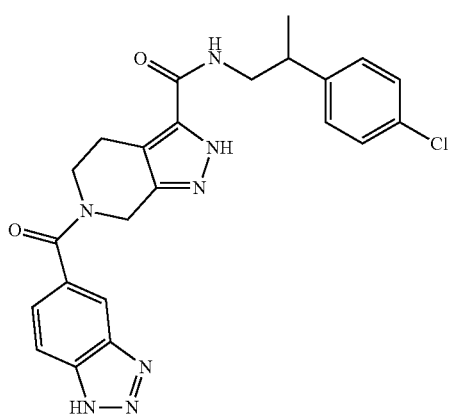 | 6-(1H-Benzotriazole-5-carbonyl)-4,5,6,7-tetrahydro-2H-pyrazolo[3,4-c]pyridine-3-carboxylic acid [2-(4-chloro-phenyl)-propyl]-amide |
| Compound 36 | 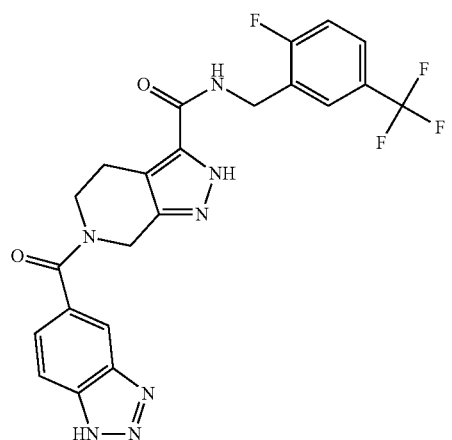 | 6-(1H-Benzotriazole-5-carbonyl)-4,5,6,7-tetrahydro-2H-pyrazolo[3,4-c]pyridine-3-carboxylic acid 2-fluoro-5-trifluoromethyl-benzylamide |

-continued

| | | |
|---|---|---|
| Compound 37 | 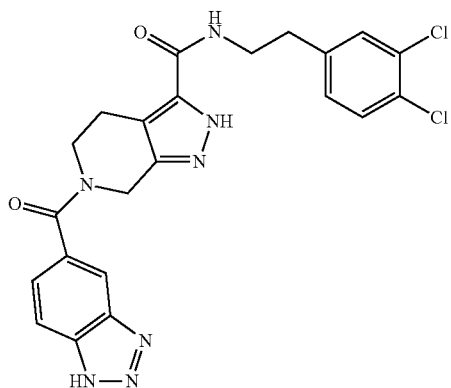 | 6-(1H-Benzotriazole-5-carbonyl)-4,5,6,7-tetrahydro-2H-pyrazolo[3,4-c]pyridine-3-carboxylic acid [2-(3,4-dichloro-phenyl)-ethyl]-amide |
| Compound 38 | 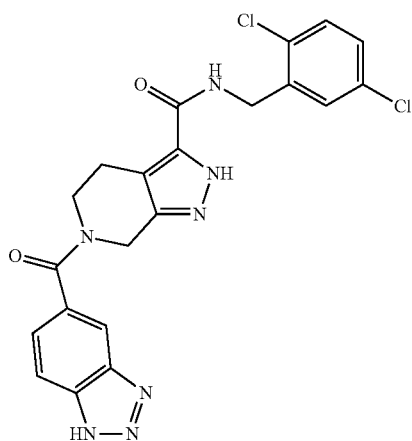 | 6-(1H-Benzotriazole-5-carbonyl)-4,5,6,7-tetrahydro-2H-pyrazolo[3,4-c]pyridine-3-carboxylic acid 2,5-dichloro-benzylamide |
| Compound 39 | 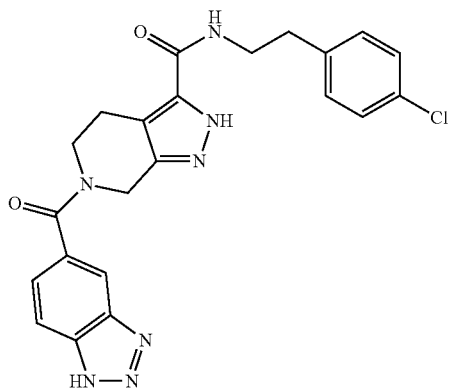 | 6-(1H-Benzotriazole-5-carbonyl)-4,5,6,7-tetrahydro-2H-pyrazolo[3,4-c]pyridine-3-carboxylic acid [2-(4-chloro-phenyl)-ethyl]-amide |
| Compound 40 | 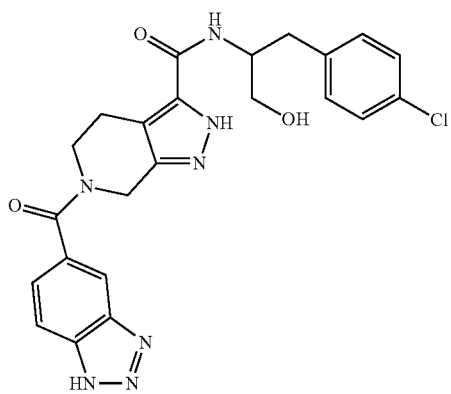 | 6-(1H-Benzotriazole-5-carbonyl)-4,5,6,7-tetrahydro-2H-pyrazolo[3,4-c]pyridine-3-carboxylic acid [2-(4-chloro-phenyl)-1-hydroxymethyl-ethyl]-amide |

-continued

| Compound 41 | 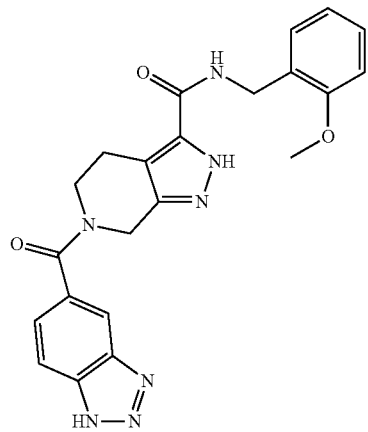 | 6-(1H-Benzotriazole-5-carbonyl)-4,5,6,7-tetrahydro-2H-pyrazolo[3,4-c]pyridine-3-carboxylic acid 2-methoxy-benzylamide |
| Compound 42 | 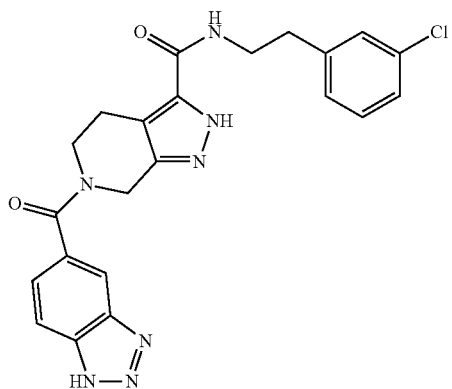 | 6-(1H-Benzotriazole-5-carbonyl)-4,5,6,7-tetrahydro-2H-pyrazolo[3,4-c]pyridine-3-carboxylic acid [2-(3-chloro-phenyl)-ethyl]-amide |
| Compound 43 | 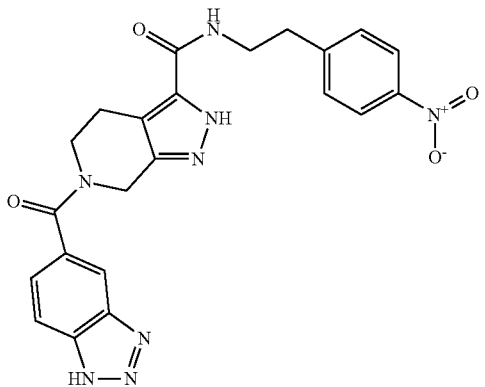 | 6-(1H-Benzotriazole-5-carbonyl)-4,5,6,7-tetrahydro-2H-pyrazolo[3,4-c]pyridine-3-carboxylic acid [2-(4-nitro-phenyl)-ethyl]-amide |
| Compound 44 | 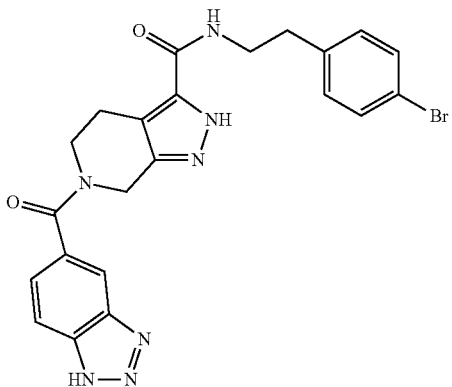 | 6-(1H-Benzotriazole-5-carbonyl)-4,5,6,7-tetrahydro-2H-pyrazolo[3,4-c]pyridine-3-carboxylic acid [2-(4-bromo-phenyl)-ethyl]-amide |

| | | |
|---|---|---|
| Compound 45 | 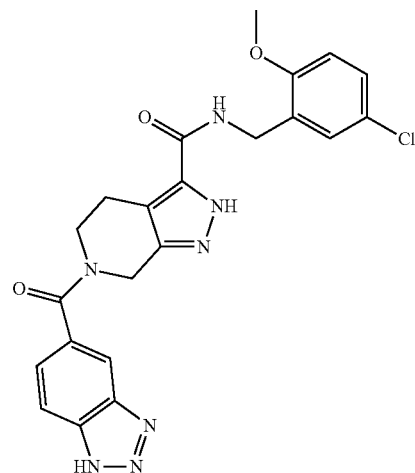 | 6-(1H-Benzotriazole-5-carbonyl)-4,5,6,7-tetrahydro-2H-pyrazolo[3,4-c]pyridine-3-carboxylic acid 5-chloro-2-methoxy-benzylamide |
| Compound 46 | 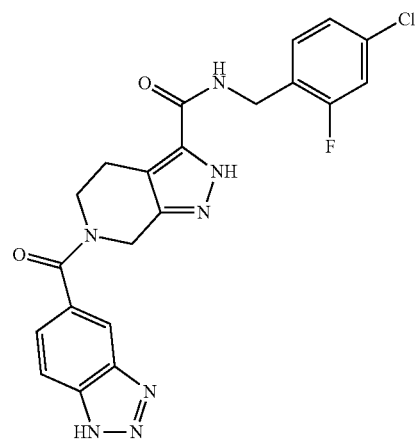 | 6-(1H-Benzotriazole-5-carbonyl)-4,5,6,7-tetrahydro-2H-pyrazolo[3,4-c]pyridine-3-carboxylic acid 4-chloro-2-fluoro-benzylamide |
| Compound 47 | 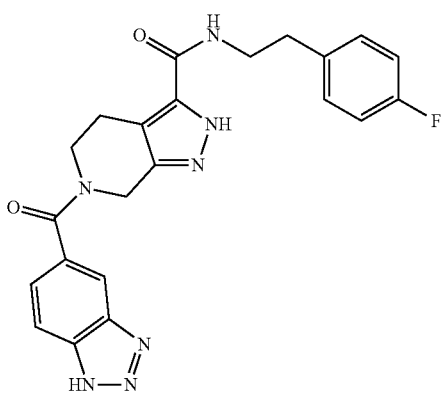 | 6-(1H-Benzotriazole-5-carbonyl)-4,5,6,7-tetrahydro-2H-pyrazolo[3,4-c]pyridine-3-carboxylic acid [2-(4-fluoro-phenyl)-ethyl]-amide |
| Compound 48 | 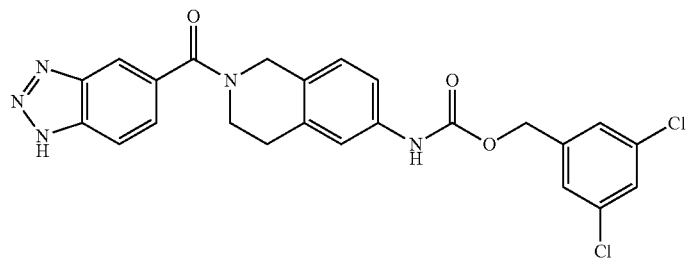 | [2-(1H-Benzotriazole-5-carbonyl)-1,2,3,4-tetrahydro-isoquinolin-6-yl]-carbamic acid 3,5-dichloro-benzyl ester |

| Compound 49 | 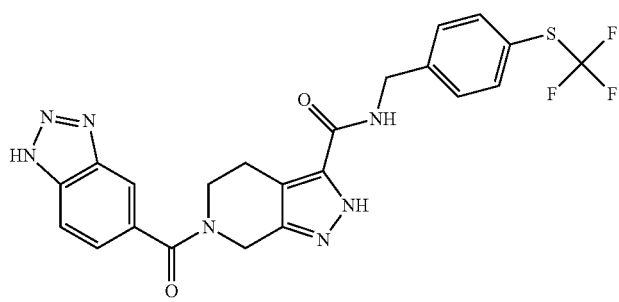 | 6-(1H-Benzotriazole-5-carbonyl)-4,5,6,7-tetrahydro-2H-pyrazolo[3,4-c]pyridine-3-carboxylic acid 4-trifluoromethylsulfanyl-benzylamide |
| Compound 50 | 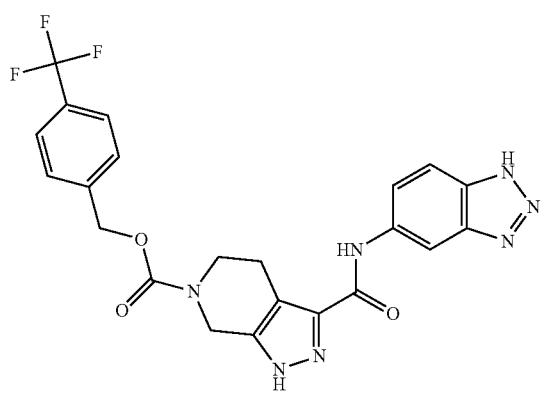 | 3-(1H-Benzotriazol-5-ylcarbamoyl)-1,4,5,7-tetrahydro-pyrazolo[3,4-c]pyridine-6-carboxylic acid 4-trifluoromethyl-benzyl ester |
| Compound 51 | 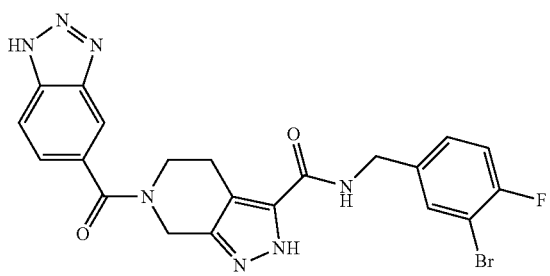 | 6-(1H-Benzotriazole-5-carbonyl)-4,5,6,7-tetrahydro-2H-pyrazolo[3,4-c]pyridine-3-carboxylic acid 3-bromo-4-fluoro-benzylamide |
| Compound 52 | 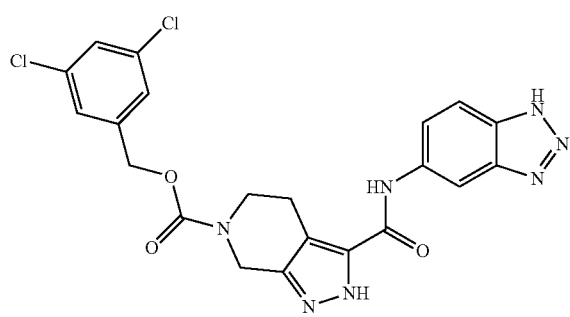 | 3-(1H-Benzotriazol-5-ylcarbamoyl)-2,4,5,7-tetrahydro-pyrazolo[3,4-c]pyridine-6-carboxylic acid 3,5-dichloro-benzyl ester |
| Compound 53 | 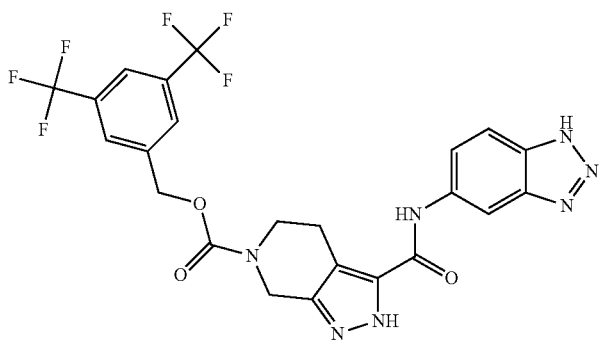 | 3-(1H-Benzotriazol-5-ylcarbamoyl)-2,4,5,7-tetrahydro-pyrazolo[3,4-c]pyridine-6-carboxylic acid 3,5-bis-trifluoromethyl-benzyl ester |

-continued

| | | |
|---|---|---|
| Compound 54 | 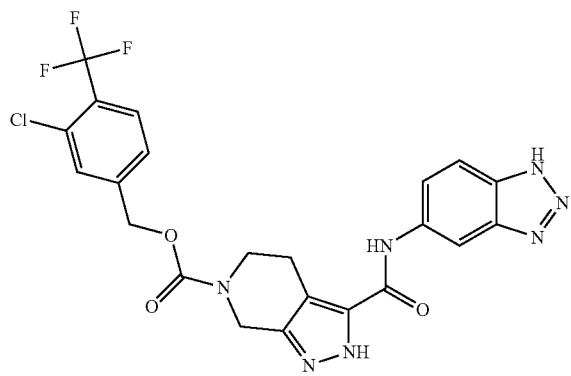 | 3-(1H-Benzotriazol-5-ylcarbamoyl)-2,4,5,7-tetrahydro-pyrazolo[3,4-c]pyridine-6-carboxylic acid 3-chloro-4-trifluoromethyl-benzyl ester |
| Compound 55 | 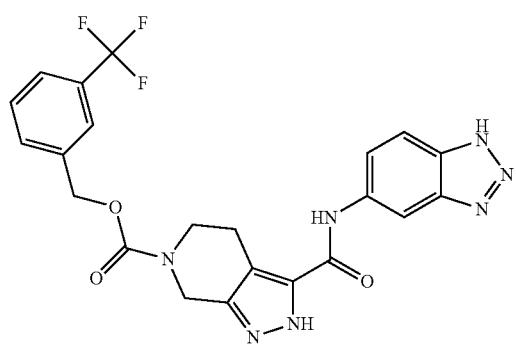 | 3-(1H-Benzotriazol-5-ylcarbamoyl)-2,4,5,7-tetrahydro-pyrazolo[3,4-c]pyridine-6-carboxylic acid 3-trifluoromethyl-benzyl ester |
| Compound 56 | 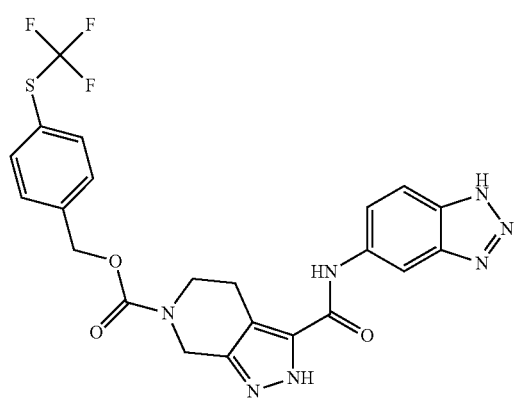 | 3-(1H-Benzotriazol-5-ylcarbamoyl)-2,4,5,7-tetrahydro-pyrazolo[3,4-c]pyridine-6-carboxylic acid 4-trifluoromethylsulfanyl-benzyl ester |
| Compound 57 | 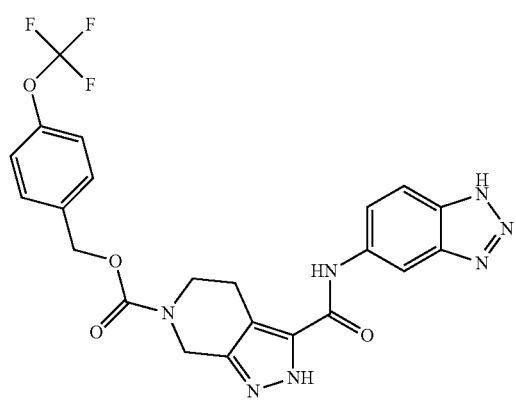 | 3-(1H-Benzotriazol-5-ylcarbamoyl)-2,4,5,7-tetrahydro-pyrazolo[3,4-c]pyridine-6-carboxylic acid 4-trifluoromethoxy-benzyl ester |

| | | |
|---|---|---|
| Compound 58 | 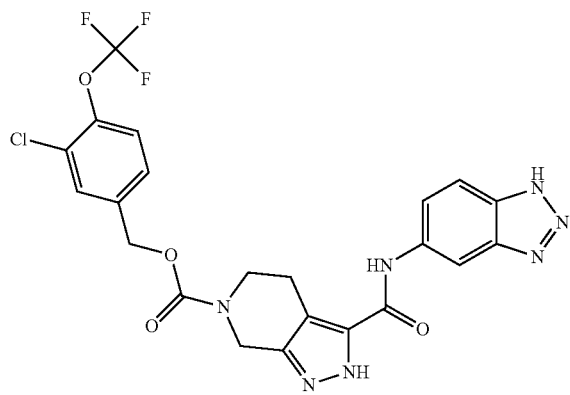 | 3-(1H-Benzotriazol-5-ylcarbamoyl)-2,4,5,7-tetrahydro-pyrazolo[3,4-c]pyridine-6-carboxylic acid 3-chloro-4-trifluoromethoxy-benzyl ester |
| Compound 59 | 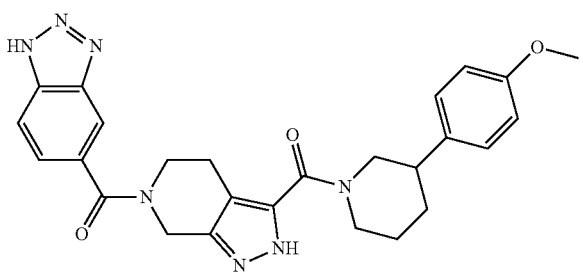 | (1H-Benzotriazol-5-yl)-{3-[3-(4-methoxy-phenyl)-piperidine-1-carbonyl]-2,4,5,7-tetrahydro-pyrazolo[3,4-c]pyridin-6-yl}-methanone |
| Compound 60 | 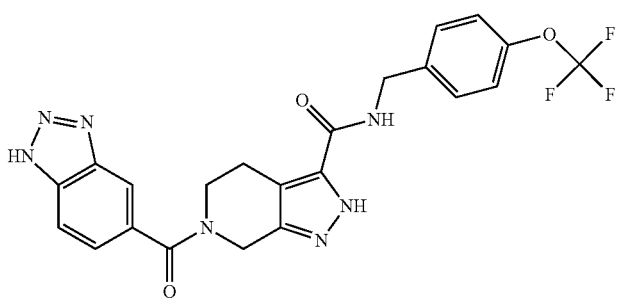 | 6-(1H-Benzotriazole-5-carbonyl)-4,5,6,7-tetrahydro-2H-pyrazolo[3,4-c]pyridine-3-carboxylic acid 4-trifluoromethoxy-benzylamide |
| Compound 61 | 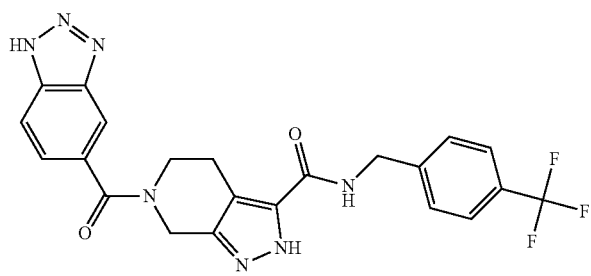 | 6-(1H-Benzotriazole-5-carbonyl)-4,5,6,7-tetrahydro-2H-pyrazolo[3,4-c]pyridine-3-carboxylic acid 4-trifluoromethyl-benzylamide |
| Compound 62 | 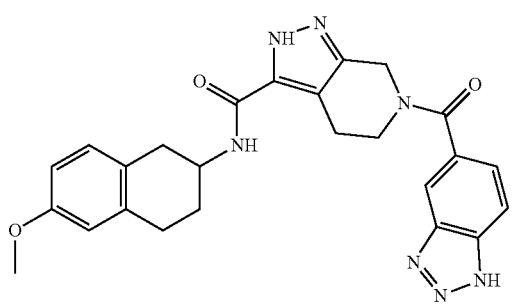 | 6-(1H-Benzotriazole-5-carbonyl)-4,5,6,7-tetrahydro-2H-pyrazolo[3,4-c]pyridine-3-carboxylic acid (6-methoxy-1,2,3,4-tetrahydro-naphthalen-2-yl)-amide | or

| | | |
|---|---|---|
| Compound 63 | 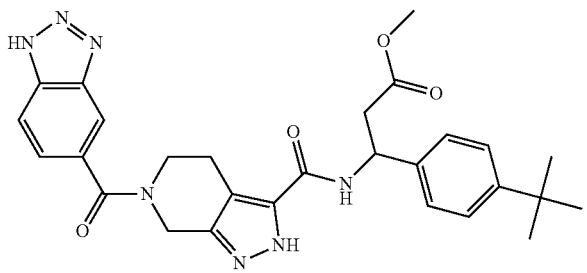 | 3-{[6-(1H-Benzotriazole-5-carbonyl)-4,5,6,7-tetrahydro-2H-pyrazolo[3,4-c]pyridine-3-carbonyl]-amino}-3-(4-tert-butyl-phenyl)-propionic acid methyl ester. |

5. A process for the preparation of a compound according to formula (I) as claimed in claim 1, comprising:

(a) reacting a compound of the formula (II),

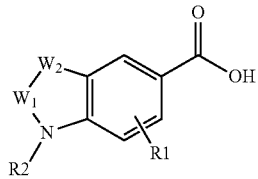
(II)

wherein $W_1$, $W_2$, R1, R2 have the meanings as indicated for the compound of formula (I), with a compound of formula (III)

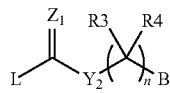
(III)

wherein L is:

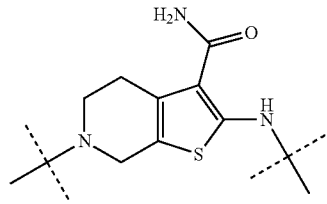

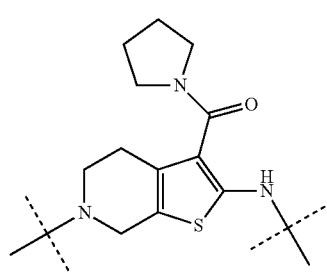

-continued

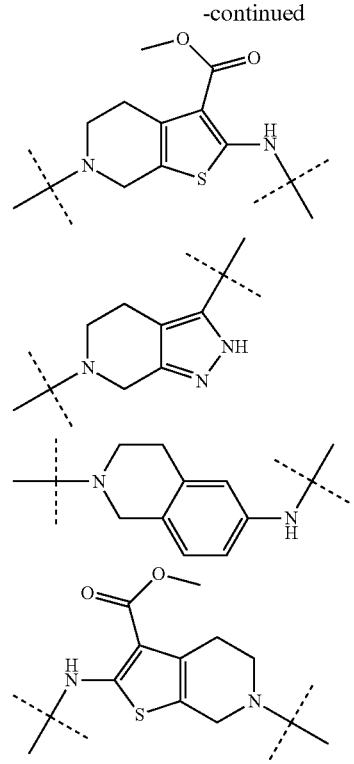

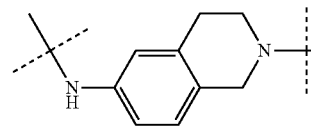
or

-continued

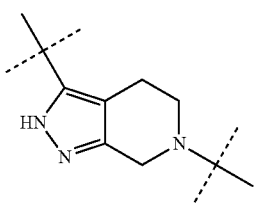

and wherein $Z_1$, $Y_2$, R3, R4, B, n have the meanings as indicated for the compound of formula (I), to yield a compound according to formula (I) in which $Y_1$ denotes "—C(O)—";

or (b) reacting a compound of formula (II)

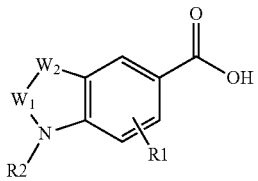
(II)

wherein $W_1$, $W_2$, R1, R2 have the meanings as indicated for the compound of formula (I), with a compound L:

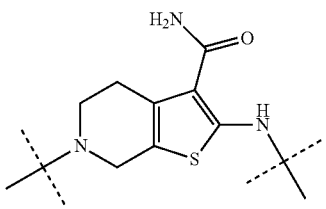

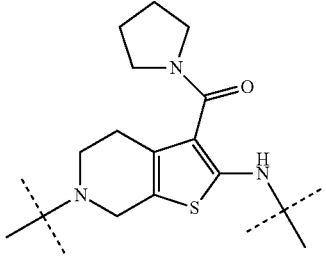

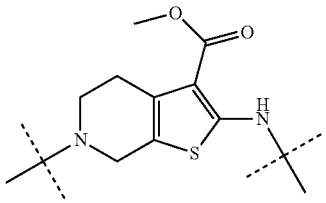

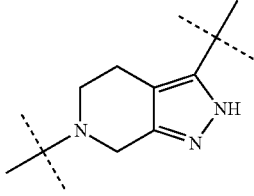

-continued

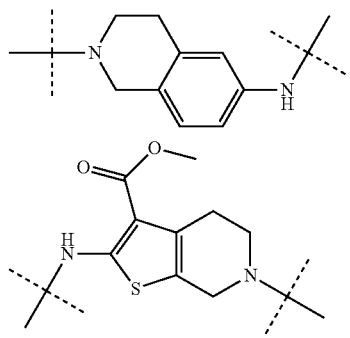

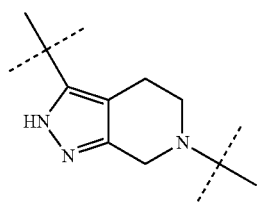  or

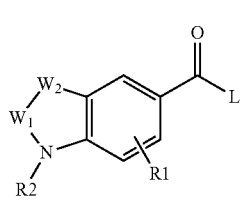

to yield a compound of formula (IIa)

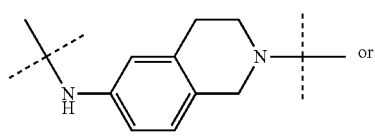
(IIa)

wherein $W_1$, $W_2$, R1, R2 have the meanings as indicated for the compound of formula (I), further reacting the compound of formula (IIa) with a compound of formula (IV)

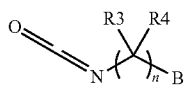
(IV)

wherein R3, R4, B, n have the meanings as indicated for the compound of formula (I), to yield a compound according to formula (I), in which $Z_1$ denotes "O" and $Y_2$ denotes "—N(R16)-" and R16 denotes "H";

or (c) reacting a compound of formula (Va) or (Vb)

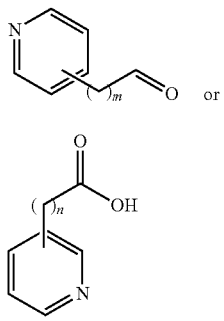

wherein m and n independently are 0, 1 or 2, with a compound of the formula (III)

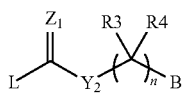
(III)

wherein L is:

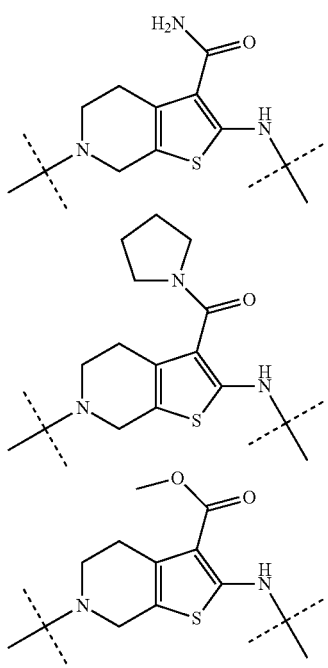

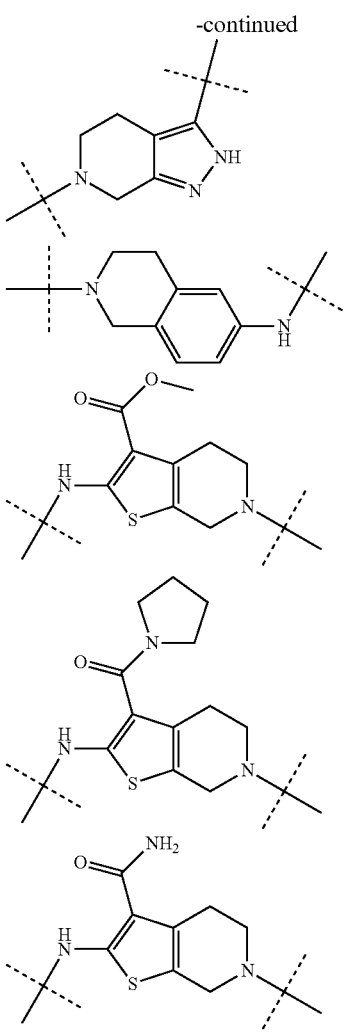

and wherein $Z_1$, $Y_2$, R3, R4, B, n have the meanings as indicated for the compound of formula (I), to yield a compound according to formula (I), in which $Y_1$, denotes "—C(R12)(R13)- and R12, R13 both denote "H" or $Y_1$ denotes "—C(O)—", or (d) reacting a compound of formula (VI)

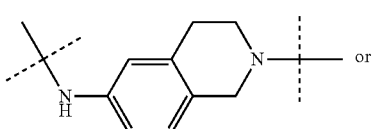 (VI)

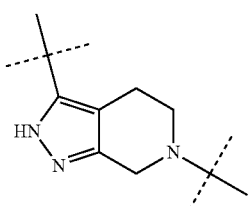

wherein L is:

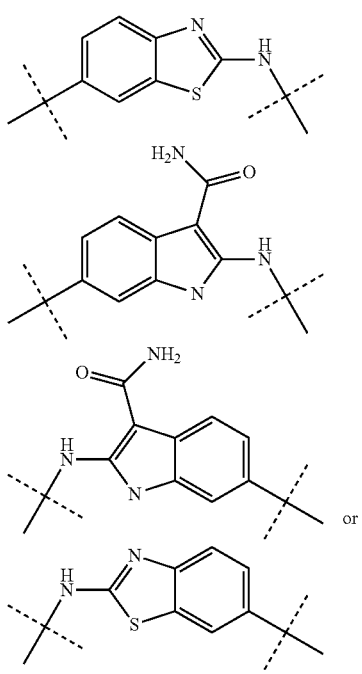

with a compound of formula (VII)

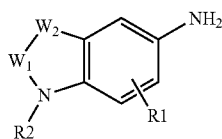
(VII)

wherein $W_1$, $W_2$, R1, R2 have the meanings as indicated for the compound of formula I, to yield a compound of formula (VIII)

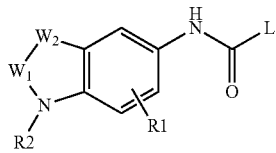
(VIII)

wherein $W_1$, $W_2$, R1, R2 have the meanings as indicated for the compound of formula (I), further reacting the compound of formula (VIII) with a compound of formula (IV)

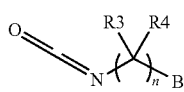
(IV)

wherein R3, R4, B, n have the meanings as indicated for the compound of formula (I), to yield a compound according to formula (I), in which $Y_1$ denotes "—N(R10)-C(O)—", R10 denotes "H", $Z_1$ denotes "O", $Y_2$ denotes "—N(R16)-" and R16 denotes "H";

or (e) reacting a compound of formula (IX)

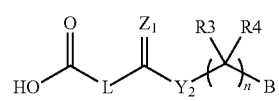
(IX)

wherein L is:

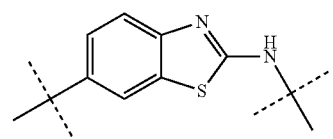

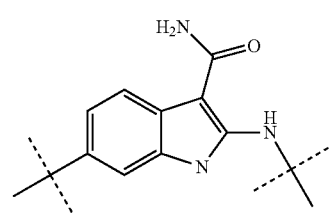

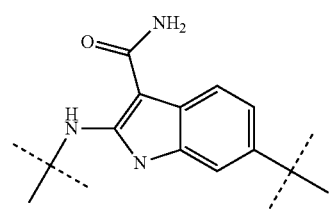

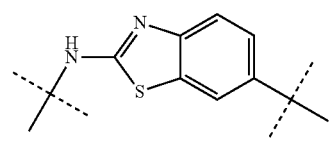

and wherein $Z_1$, $Y_2$, R3, R4, B, n have the meanings as indicated for the compound of formula (I), with a compound of formula (VII)

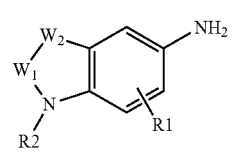
(VII)

wherein $W_1$, $W_2$, R1, R2 have the meanings as indicated for the compound of formula (I), to yield a compound according to formula (I), in which $Y_1$ denotes "—N(R10)-C(O)—" and R10 denotes "H".

or (f) reacting a compound of formula (X)

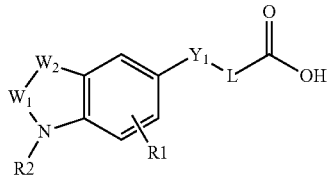

wherein $W_1$, $W_2$, R1, R2, $Y_1$ have the meanings as indicated for the compound of formula (I), wherein L is:

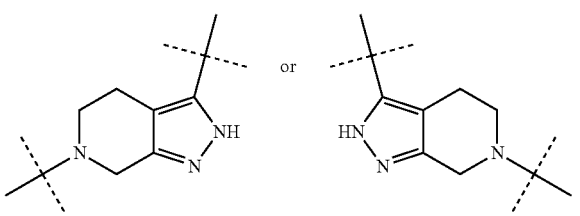

with a compound of formula (XI)

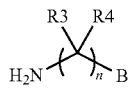

wherein R3, R4, B, n have the meanings as indicated for the compound of formula (I), to yield a compound according to formula (I), in which $Z_1$ denotes "O", $Y_2$ denotes "—N(R16)-" and R16 denotes "H".

6. A pharmaceutical composition comprising a compound as claimed in claim 1, and a pharmaceutically acceptable carrier.

7. The pharmaceutical composition as claimed in claim 6 further comprising at least one additional pharmaceutically active substance other than the compound of formula (I).

8. A kit comprising a compound as claimed in claim 1 and further pharmacologically active substance other than the compound of formula (I).

* * * * *